(12) United States Patent
Anderson et al.

(10) Patent No.: US 9,717,790 B2
(45) Date of Patent: Aug. 1, 2017

(54) SPHINGOGLYCOLIPID ANALOGUES

(71) Applicant: Victoria Link Limited, Wellington (NZ)

(72) Inventors: Regan James Anderson, Lower Hutt (NZ); Benjamin Jason Compton, Lower Hutt (NZ); Colin Malcolm Hayman, Lower Hutt (NZ); Ian Francis Hermans, Wellington (NZ); Karen Anne Johnston, Lower Hutt (NZ); David Samuel Larsen, Dunedin (NZ); Gavin Frank Painter, Lower Hutt (NZ)

(73) Assignee: Victoria Link Limited, Wellington (NZ)

( * ) Notice: Subject to any disclaimer, the term of this patent is extended or adjusted under 35 U.S.C. 154(b) by 0 days.

(21) Appl. No.: 14/897,601

(22) PCT Filed: Jun. 10, 2014

(86) PCT No.: PCT/NZ2014/000113
§ 371 (c)(1),
(2) Date: Dec. 10, 2015

(87) PCT Pub. No.: WO2014/200363
PCT Pub. Date: Dec. 18, 2014

(65) Prior Publication Data
US 2016/0136267 A1 May 19, 2016

(30) Foreign Application Priority Data

Jun. 10, 2013 (NZ) ........................ 611741

(51) Int. Cl.
| | | |
|---|---|---|
| *A61K 39/00* | (2006.01) | |
| *A61K 39/39* | (2006.01) | |
| *C07D 493/08* | (2006.01) | |
| *C07H 15/04* | (2006.01) | |
| *C07H 15/26* | (2006.01) | |
| *C07H 19/01* | (2006.01) | |
| *A61K 31/7028* | (2006.01) | |
| *C07H 5/10* | (2006.01) | |
| *C07H 15/14* | (2006.01) | |
| *C07H 17/02* | (2006.01) | |
| *C07D 493/04* | (2006.01) | |
| *A61K 31/7056* | (2006.01) | |
| *A61K 31/706* | (2006.01) | |

(52) U.S. Cl.
CPC ............ *A61K 39/39* (2013.01); *A61K 31/706* (2013.01); *A61K 31/7028* (2013.01); *A61K 31/7056* (2013.01); *A61K 39/0011* (2013.01); *C07D 493/04* (2013.01); *C07D 493/08* (2013.01); *C07H 5/10* (2013.01); *C07H 15/04* (2013.01); *C07H 15/14* (2013.01); *C07H 15/26* (2013.01); *C07H 17/02* (2013.01); *C07H 19/01* (2013.01); *A61K 2039/55572* (2013.01); *A61K 2039/55583* (2013.01)

(58) Field of Classification Search
CPC ...... C07D 493/04; C07H 15/04; C07H 15/26; C07H 17/02; C07H 19/01
USPC .......... 424/277.1, 279.1; 536/17.4, 17.6, 53; 549/363
See application file for complete search history.

(56) References Cited

U.S. PATENT DOCUMENTS 8,053,417 B2 * 11/2011 Ebensen .............. A61K 9/0019
514/23

OTHER PUBLICATIONS

The Merck Manual 1992, 16th Ed., pp. 183-189, 339-342, 1263, 166-169 and 1488-1490.*
Trisha Gura, Science, Nov., 1997, pp. 1041-1042.*
Atherton et al., "A Mild Procedure for Solid Phase Peptide Synthesis: Use of Fluorenylmethoxycarbonylamino-acids," J.C.S. Chem. Comm. 13:537-539, 1978.
Bach et al., "Synthesis of Five-, Six-, and Seven-Membered Heterocycles by Intramolecular Ring Opening Reactions of 3-Oxetanol Derivatives," J. Org. Chem. 63:1910-1918, 1998.
Baek et al., "The 3-Deoxy Analogue of α-GalCer: Disclosing the Role of the 4-Hydroxyl Group for CD1d-Mediated NKT Cell Activation," ACS Medicinal Chemistry Letters 2:544-548, 2011.
Bahrami et al., "Direct Conversion of Thiols to Sulfonyl Chlorides and Sulfonamides," Journal of Organic Chemistry 74:9287-9291, 2009.
Banchet-Cadeddu et al., "The stimulating adventure of KRN 7000," Organic & Biomolecular Chemistry 9:3080-3104, 2011.
Banwell et al., "A Pd[0]-catalyzed Ullmann cross-coupling/reductive cyclization approach to C-3 mono-alkylated oxindoles and related compounds," Tetrahedron 66:9252-9262, 2010.
Bendelac et al., "The Biology of NKT Cells," Annual Review of Immunology 25:297-336, 2007.
Bernard et al., "Processing of Tumor Antigen Differentially Impacts the Development of Helper and Effector CD4+ T-cell Responses," Molecular Therapy 18(6):1224-1232, 2010.
Bettinotti et al., "Stringent Allele/Epitope Requirements for MART-1/Melan A Immunodominance: Implications for Peptide-Based Immunotherapy," Journal of Immunology 161:877-889, 1998.
Black et al., "Advances in the design and delivery of peptide subunit vaccines with a focus on Toll-like receptor agonists," Expert Review of Vaccines 9(2):157-173, 2010.

(Continued)

Primary Examiner — Ganapathy Krishnan
(74) Attorney, Agent, or Firm — Seed IP Law Group LLP

(57) ABSTRACT

The invention relates to sphingoglycolipid analogues which are useful in treating or preventing diseases and conditions such as those relating to infection, atopic disorders, autoimmune diseases or cancer.

19 Claims, 8 Drawing Sheets

(56) References Cited

OTHER PUBLICATIONS

Brossart et al., "Identification of HLA-A2-Restricted T-Cell Epitopes Derived From the MUC1 Tumor Antigen for Broadly Applicable Vaccine Therapies," *Blood* 93(2):4309-4317, 1999.
Burkhard et al., "Oxetanes as Versatile Elements in Drug Discovery and Synthesis," *Angew. Chem. Int. Ed.* 49:9052-9067, 2010.
Butler et al., "Reactions of Fatty Acids with Amines. Part 2. Sequential Thermal Reactions of Stearic (Octadecanoic) Acid with Some 1,2- and 1,3-Amino-alcohols and Bis-amines," *Journal of the Chemical Society, Perkin Transactions* 1(4):373-377, 1978.
Chang, "Efficient amplification of melanoma-specific $CD8^+$ T cells using artificial antigen presenting complex," *Experimental and Molecular Medicine* 38(6):591-598, 2006.
Chen et al., "Efficient Synthesis of α-C-Galactosyl Ceramide Immunostimulants: Use of Ethylene-Promoted Olefin Cross-Metathesis," *Organic Letters* 6(22):4077-4080, 2004.
Chen et al., "Synthesis and biological evaluation of technetium-99m-labeled deoxyglucose derivatives as imaging agents for tumor," *Bioorganic & Medicinal Chemistry Letters* 16:5503-5506, 2006.
Chen et al., "Synthesis and antibacterial activity of novel modified 5-O-desosamine ketolides," *Bioorganic & Medicinal Chemistry Letters* 22:7402-7405, 2012.
Ciesielski et al., "Therapeutic effect of a T helper cell supported CTL response induced by a survivin peptide vaccine against murine cerebral glioma," *Cancer Immunol. Immunother.* 57:1827-1835, 2008.
Davidson et al., "Effect of TA-CIN (HPV 16 L2E6E7) booster immunisation in vulval intraepithelial neoplasia patients previously vaccinated with TA-HPV (vaccinia virus encoding HPV 16/18 E6E7)," *Vaccine* 22:2722-2729, 2004.
de Araújo et al., "Diels-Alder Ligation of Peptides and Proteins," *Chem. Eur. J.* 12:6095-6109, 2006.
Deng et al., "Impact of sugar stereochemistry on natural killer T cell stimulation by bacterial glycolipids," *Org. Biomol. Chem.* 9:7659-7662, 2011.
Dere et al., "The First Synthesis of a Thioglycoside Analogue of the Immunostimulant KRN7000," *Organic Letters* 10(20):4641-4644, 2008.
Dietz et al., "Synthese neuer Pyrrolidin-2,5-dione," *Zeitschrift für Chemie* 29(8):284-285, 1989, with English Translation. (4 pages).
Divakar et al., "Approaches to the Synthesis of 2'-Thio Analogues of Pyrimidine Ribosides," *J. Chem. Soc. Perkin Trans.* 1:969-974, 1990.
Du et al., "Efficient, one-pot syntheses of biologically active α-linked glycolipids," *Chemical Communications* 23:2336-2338, 2007.
Ebensen et al., "A Pegylated Derivative of α-Galactosylceramide Exhibits Improved Biological Properties," *J. Immunol.* 179:2065-2073, 2007.
Fascione et al., "Stereoselective glycosylations using oxathiane spiroketal glycosyl donors," *Carbohydrate Research* 348:6-13, 2012.
Fields et al., "Solid phase peptide synthesis utilizing 9-fluorenylmethoxycarbonyl amino acids," *Int. J. Peptide Protein Res.* 35:161-214, 1990.
Friedrichs et al., "Survivin-derived peptide epitopes and their role for induction of antitumor immunity in hematological malignancies," *Leukemia & Lymphoma* 47(6):978-985, 2006.
Frohlich et al., "2,2,2-Trifluoroethyl 6-thio-β-D-glucopyranoside as a selective tag for cysteines in proteins," *Carbohydrate Research* 361:100-104, 2012.
Fujii et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein," *The Journal of Experimental Medicine* 198(2):267-279, 2003.

Fujiwara et al., "Application of a New Chiral Phosphepine to the Catalytic Asymmetric Synthesis of Highly Functionalized Cyclopentenes That Bear an Array of Heteroatom-Substituted Quaternary Stereocenters," *Journal of the American Chemical Society* 133:12293-12297, 2011.
Le Gal et al., "Design and synthesis of a novel family of semi-rigid ligands: versatile compounds for the preparation of $^{99m}Tc$ radiopharmaceuticals," *Org. Biomol. Chem.* 2:876-883, 2004.
Giaccone et al., "A Phase I Study of the Natural Killer T-Cell Ligand α-Galactosylceramide (KRN7000) in Patients with Solid Tumors," *Clinical Cancer Research* 8:3702-3709, 2002.
Girouard et al., "Synthesis and Characterization of Dimaleimide Fluorogens Designed for Specific Labeling of Proteins," *J. Am. Chem. Soc.* 127:559-566, 2005.
González-Temprano et al., "Enantiodivergent Synthesis of Pyrrolo[2,1-a]isoquinolines Based on Diastereoselective Parham Cyclization and α-Amidoalkylation Reactions," *J. Org. Chem.* 69:3875-3885, 2004.
Gourtas et al., "Inhibition of Human Leukocyte Elastase by Derivatives of N-Hydroxysuccinimide. A Structure-Activity-Relationship Study," *J. Med. Chem.* 32:1607-1611, 1989.
Greene et al., *Protective Groups in Organic Synthesis*, New York, John Wiley & Sons, Inc., 1991, pp. 1-9. (13 pages).
Hermans et al., "NKT Cells Enhance $CD4^+$ and $CD8^+$ T Cell Responses to Soluble Antigen In Vivo through Direct Interaction with Dendritic Cells," *The Journal of Immunology* 171:5140-5147, 2003.
Hermans et al., "The VITAL assay: a versatile fluorometric technique for assessing CTL- and NKT-mediated cytotoxicity against multiple targets in vitro and in vivo," *Journal of Immunological Methods* 285:25-40, 2004.
Hong et al., "The natural killer T-cell ligand α-galactosylceramide prevents autoimmune diabetes in non-obese diabetic mice," *Nature Medicine* 7(9):1052-1056, 2001.
Howell et al., "Approaches to the preparation of sphinganines," *Tetrahedron* 60:11327-11347, 2004.
Huarte et al., "Enhancing Immunogenicity of a CTL Epitope from Carcinoembryonic Antigen by Selective Amino Acid Replacements," *Clinical Cancer Research* 8:2336-2344, 2002.
Isobe et al., "Synthesis of Fullerene Glycoconjugates via a Copper-Catalyzed Huisgen Cycloaddition Reaction," *Organic Letters* 9(22):4611-4614, 2007.
Jager et al., "Peptide-Specific CD8+ T-Cell Evolution In Vivo: Response to Peptide Vaccination with Melan-A/Mart-1," *Int. J. Cancer* 98:376-388, 2002.
Johansen et al., "Synthesis of Carbasugars from Aldonolactones: Ritter-Type Epoxide Opening in the Synthesis of Polyhydroxylated Aminocylcopentanes," *Synthesis* 1:171-177, 1999.
Jones et al., "Polymeric Dibromomaleimides as Extremely Efficient Disulfide Bridging Bioconjugation and Pegylation Agents," *Journal of the American Chemical Society* 134:1847-1852, 2012.
Joyce et al., "Synthesis of the Aromatic and Monosaccharide Moieties of Staurosporine," *The Journal of Organic Chemistry* 52(7):1177-1185, 1987.
Karbach et al., "Tumor-reactive $CD8^+$ T-cell responses after vaccination with NY-ESO-1 peptide, CpG 7909 and Montanide® ISA-51: association with survival," *International Journal of Cancer* 126:909-918, 2010.
Kawano et al., "CD1d-Restricted and TCR-Mediated Activation of $V_\alpha14$ NKT Cells by Glycosylceramides," *Science* 278(5343):1626-1629, 1997.
Kinjo et al., "Invariant natural killer T cells recognize glycolipids from pathogenic Gram-positive bacteria," *Nature Immunology* 12(10):966-974, 2011.
Knothe et al., "The NKT cell ligand agalactosylceramide suppresses allergic airway inflammation by induction of a Th1 response," *Vaccine* 29:4249-4255, 2011.
Kværnø et al., "Synthesis and in Vitro Evaluation of Inhibitors of Intestinal Cholesterol Absorption," *J. Med. Chem.* 48:6035-6053, 2005.
Lee et al., "Novel synthesis of α-galactosyl-ceramides and confirmation of their powerful NKT cell agonist activity," *Carbohydrate Research* 341:2785-2798, 2006.

(56) References Cited

OTHER PUBLICATIONS

Levy et al., "A melanoma multiepitope polypeptide induces specific CD8+ T-cell response," *Cellular Immunology* 250:24-30, 2008.
Li et al., "Design of a potent CD1d-binding NKT cell ligand as a vaccine adjuvant," *PNAS* 107(29):13010-13015, 2010.
Li et al., "The Vα14 invariant natural killer T cell TCR forces microbial glycolipids and CD1d into a conserved binding mode," *The Journal of Experimental Medicine* 207(11):2383-2393, 2010.
Li et al., "Identification of a WT1 protein-derived peptide, WT1$_{187}$, as a HLA-A 0206-restricted, WT1-specific CTL epitope," *Microbiol. Immunol.* 52:551-558, 2008.
Liptak et al., "The first synthesis of secondary sugar sulfonic acids by nucleophilic displacement reactions," *Tetrahedron Letters* 45:839-842, 2004.
Lu et al., "Synthesis and Evaluation of an α-C-Galactosylceramide Analogue that Induces Th1-biased Responses in Human Natural Killer T Cells," *ChemBioChem* 7:1750-1756, 2006.
Lu et al., "Induction of the Epstein-Barr Virus Latent Membrane Protein 2 Antigen-specific Cytotoxic T Lymphocytes Using Human Leukocyte Antigen Tetramer-based Artificial Antigen-presenting Cells," *Acta Biochimica et Biophysica Sinica* 38(3):157-163, 2006.
Majireck et al., "A Study of the Scope and Regioselectivity of the Ruthenium-Catalyzed [3+2]-Cycloaddition of Azides with Internal Alkynes," *J. Org. Chem.* 71:8680-8683, 2006.
Manzo et al., "Chemo-enzymatic preparation of α-6-sulfoquinovosyl-1,2-O-diacylglycerols," *Tetrahedron* 68:10169-10175, 2012.
Moree et al., "Synthesis of Peptidosulfinamides and Peptidosulfonamides: Peptidomimetics Containing the Sulfinamide or Sulfonamide Transition-State Isostere," *J. Org. Chem.* 60:5157-5169, 1995.
Morita et al., "Structure-Activity Relationship of α-Galactosylceramides against B16-Bearing Mice," *J. Med. Chem.* 38:2176-2187, 1995.
Motoki et al., "Immunostimulatory and Antitumor Activities of Monoglycosylceramides Having Various Sugar Moieties," *Biol. Pharm. Bull.* 18(11):1487-1491, 1995.
Muus et al., "Development of antiproliferative phenylmaleimides that activate the unfolded protein response," *Bioorganic & Medicinal Chemistry* 18:4535-4541, 2010.
Noppen et al., "Naturally processed and concealed HLA-A2.1 restricted epitopes from tumor associated antigen tyrosinase-related protein-2," *Journal of the American College of Surgeons* 191(45):S71, 2000.
Obreza et al., "Recent Advances in Design, Synthesis and Biological Activity of Aminoalkylsulfonates and Sulfonamidopeptides," *Current Medicinal Chemistry* 11:3263-3278, 2004.
O'Reilly et al., "Synthesis of α-S-Glycosphingolipids Based on Uronic Acids," *Organic Letters* 13(19):5168-5171, 2011.
Parekh et al., "Glycolipid antigen induces long-term natural killer T cell anergy in mice," *Journal of Clinical Investigation* 115(9):2572-2583, 2005.
Park et al., "Exploration of SAR regarding glucose moiety in novel C-aryl glucoside inhibitors of SGLT2," *Bioorganic & Medicinal Chemistry Letters* 21:742-746, 2011.
Park et al., "Synthesis of all stereoisomers of KRN7000, the CD1d-binding NKT cell ligand," *Bioorganic & Medicinal Chemistry Letters* 18:3906-3909, 2008.
Plettenburg et al., "Synthesis of α-Galactosyl Ceramide, a Potent Immunostimulatory Agent," *J. Org. Chem.* 67:4559-4564, 2002.
Pu et al., "C-Galactosylceramide diastereomers via Sharpless asymmetric epoxidation chemistry," *Tetrahedron* 64:8618-8629, 2008.
Raju et al., "Synthesis and evaluation of 3"- and 4"-deoxy and -fluoro analogs of the immunostimulatory glycolipid, KRN7000,"*Bioorganic & Medicinal Chemistry Letters* 19:4122-4125, 2009.
Ren et al., "Regiochemical and Stereochemical Studies on Halogen-Induced Ring Expansions of Unsaturated Episulfides," *J. Org. Chem.* 60:6484-6495, 1995.

Rim et al., "Thiol-ene reactions of 1,3,5-triacryloylhexahydro-1,3,5-triazine (TAT): facile access to functional tripodal thioethers," *Tetrahedron Letters* 50:745-747, 2009.
Rostovtsev et al., "A Stepwise Huisgen Cycloaddition Process: Copper(I)-Catalyzed Regioselective "Ligation" of Azides and Terminal Alkynes," *Angew. Chem. Int. Ed.* 41(14):2596-2599, 2002.
Sakurai et al., "Design and synthesis of functionalized trisaccharides as p53-peptide mimics," *Tetrahedron Letters* 51:3724-3727, 2010.
Saxon et al., "Cell Surface Engineering by a Modified Staudinger Reaction," *Science* 287:2007-2010, 2000.
Schmitz et al., "Generation of Survivin-specific CD8+ T Effector Cells by Dendritic Cells Pulsed with Protein or Selected Peptides," *Cancer Research* 60:4845-4849, 2000.
Schumacher et al., "In Situ Maleimide Bridging of Disulfides and a New Approach to Protein PEGylation," *Bioconjugate Chemistry* 22:132-136, 2011.
Sherry et al., "Rhenium(V)-Catalyzed Synthesis of 2-Deoxy-α-glycosides," *J. Am. Chem. Soc.* 126:4510-4511, 2004.
Silk et al., "Utilizing the adjuvant properties of CD1d-dependent NKT cells in T cell-mediated immunotherapy," *Journal of Clinical Investigation* 114(12): 1800-1811, 2004.
Smeenk et al., "Synthesis of Water-Soluble Scaffolds for Peptide Cyclization, Labeling, and Ligation," *Organic Letters* 14(5):1194-1197, 2012.
Smith et al., Protein Modification, Bioconjugation, and Disulfide Bridging Using Bromomalelmides, *J. Am. Chem. Soc.* 132:1960-1965, 2010.
Speiser et al., "Molecularly defined vaccines for cancer immunotherapy, and protective T cell immunity," *Seminars in Immunology* 22:144-154, 2010.
Spescha, "124. Introduction of a New Class of Ligands for the Metal-Catalyzed Enantioselective Synthesis," *Helvetica Chimica Acta* 76:1832-1846, 1993.
Stewart et al., "A concise synthesis of maleic anhydride and maleimide natural products found in *Antrodia camphorata*," *Tetrahedron Letters* 48:2241-2244, 2007.
Tashiro et al., "RCAI-61, the 6'-O-methylated analog of KRN7000: its synthesis and potent bioactivity for mouse lymphocytes to produce interferon-γ in vivo," *Tetrahedron Letters* 49:6827-6830, 2008.
Tedaldi et al., "[2+2] Photocycloadditions of thiomaleimides," *Chem. Commun.* 48:4725-4727, 2012.
Trappeniers et al., "Synthesis and in vitro Evaluation of α-GalCer Epimers," *ChemMedChem* 3:1061-1070, 2008.
Tupin et al., CD1d-dependent Activation of NKT Cells Aggravates Atherosclerosis, *The Journal of Experimental Medicine* 199(3):417-422, 2004.
Uchimura et al., "Immunostimulatory Activities of Monoglycosylated α-D-Pyranosylceramides," *Bioorganic & Medicinal Chemistry* 5(12):2245-2249, 1997.
Veerapen et al., "Synthesis and biological activity of α-galactosyl ceramide KRN7000 and galactosyl (α1 2) galactosyl ceramide," *Bioorganic & Medicinal Chemistry Letters* 19:4288-4291, 2009.
Verschueren et al., "Design and Optimization of Tricyclic Phtalimide Analogues as Novel Inhibitors of HIV-1 Integrase," *J. Med. Chem.* 48:1930-1940, 2005.
Weiss et al., "N$^G$-Acyl-argininamides as NPY Y$_1$ receptor antagonists: Influence of structurally diverse acyl substituents on stability and affinity," *Bioorganic & Medicinal Chemistry* 18:6292-6304, 2010.
Widdison et al., "Semisynthetic Maytansine Analogues for the Targeted Treatment of Cancer," *J. Med. Chem.* 49:4392-4408, 2006.
Wilson et al., "Enantioselective Synthesis of a PKC Inhibitor via Catalytic C—H Bond Activation," *Organic Letters* 8(8):1745-1747, 2006.
Wingender et al., "Invariant NKT cells are required for airway inflammation induced by environmental antigens," *The Journal of Experimental Medicine* 208(6):1151-1162, 2011.
Wipf et al., "Expedient Synthesis of the α-C-Glycoside Analogue of the Immunostimulant Galactosylceramide (KRN7000)," *Organic Letters* 8(15):3375-3378, 2006.

(56) References Cited

OTHER PUBLICATIONS

Wu et al., "Avidity of CD1d-ligand-receptor ternary complex contributes to T-helper 1 (Th1) polarization and anticancer efficacy," *PNAS* 108(42):17275-17280, 2011.

Yoshikiyo et al., "Complexation of a disulfide-linked α-cyclodextrin dimer with 1-alkanols," *Journal of Molecular Structure* 891:420-422, 2008.

Zeng et al., "Activation of natural killer T cells in NZB/W mice induces Th-1 type immune responses exacerbating lupus," *Journal of Clinical Investigation* 112(8):1211-1222, 2003.

Zhu, "MMTr as an efficient anomeric S-protecting group for the synthesis of glycosyl thiols," *Tetrahedron Letters* 47:7935-7938, 2006.

\* cited by examiner

SPHINGOGLYCOLIPID ANALOGUES

FIELD OF INVENTION

This invention relates generally to certain sphingoglycolipid analogues, precursors and prodrugs of these compounds, compositions comprising these compounds, including pharmaceutical compositions and adjuvant compositions, processes for preparing the compounds, and methods of treating or preventing diseases or conditions using such compounds, especially diseases or conditions relating to cancer, infection, atopic disorders, autoimmune disease or diabetes.

BACKGROUND

Invariant natural killer T cells (NKT) are a subset of T cells that are implicated in a broad range of diseases. In some circumstances they can enhance the response to infection (Kinjo, Illarionov et al. 2011) and cancer (Wu, Lin et al. 2011) but also possess the ability to suppress autoimmune disease (Hong, Wilson et al. 2001) and allergic disease (Knothe, Mutschler et al. 2011). Activation of NKT cells can also lead to undesirable immune responses as related to allergy (Wingender, Rogers et al. 2011), autoimmunity (Zeng, Liu et al. 2003) and atherosclerosis (Tupin, Nicoletti et al. 2004).

Unlike conventional T cells that are restricted by major histocompatibility complex (MHC) molecules that present peptide antigens, NKT cells are uniquely restricted by CD1d proteins (Bendelac, Savage et al. 2007). CD1d proteins belong to the CD1 family that contains five members, CD1a-e. Like MHC molecules, the CD1 family members all contain an antigen binding region that is flanked by two anti-parallel α-helices that sit above a β-sheet. Unlike MHC molecules, the binding region of the CD1 proteins contain two large hydrophobic binding pockets that are suited to bind lipid antigens rather than peptide-based antigens (Li, Girardi et al. 2010). α-Galactosylceramide (α-GalCer) is the most studied NKT cell antigen and potently activates human and mouse NKT cells (Kawano, Cui et al. 1997). In animal studies, α-GalCer is reported to be useful in the treatment of a number of diseases including cancer (Morita, Motoki et al. 1995; Motoki, Morita et al. 1995) and autoimmune disease (Hong, Wilson et al. 2001). The compound has also been shown to function as a potent vaccine adjuvant in the treatment and prophylaxis of cancer (Silk, Hermans et al. 2004), infectious disease (Li, Fujio et al. 2010) and allergy (Knothe, Mutschler et al. 2011). This adjuvant activity has been attributed to stimulatory interactions between activated NKT cells and dendritic cells (DCs), the most potent antigen-presenting cells in the body. As a consequence, the DCs are rendered capable of promoting strong adaptive immune responses (Fujii, Shimizu et al. 2003; Hermans, Silk et al. 2003).

There is considerable interest in therapeutic vaccines for the treatment of cancer. The aim is to stimulate clonal expansion of T cells within a host that are capable of recognising and killing tumour cells, leaving normal tissues intact. This specificity relies on recognition of unique, tumour-derived, protein fragments presented by MHC molecules on the tumour cell surface. Vaccines used in this context typically involve injection of the defined tumour-associated "tumour antigens", or their peptide fragments, together with immune adjuvants capable of driving an immune response. In the absence of such adjuvants, the opposite outcome may ensue, with the tumour antigens actually being "tolerated" by the immune system rather than provoking tumour rejection. Advances in this therapy are therefore dependent on appropriate combinations of antigen and adjuvant (Speiser and Romero 2010) and how these combinations are presented to the immune system (Black, Trent et al. 2010).

When incorporated into a vaccine, α-GalCer must first be acquired by antigen-presenting cells in the host, and then presented to NKT cells within the local environment (Fujii, Shimizu et al. 2003; Hermans, Silk et al. 2003). This process brings the two cell types into close association, permitting stimulatory signals to be passed from NKT cell to antigen-presenting cell.

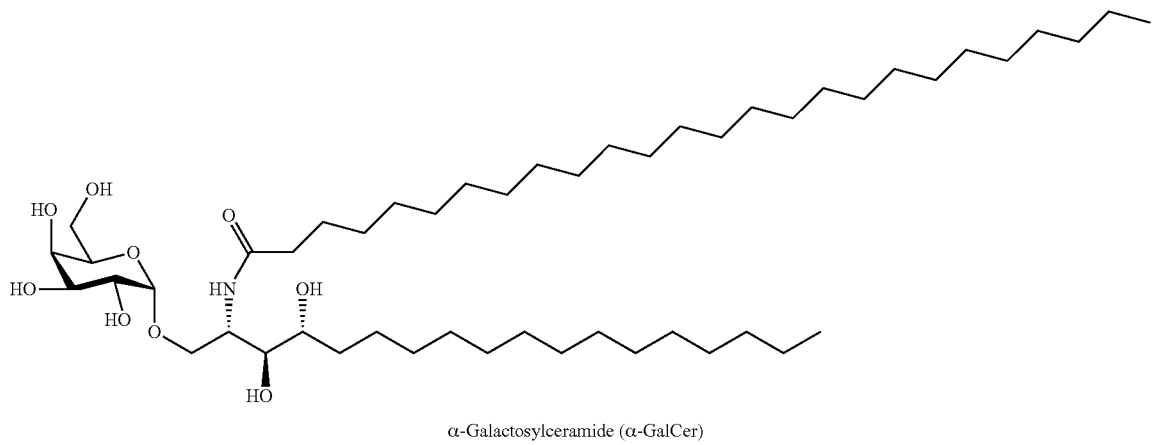

α-Galactosylceramide (α-GalCer)

Although α-GalCer has considerable biological activity it does have limitations such as poor solubility (Ebensen, Link et al. 2007), lack of efficacy in human clinical trials (Giaccone, Punt et al. 2002), promotion of T cell anergy (Parekh, Wilson et al. 2005) and the generation of both Th1 and Th2 cytokines that may contribute to mixed results in model studies.

It is an object of the invention to provide novel compounds or vaccines useful as agents for treating diseases or conditions relating to cancer, infection, autoimmune disease, atopic disorders or cancer, or to at least provide a useful alternative.

Any reference or discussion in relation to prior art publications within this specification does not constitute an admission that such references form part of the common general knowledge in the art in any country or jurisdiction.

Throughout the description and the claims, the words "comprise", "comprising" and the like, are intended to mean in an inclusive sense and not an exclusive or exhaustive sense, that is to say, "including, but not limited to".

STATEMENTS OF INVENTION

In a first aspect, the invention provides a compound of formula (I):

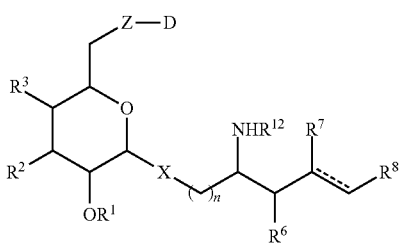

(I)

wherein

Z is S, S—S, SO or $SO_2$;

D is selected from the group:

hydrogen, halogen, hydroxyl, cyano, an optionally substituted alkyl group, an optionally substituted alkenyl group, an optionally substituted alkynyl group, an optionally substituted aralkyl group, an optionally substituted aryl group, a radical of formula D1, a radical of formula D2 and a radical of formula D3;

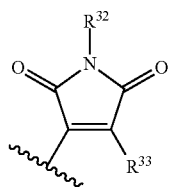

D1

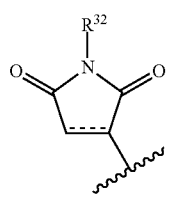

D2

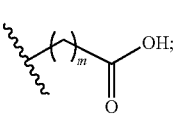

D3 wherein $R^{32}$ is selected from the group consisting of: an optionally substituted alkyl group, an optionally substituted alkenyl group, an optionally substituted alkynyl group and an optionally substituted aryl group; $R^{33}$ is halogen; m is an integer from 1 to 10 and wherein ======= in D2 denotes an optional double bond;

provided that if D is halogen then Z is not S or S—S and provided that if D is cyano then Z is not S—S, SO or $SO_2$ and provided that if D is hydroxyl then Z is not S, S—S or SO;

$R^1$ is H or glycosyl, provided that if $R^1$ is glycosyl then $R^2$ and $R^3$ are both OH;

$R^2$ is selected from the group consisting of H, OH, F and $OR^{10}$; provided that if $R^2$ is H, F or $OR^{10}$, then $R^1$ is H, $R^3$ is OH;

$R^3$ is selected from the group consisting of H, OH, F and $OR^{10}$; provided that if $R^3$ is H, F or $OR^{10}$, then $R^1$ is H, $R^2$ is OH;

$R^6$ is OH or H;

$R^7$ is OH or H; wherein when $R^7$ is H, $R^8$ is $C_1$-$C_{15}$ alkyl and X is O, ======= denotes an optional double bond linking the carbon adjacent to $R^7$ with the carbon adjacent to $R^8$;

$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

X is O, $CH_2$ or S; wherein, when X is $CH_2$ then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is OH and $R^7$ is H, and $R^8$ is $C_{13}H_{27}$ and the stereochemistry at carbon atoms 2 and 3 is (2S, 3S); or when X is S then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R); or $R^6$ is OH and $R^7$ is H and the stereochemistry at the carbon atoms 2 and 3 is (2S, 3S);

n is 1 when X is O or S; or n is 0 or 1 when X is $CH_2$;

or a pharmaceutically acceptable salt thereof.

Preferably, the compound of formula (I) is a compound of formula (I.1)

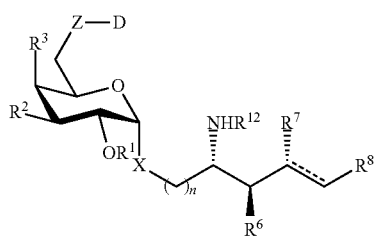

(I.1)

wherein X, Z, D, $R^1$, $R^2$, $R^3$, $R^6$, $R^7$, $R^8$, $R^{10}$, $R^{12}$, $R^{32}$, m and n are all as defined above.

Preferably the stereochemistry of the 6-membered sugar ring of formula (I) is α-D-galacto.

Preferably, n in formula (I) is 1, the stereochemistry of the 6-membered sugar ring of formula (I) is α-D-galacto, $R^6$ is OH and $R^7$ is OH. It is further preferred that n in formula (I) is 1, the stereochemistry of the 6-membered sugar ring of formula (I) is α-D-galacto, $R^6$ is OH, $R^7$ is OH and the stereochemistry at carbon atoms 2, 3 and 4 is (2S, 3S, 4R).

Alternatively preferably, n in formula (I) is 0, X is $CH_2$, the stereochemistry of the 6-membered sugar ring of formula (I) is α-D-galacto, $R^6$ is OH and $R^7$ is OH. It is further preferred that n in formula (I) is 0, the stereochemistry of the 6-membered sugar ring of formula (I) is α-D-galacto, $R^6$ is OH, $R^7$ is OH and the stereochemistry at carbon atoms 2, 3 and 4 is (2S, 3S, 4R).

Preferably, in formula (I) when X is O, $R^6$ is OH, $R^7$ is H, $R^8$ is $C_1$-$C_{15}$ alkyl and ----- is a double bond linking the carbon adjacent to $R^7$ with the carbon adjacent to $R^8$, then the stereochemistry at the carbon atoms 2, 3 is (2S, 3S).

Preferably Z in formula (I) is S. Alternatively, preferably Z is SO. Alternatively, preferably Z is $SO_2$.

Preferably X in formula (I) is O.

Preferably $R^{12}$ in formula (I) is $C_{26}$ acyl. More preferably $R^{12}$ is a $C_{26}$ acyl group which is unsubstituted.

Preferably $R^8$ in formula (I) is $C_{10}$ to $C_{14}$ alkyl, most preferably $C_{13}$ alkyl.

Preferably $R^1$ in formula (I) is H.

It is also preferred that $R^2$ in formula (I) is OH. More preferably $R^1$ is H and $R^2$ is OH.

Preferably $R^3$ in formula (I) is OH.

Preferably $R^6$ in formula (I) is OH.

Preferably $R^7$ in formula (I) is OH. More preferably $R^7$ is OH and $R^6$ is OH. Still more preferably $R^7$ is OH, $R^6$ is OH and X is O.

Alternatively it is preferred that $R^7$ in formula (I) is H and $R^6$ is OH.

Preferably $R^8$ in formula (I) is $C_1$-$C_{15}$ alkyl. More preferably $R^8$ is $C_1$-$C_{15}$ alkyl having a straight or branched carbon chain containing no double bonds, triple bonds, oxygen atoms or aryl groups. Still more preferably $R^8$ is $C_{13}$ alkyl having a straight carbon chain containing no double bonds, triple bonds, oxygen atoms or aryl groups. Still more preferably $R^8$ is $C_1$-$C_{15}$ alkyl, $R^7$ is OH and $R^6$ is OH. Still more preferably $R^8$ is $C_1$-$C_{15}$ alkyl, $R^7$ is OH, $R^6$ is OH and X is O.

Preferably $R^{12}$ in formula (I) is acyl having a straight carbon chain from 6 to 30 carbon atoms long. More preferably $R^{12}$ is $C_{26}$ acyl. More preferably $R^{12}$ is $C_{26}$ acyl having a straight carbon chain containing no double bonds, triple bonds, oxygen atoms, aryl groups and which is unsubstituted. More preferably X is O and $R^{12}$ is acyl having a straight carbon chain from 6 to 30 carbon atoms long. Still more preferably $R^{12}$ is unsubstituted acyl having a straight carbon chain from 6 to 30 carbon atoms long.

Preferably any halogen in formula (I) is bromine, fluorine or chlorine.

Preferably $R^{33}$ is a bromo group.

Preferably D in formula (I) is an alkyl group, more preferably methyl, ethyl, propyl or butyl group. Most preferably D is t-butyl group. It is also preferred that D is an alkyl group substituted with an azide group.

Alternatively preferably D in formula (I) is hydrogen.

Alternatively preferably D in formula (I) is an alkenyl or alkynyl group, more preferably butenyl or butynyl group.

Alternatively preferably D in formula (I) is an aralkyl group, more preferably D is a benzyl group optionally substituted with one or more halogen or amino groups. Alternatively preferably D is a 2-picolinyl group.

Alternatively preferably D in formula (I) is an aryl group, more preferably phenyl or pyridyl group.

Alternatively preferably D in formula (I) is a chloro group.

Alternatively preferably D in formula (I) is a hydroxyl group.

Alternatively preferably D in formula (I) is a cyano group.

Alternatively preferably D in formula (I) is a radical of formula D1

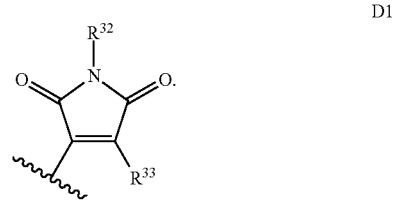

Alternatively preferably D in formula (I) is a radical of formula D2

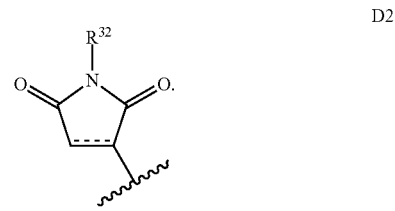

Alternatively preferably D in formula (I) is a radical of a radical of formula D3

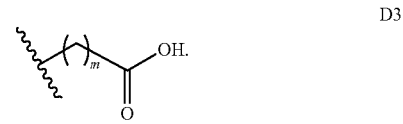

Preferably the compound of formula (I) is a compound of formula (I.2)

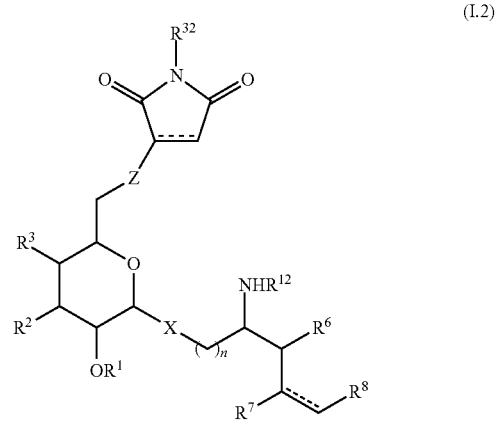

wherein X, Z, $R^1$, $R^2$, $R^3$, $R^6$, $R^7$, $R^8$, $R^{10}$, $R^{12}$, $R^{32}$ and n are all as defined above.

Alternatively, preferably the compound of formula (I) is a compound of formula (I.3)

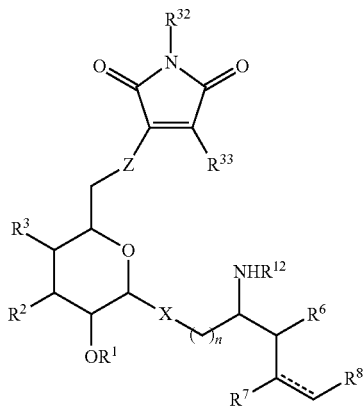

(I.3)

wherein X, Z, $R^1$, $R^2$, $R^3$, $R^6$, $R^7$, $R^8$, $R^{10}$, $R^{12}$, $R^{32}$, $R^{33}$ and n are all as defined above.

Alternatively, preferably the compound of formula (I) is a compound of formula (I.4)

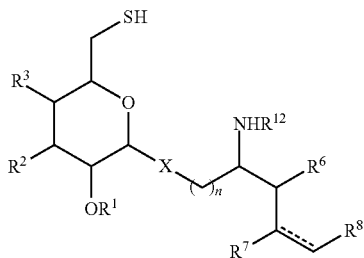

(I.4)

wherein X, $R^1$, $R^2$, $R^3$, $R^6$, $R^7$, $R^8$, $R^{10}$, $R^{12}$ and n are all as defined above.

In another aspect, the invention provides a compound of formula (II)

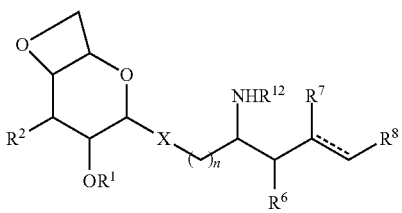

(II)

wherein X, $R^1$, $R^6$, $R^7$, $R^8$, $R^{10}$, $R^{12}$ and n are all as defined above;

$R^2$ is selected from the group consisting of H, OH, F and $OR^{10}$; provided that if $R^2$ is H, F or $OR^{10}$, then $R^1$ is H;

or a pharmaceutically acceptable salt thereof.

In still another aspect, the invention provides a compound of formula (VI)

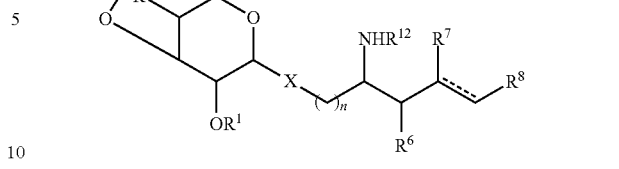

(VI)

wherein X, $R^1$, $R^6$, $R^7$, $R^8$, $R^{10}$, $R^{12}$ and n are all as defined above;

$R^3$ is selected from the group consisting of H, OH, F and $OR^{10}$; provided that if $R^3$ is H, F or $OR^{10}$, then $R^1$ is H;

or a pharmaceutically acceptable salt thereof.

In another aspect, the invention provides a compound of formula (IV)

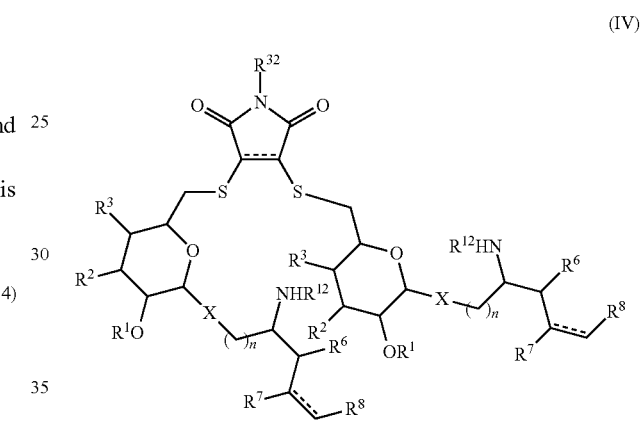

(IV)

wherein X, $R^1$, $R^2$, $R^3$, $R^6$, $R^7$, $R^8$, $R^{10}$, $R^{12}$, $R^{32}$, $R^{33}$ and n are all as defined above; and wherein ===== denotes an optional double bond;

or a pharmaceutically acceptable salt thereof.

In another aspect, the invention provides a compound of formula (V)

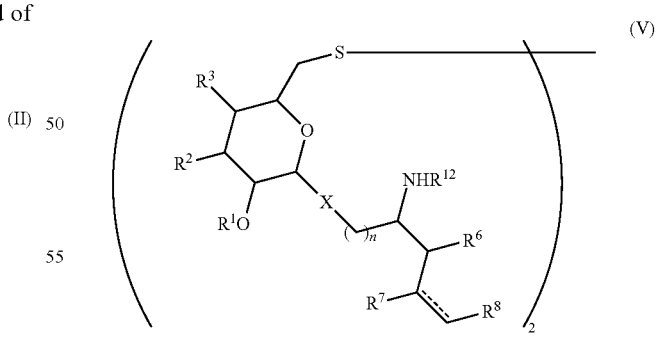

(V)

wherein X, $R^1$, $R^2$, $R^3$, $R^6$, $R^7$, $R^8$, $R^{10}$, $R^{12}$ and n are all as defined above;

or a pharmaceutically acceptable salt thereof.

Preferably the stereochemistry of the 6-membered sugar rings of formula (IV) or formula (V) is α-D-galacto.

Preferably, each n in formula (II), (IV), (V) or (VI) is 1, the stereochemistry of the 6-membered sugar rings of formula (II), (IV), (V) or (VI) is α-D-galacto, each $R^6$ is OH and each $R^7$ is OH. It is further preferred that each n in formula (II), (IV), (V) or (VI) is 1, the stereochemistry of the 6-membered sugar rings of formula (II), (IV), (V) or (VI) is α-D-galacto, each $R^6$ is OH, each $R^7$ is OH and the stereochemistry at carbon atoms 2, 3 and 4 is (2S, 3S, 4R).

Alternatively preferably, each n in formula (II), (IV), (V) or (VI) is 0, each X is $CH_2$, the stereochemistry of the 6-membered sugar rings of formula (II), (IV), (V) or (VI) is α-D-galacto, each $R^6$ is OH and each $R^7$ is OH. It is further preferred that each n in formula (II), (IV), (V) or (VI) is 0, the stereochemistry of the 6-membered sugar rings of formula (II), (IV), (V) or (VI) is α-D-galacto, each $R^6$ is OH, each $R^7$ is OH and the stereochemistry at carbon atoms 2, 3 and 4 is (2S, 3S, 4R).

Preferably, in formula (II), (IV), (V) or (VI) when each X is O, each $R^6$ is OH, each $R^7$ is H, each $R^8$ is $C_1$-$C_{15}$ alkyl and there is a double bond linking each carbon adjacent to $R^7$ with each carbon adjacent to $R^8$, then the stereochemistry at the carbon atoms 2, 3 is (2S, 3S).

In still another aspect, the invention provides a compound of formula (I.5)

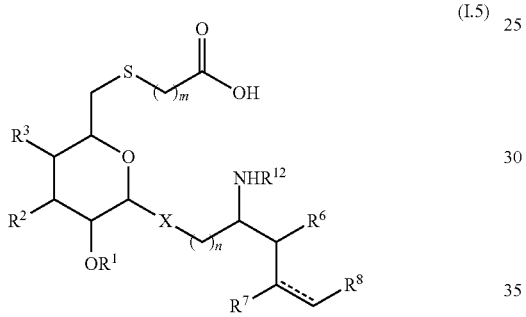

(I.5)

wherein $R^1$ is H or prot;
$R^2$, $R^3$, $R^6$ and $R^7$ are each independently OH or Oprot;
wherein prot is a protecting group;
and X, $R^8$, $R^{10}$, $R^{12}$, $R^{32}$, m and n are all as defined above.

Preferably Z is S. Alternatively, preferably Z is SO. Alternatively, preferably Z is $SO_2$.

Preferably X is O.

Preferably $R^{12}$ is $C_{26}$ acyl. More preferably $R^{12}$ is a $C_{26}$ acyl group which is unsubstituted.

Preferably $R^8$ is $C_{10}$ to $C_{14}$ alkyl, most preferably $C_{13}$ alkyl.

Preferably $R^1$ is H.

It is also preferred that $R^2$ is OH. More preferably $R^1$ is H and $R^2$ is OH.

Preferably $R^3$ is OH.

Preferably $R^6$ is OH.

Preferably $R^7$ is OH. More preferably $R^7$ is OH and $R^6$ is OH. Still more preferably $R^7$ is OH, $R^6$ is OH and X is O.

Alternatively it is preferred that $R^7$ is H and $R^6$ is OH.

Preferably $R^8$ is $C_1$-$C_{15}$ alkyl. More preferably $R^8$ is $C_1$-$C_{15}$ alkyl having a straight or branched carbon chain containing no double bonds, triple bonds, oxygen atoms or aryl groups. Still more preferably $R^8$ is $C_{13}$ alkyl having a straight carbon chain containing no double bonds, triple bonds, oxygen atoms or aryl groups. Still more preferably $R^8$ is $C_1$-$C_{15}$ alkyl, $R^7$ is OH and $R^6$ is OH. Still more preferably $R^8$ is $C_1$-$C_{15}$ alkyl, $R^7$ is OH, $R^6$ is OH and X is O.

Preferably $R^{12}$ is acyl having a straight carbon chain from 6 to 30 carbon atoms long. More preferably $R^{12}$ is $C_{26}$ acyl. More preferably $R^{12}$ is $C_{26}$ acyl having a straight carbon chain containing no double bonds, triple bonds, oxygen atoms, aryl groups and which is unsubstituted. More preferably X is O and $R^{12}$ is acyl having a straight carbon chain from 6 to 30 carbon atoms long. Still more preferably $R^{12}$ is unsubstituted acyl having a straight carbon chain from 6 to 30 carbon atoms long.

Preferably prot in formula (I.5) is benzyl or acetyl.

Preferably any halogen is bromine, fluorine or chlorine.

Preferably $R^{33}$ is a bromo group.

Preferably the compound of formula (I) is selected from the group consisting of:

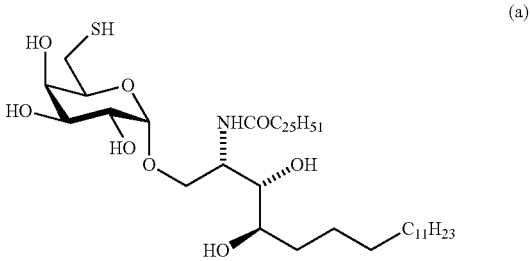

(a)

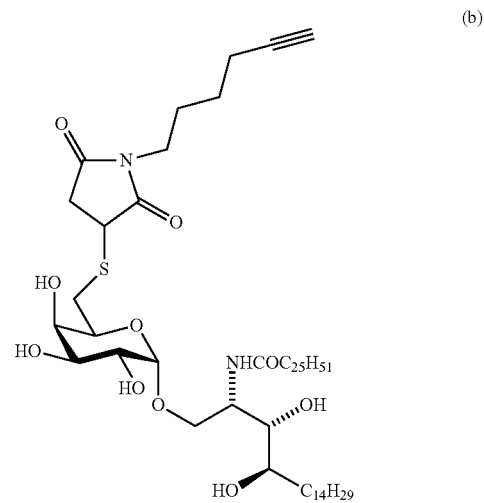

(b)

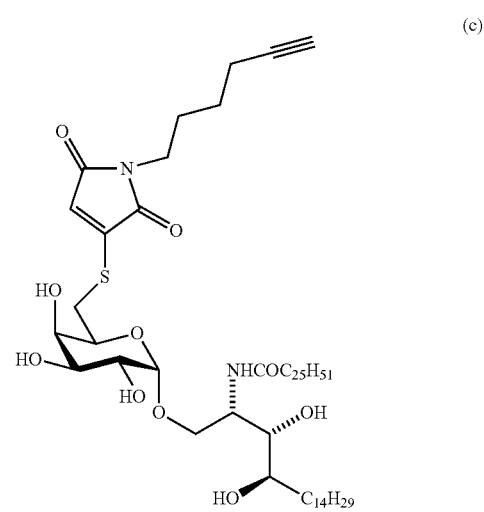

(c)

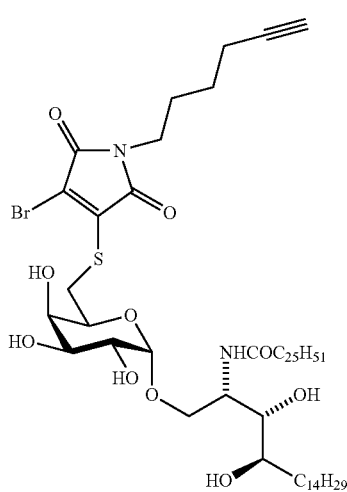
(d)
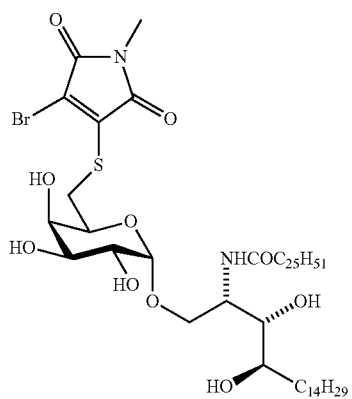
(e)
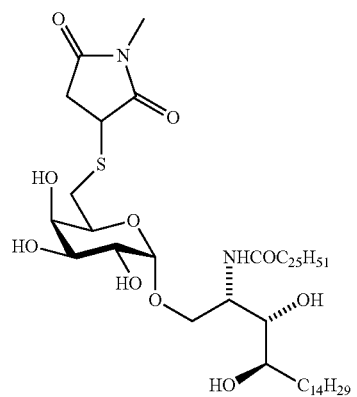
(g)
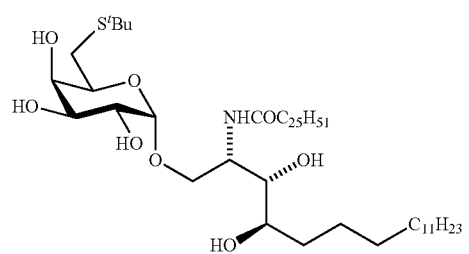
(h)
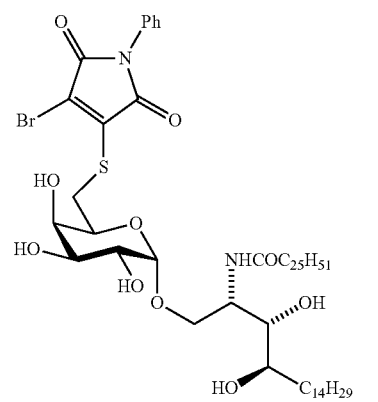
(j)
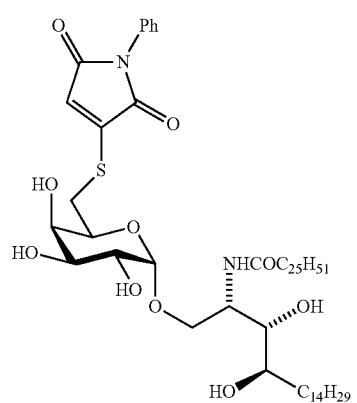
(k)

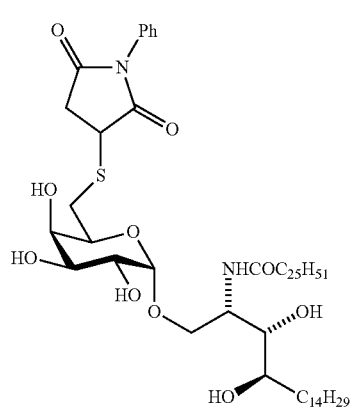
(m)
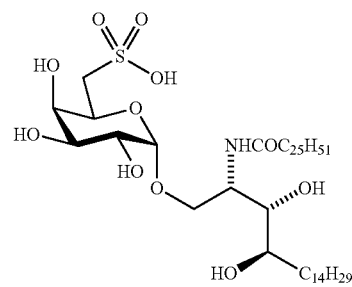
(n)
wherein hal is a halogen
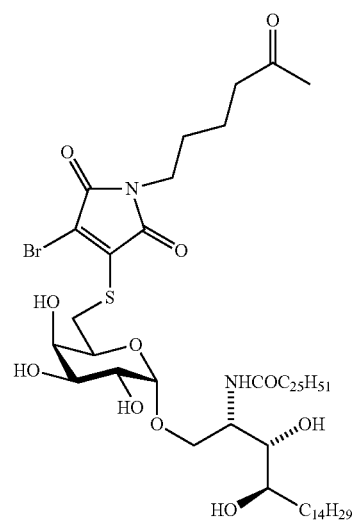
(o)
(p)
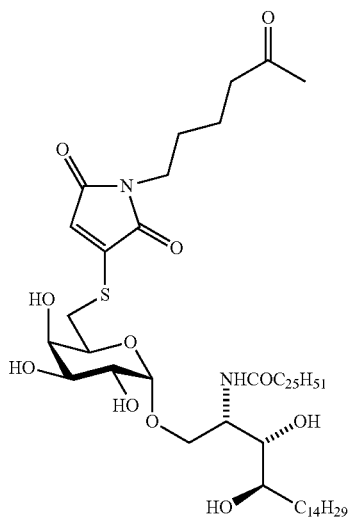
(q)
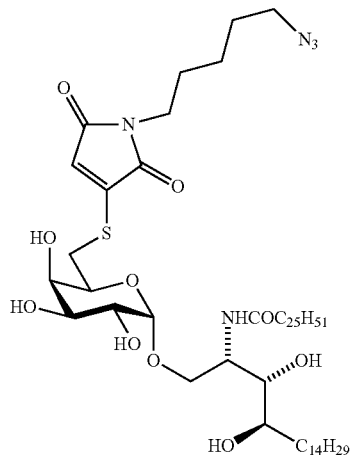
(r)
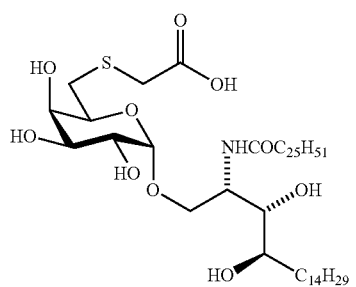
(s)

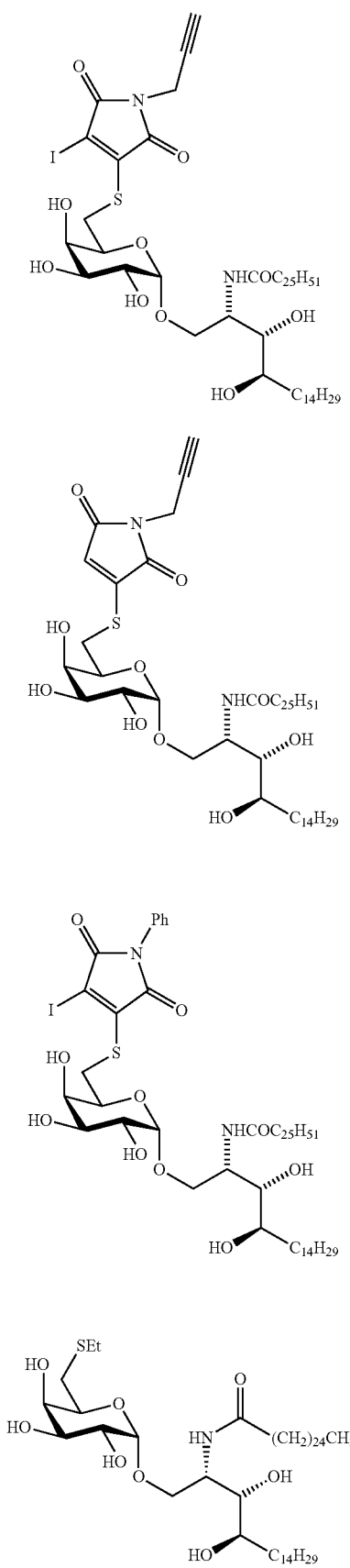
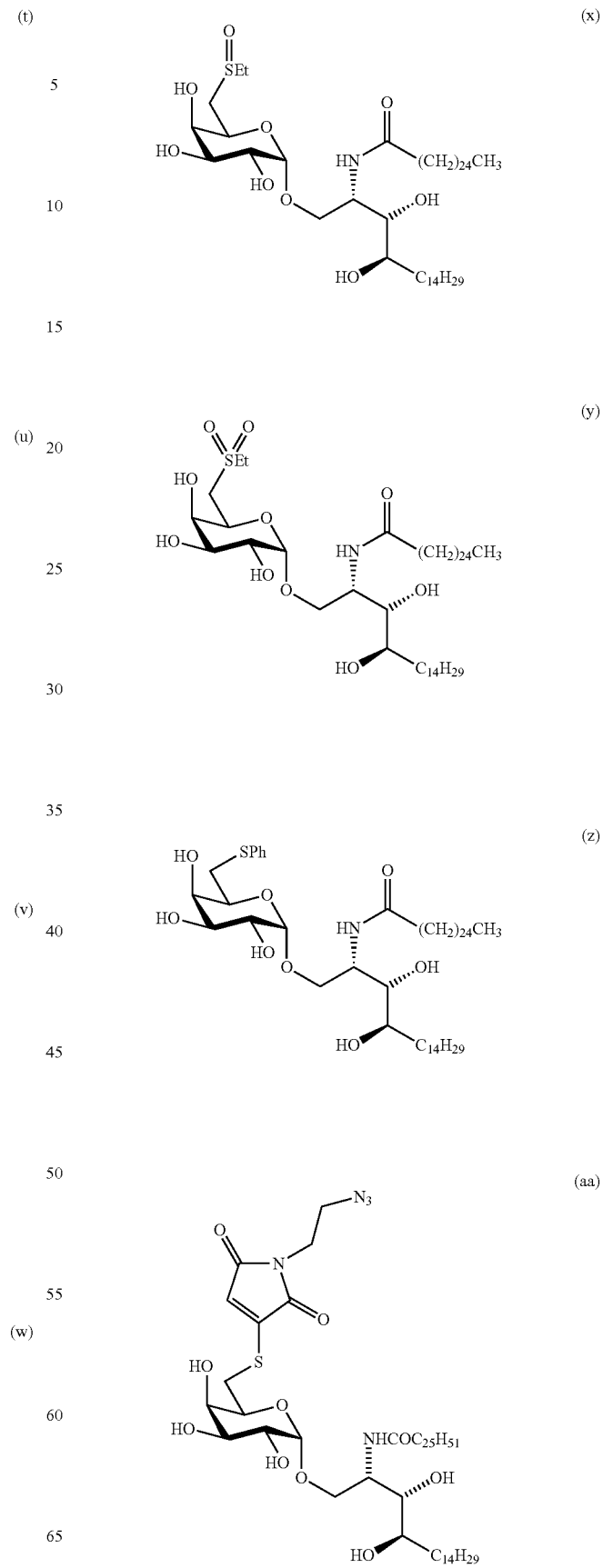

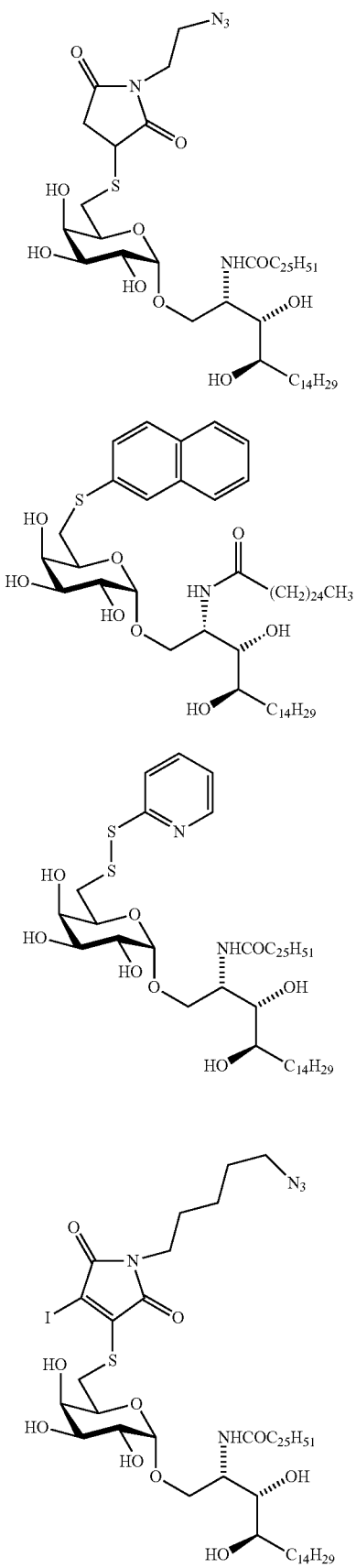
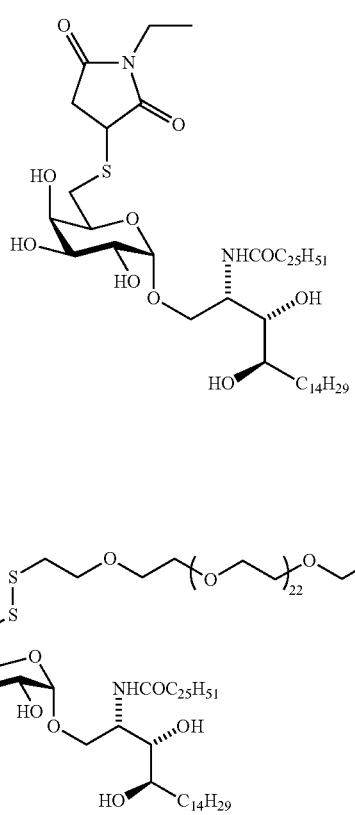
Preferably the compound of formula (II) is:
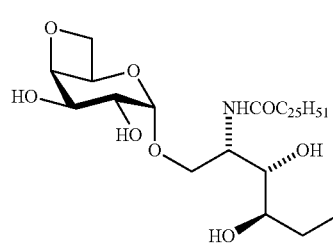
Preferably the compound of formula (VI) is:
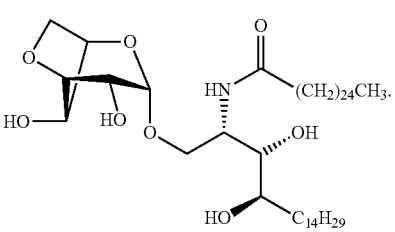
Preferably the compound of formula (IV) is selected from the group consisting of:

(ee)
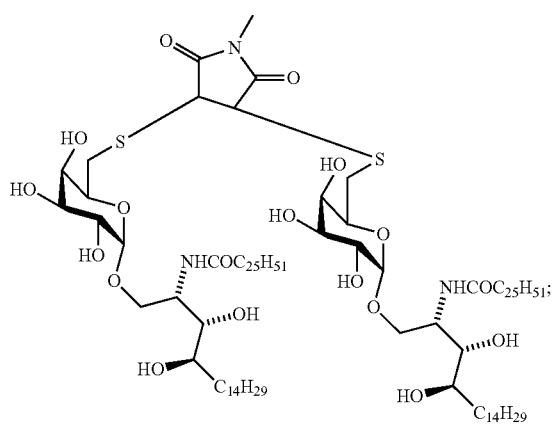

(ff)
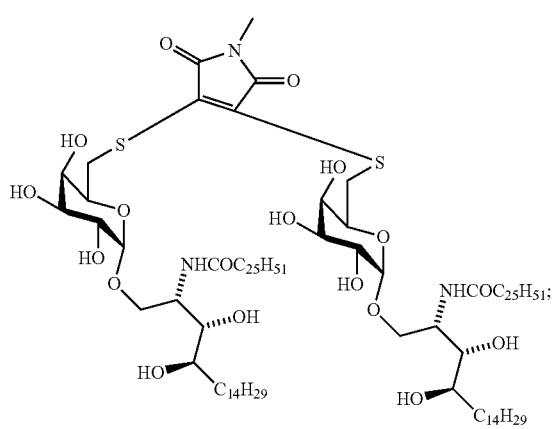

(gg)
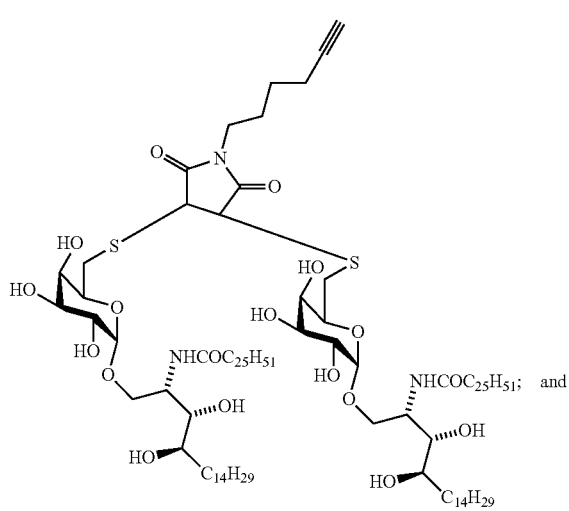

-continued (hh)
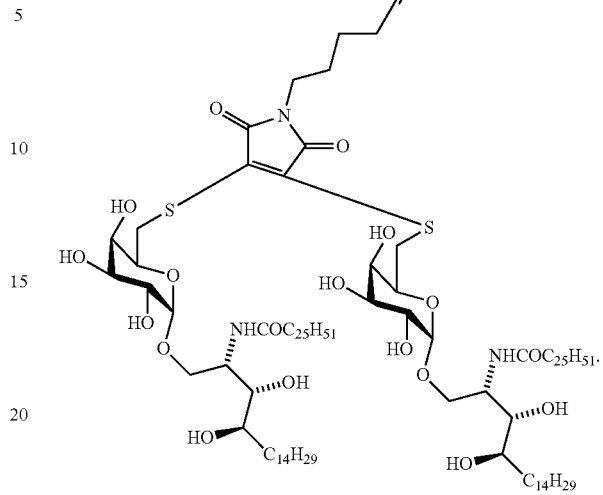

Preferably the compound of formula (V) is:

(jj)

In another aspect the invention provides a pharmaceutical composition comprising a pharmaceutically effective amount of a compound of formula (I), (II), (IV), (V) or (VI) and optionally a pharmaceutically acceptable carrier.

In another aspect the invention provides an immunogenic composition comprising a compound of formula (I), (II), (IV), (V) or (VI) and a pharmaceutically acceptable diluent and optionally an antigen.

In another aspect the invention provides a vaccine comprising a compound of formula (I), (II), (IV), (V) or (VI) and a pharmaceutically acceptable diluent and optionally an antigen.

In another aspect the invention provides a compound of formula (I), (II), (IV), (V) or (VI), and optionally an antigen, for use in the preparation of a vaccine.

The antigen may be a bacterium such as *Bacillus* Calmette-Guérin (BCG), a virus or peptide. Examples of suitable antigens include, but are not limited to, Wilms' Tumor 1 (WT1) (Li, Oka et al. 2008), tumor-associated antigen MUC1 (Brossart, Heinrich et al. 1999), latent membrane protein 2 (LMP2) (Lu, Liang et al. 2006), HPV E6E7 (Davidson, Faulkner et al. 2004), NY-ESO-1 (Karbach, Gnjatic et al. 2010), tyrosinase-related protein (Trp)-2 (Noppen, Levy et al. 2000; Chang 2006, Bernard, Ventresca et al. 2010), survivin (Schmitz, Diestelkoetter et al. 2000; Friedrichs, Siegel et al. 2006; Ciesielski, Kozbor et al. 2008), MART-1 (Bettinotti, Kim et al. 1998; Jager, Hohn et al. 2002), CEA691 (Huarte, Sarobe et al. 2002) and glycoprotein 100 (gp100) (Levy, Pitcovski et al. 2007).

In still another aspect the invention provides a compound of formula (I), (II), (IV), (V) or (VI) in combination with at least one other compound, e.g. a second drug compound, e.g. an anti-bacterial agent or an anti-cancer agent such as Vemurafenib (PLX4032), Imatinib or Carfilzomib.

In yet another aspect the invention provides the use of a compound of formula (I), (II), (IV), (V) or (VI) as a medicament.

In another aspect the invention provides the use of a compound of formula (I), (II), (IV), (V) or (VI) for treating or preventing an infectious disease, an atopic disorder, an autoimmune disease, diabetes or cancer.

In another aspect the invention provides the use of a pharmaceutical composition comprising a pharmaceutically effective amount of a compound of formula (I), (II), (IV), (V) or (VI), for treating or preventing an infectious disease, an atopic disorder, an autoimmune disease, diabetes or cancer.

In another aspect the invention provides a compound of formula (I), (II), (IV), (V) or (VI) for use in the manufacture of a medicament.

In another aspect the invention provides a pharmaceutical composition for treating or an infectious disease, an atopic disorder, an autoimmune disease, diabetes or cancer, comprising a compound of formula (I), (II), (IV), (V) or (VI).

In another aspect the invention provides the use of a compound of formula (I), (II), (IV), (V) or (VI) in the manufacture of a medicament for treating or preventing an infectious disease, an atopic disorder, an autoimmune disease, diabetes or cancer.

In another aspect the invention provides the use of a compound of formula (I), (II), (IV), (V) or (VI) in combination with at least one other compound, e.g. a second drug compound, e.g. an anti-bacterial agent or an anti-cancer agent such as Vemurafenib (PLX4032), Imatinib or Carfilzomib for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering a pharmaceutically effective amount of a compound of formula (I), (II), (IV), (V) or (VI) to a patient requiring treatment.

In another aspect the invention provides a method of treating or preventing an infectious disease, an atopic disorder, an autoimmune disease, diabetes or cancer comprising administering to a patient a pharmaceutically effective amount of a compound of formula formula (I), (II), (IV), (V) or (VI) in combination with at least one other compound, e.g. a second drug compound, e.g. an anti-bacterial agent or an anti-cancer agent such as Vemurafenib (PLX4032), Imatinib or Carfilzomib. The compound of formula (I) and the other compound may be administered separately, simultaneously or sequentially.

The diseases or conditions include cancer, e.g. melanoma, prostate, breast, lung, glioma, lymphoma, colon, head and neck and nasopharyngeal carcinoma (NPV); infectious diseases, e.g. viral infections such as HIV, bacterial infections; atopic diseases; or autoimmune diseases.

In another aspect the invention provides a method of modifying an immune response in a patient, comprising administering a compound of formula (I), (II), (IV), (V) or (VI), and optionally an antigen, to the patient.

Preferably the patient is a human.

The compound of formula (I), (II), (IV), (V) or (VI) may be selected from the group consisting of compounds (a) to (h), (j), (k) and (m) to (x) as defined above.

Compounds of formula (I), (II), (IV), (V) or (VI) are described herein as "compounds of the invention". A compound of the invention includes a compound in any form, e.g. in free form or in the form of a salt or a solvate.

It will be appreciated that any of the sub-scopes disclosed herein, e.g. with respect to X, Z, D, $R^1$, $R^2$, $R^3$, $R^6$, $R^7$, $R^8$, $R^{10}$, $R^{12}$, $R^{32}$, $R^{33}$, m and n may be combined with any of the other sub-scopes disclosed herein to produce further sub-scopes.

DETAILED DESCRIPTION

Definitions

The term "cancer" and like terms, refer to a disease or condition in a patient that is typically characterised by abnormal or unregulated cell growth. Cancer and cancer pathology can be associated, for example, with metastasis, interference with the normal functioning of neighbouring cells, release of cytokines or other secretory products at abnormal levels, cell proliferation, tumour formation or growth, suppression or aggravation of inflammatory or immunological response, neoplasia, premalignancy, malignancy, invasion of surrounding or distant tissues or organs, such as lymph nodes, etc. Particular cancers are described in detail herein. Examples include lung, glioma, lymphoma, colon, head and neck and nasopharyngeal carcinoma (NPV), melanoma, chronic myelogenous leukemia (CML), myeloma, prostate, breast, glioblastoma, renal cell carcinoma, hepatic cancers.

"Infections" and like terms refer to diseases or conditions of a patient comprising internal and/or external growth or establishment of microbes. Microbes include all living forms too small to be seen by eye, including bacteria, viruses, fungi, and protozoa. Included are aerobic and anaerobic bacteria, and gram positive and gram negative bacteria such as cocci, bacilli, spirochetes, and mycobacteria. Particular infectious disorders are described in detail herein. Examples include bacterial or viral infections.

"Atopic disorders" and like terms refer to a disease or condition of a patient that is typically characterized by an abnormal or up-regulated immune response, for example, an IgE-mediated immune response, and/or Th2-cell immune response. This can include hypersensitivity reactions (e.g., Type I hypersensitivity), in particular, as associated with allergic rhinitis, allergic conjunctivitis, atopic dermatitis, and allergic (e.g. extrinsic) asthma. Typically, atopic disorders are associated with one or more of rhinorrhea, sneezing, nasal congestion (upper respiratory tract), wheezing, dyspnea (lower respiratory tract), itching (e.g., eyes, skin), nasal turbinate edema, sinus pain on palpation, conjunctival hyperemia and edema, skin lichenification, stridor, hypotension, and anaphylaxis. Particular atopic disorders are described in detail herein.

The term "patient" includes human and non-human animals. Non-human animals include, but are not limited to birds and mammals, in particular, mice, rabbits, cats, dogs, pigs, sheep, goats, cows, horses, and possums.

"Treatment" and like terms refer to methods and compositions to prevent, cure, or ameliorate a medical disease, disorder, or condition, and/or reduce at least a symptom of such disease or disorder. In particular, this includes methods and compositions to prevent or delay onset of a medical disease, disorder, or condition; to cure, correct, reduce, slow, or ameliorate the physical or developmental effects of a medical disease, disorder, or condition; and/or to prevent, end, reduce, or ameliorate the pain or suffering caused by the medical disease, disorder, or condition.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The term "alkyl" means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include both straight- and branched-chain alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "lower alkyl" means any saturated hydrocarbon radical having from 1 to 6 carbon atoms and is intended to include both straight- and branched-chain alkyl groups.

Any alkyl group may optionally be substituted with one or more substituents selected from the group consisting of azide; amino; hydroxy; acyl, e.g. acetyl; and halogen, e.g. fluorine.

The term "alkylene" means a diradical corresponding to an alkyl group and includes any $C_r$ $C_{25}$, $C_1$-$C_{20}$, $C_1$-$C_{15}$, $C_1$-$C_{10}$, or $C_1$-$C_6$ alkylene group, and is intended to include both straight- and branched-chain groups. Examples of alkylene groups include: methylene (—$CH_2$—) group, ethylene [—$CH_2$—$CH_2$—] group, n-propylene [(—$CH_2$—)$_3$] group, n-butylene group [(—$CH_2$—)$_4$] and n-pentylene group [(—$CH_2$—)$_5$].

Any alkylene group may optionally be substituted with one or more substituents selected from the group consisting of hydroxy and halogen, e.g. fluorine.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, and is intended to include both straight- and branched-chain alkenyl groups. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "lower alkenyl" means any hydrocarbon radical having at least one double bond, and having from 2 to 6 carbon atoms, and is intended to include both straight- and branched-chain alkenyl groups.

Any alkenyl group may optionally be substituted with one or more substituents selected from the group consisting of alkoxy, hydroxy and halogen, e.g. fluorine.

The term "alkynyl" means any hydrocarbon radical having at least one carbon-carbon triple bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkynyl group, and is intended to include both straight- and branched-chain alkynyl groups. Examples of alkynyl groups include: ethynyl group, n-propynyl and n-butynyl group.

The term "lower alkynyl" means any hydrocarbon radical having at least one double bond, and having from 2 to 6 carbon atoms, and is intended to include both straight- and branched-chain alkenyl groups.

Any alkynyl group may optionally be substituted with one or more substituents selected from the group consisting of alkoxy, hydroxy and halogen, e.g. fluorine.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group and isoxazolyl group.

The term "aralkyl" means an aryl group which is attached to an alkylene moiety, where aryl is as defined above. Examples include benzyl group and 2-picolinyl group.

Any aryl or aralkyl group may optionally be substituted with one or more substituents selected from the group consisting of alkyl, amino, halogen, cyano, dialkylamino, amide (both N-linked and C-linked: —NHC(O)R and —C(O)NHR), nitro, alkoxy, acyloxy and thioalkyl.

The term "alkoxy" means an OR group, where R is alkyl as defined above. The term "lower alkoxy" means an OR group, where R is "lower alkyl" as defined above.

The term "alkenyloxy" means an OR' group, where R' is alkenyl as defined above.

The term "aryloxy" means an OR" group, where R" is aryl as defined above.

The term "acyl" means C(═O)R'" group, where R'" is alkyl as defined above, which optionally incorporates one or more double bonds, one or more triple bonds, and/or one or more optionally substituted arylene groups and wherein the carbon chain is optionally substituted.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise specified, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "glycosyl" means a radical derived from a cyclic monosaccharide, disaccharide or oligosaccharide by removal of the hemiacetal hydroxy group. Examples include α-D-glucopyranosyl, α-D-galactopyranosyl, β-D-galactopyranosyl and α-D-2-deoxy-2-acetamidogalactopyranosyl.

The term "amide" includes both N-linked (—NHC(O)R) and C-linked (—C(O)NHR) amides.

The term "prot" means a protecting group and includes any suitable protecting group. Suitable protecting groups are described in T. W. Greene and P. G. M. Wutz (1991) "Protective groups in organic synthesis" (New York, N.Y., John Wily and Sons, Inc.). Examples include, but are not limited to, methyl, ethyl, TMS, pyridyl, but most preferably acetyl, benzyl and benzoyl. Cyclic protecting groups such as acetals and dialkylsilylenes can be used to protect diols. Examples of these include benzylidene acetals and di-t-butylsilylene.

The term "pharmaceutically acceptable salt" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate and undecanoate.

Those skilled in the art will appreciate that compounds of formula (I) and other compounds disclosed herein that contain a thiol group can exist as the corresponding disulfide, described herein as compounds of formula (V). The invention is intended to cover both the thiol and the disulfide forms of the compounds disclosed herein. For example, the compound of example 2.4 can exist as the thiol form:

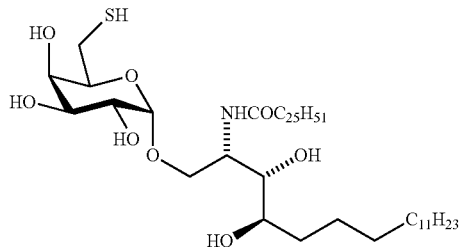

or as the disulfide form:

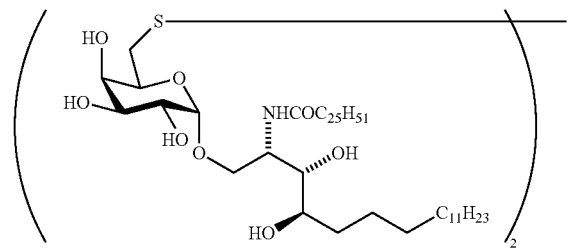

For the purposes of the invention, any reference to the disclosed compounds includes all possible formulations, configurations, and conformations, for example, in free form (e.g., as a free acid or base), in the form of salts or hydrates, in the form of isomers (e.g., cis/trans isomers), stereoisomers such as enantiomers, diastereomers and epimers, in the form of mixtures of enantiomers or diastereomers, in the form of racemates or racemic mixtures, or in the form of individual enantiomers or diastereomers. Specific forms of the compounds are described in detail herein.

The Compounds of the Invention

The compounds of the invention, particularly those exemplified, are useful as pharmaceuticals, particularly for the treatment or prevention of diseases or conditions relating to infection, atopic disorders, autoimmune disease or cancer. The compounds of the invention are also useful as vaccine adjuvants. For example, a compound of the invention may be formulated in a vaccine together with one or more antigens.

Compounds of the invention are potent immune stimulators having a similar in vivo activity as compared to α-GalCer (FIGS. 1 and 2). Surprisingly, NKT cell activation by certain compounds of the invention induces the production of different cytokine profiles in vivo, as compared to α-GalCer (FIG. 3). In particular, injection of α-GalCer induces the peak production of IL-4 levels in the serum at 2-3 hours, followed by high levels of IL-12p70 peaking at 6 hours, and IFN-γ peaking after 12 hours. Although compounds of the invention induce a similar temporal cytokine pattern, the profile is significantly different, especially for CN161 and CN154, with a higher ratio of IFN-γ/IL-4. Compounds of the invention (e.g. CN161) possess potent vaccine adjuvant activity in a therapeutic tumour (B16 melanoma) challenge model when injected with protein antigen (FIG. 4). Compounds of the invention (e.g. CN161) induce potent antigen-specific cytotoxicity and cause delayed tumour growth when injected with a long peptide from the tumour-associated antigen TRP-2 (Bernard, Ventresca et al. 2010) (FIGS. 5 and 6). When injected with a long peptide from the model antigen OVA, compounds of the invention and α-GalCer show similar anti-tumour activity (FIG. 7). Compounds of the invention (e.g. CN161) show anti-leukemia activity either alone or when combined with a cellular vaccine (FIG. 8A). Surprisingly, in this assay, α-GalCer is not active when injected alone (FIG. 8B). In culture with peripheral blood mononuclear cells from human blood, compounds of the invention (e.g. CN161) are able to induce the proliferation of iNKT cells (FIG. 9).

Thus, the invention provides the surprising benefit that compounds can be "tuned" to induce the production of different cytokines in vivo and therefore may be used to target specific disease. The invention also provides an alternative NKT agonist that has a convenient functional group modification and in some circumstances better activity, as compared to α-GalCer.

The compounds of the invention are useful in both free base form and in the form of salts and/or solvates which would be understood to those skilled in the art.

The carbon atoms of the acyclic moiety of the compounds of formula (I), (II), (IV), (V) and (VI) are labelled as shown below.

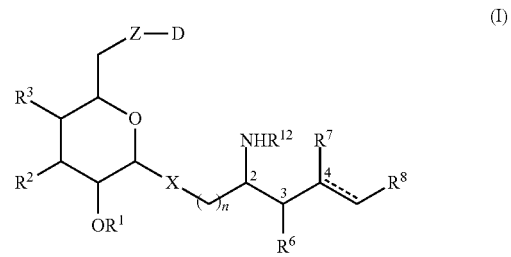

Synthesis of Compounds of the Invention

The compounds of the invention may be synthesised according to the following general methods. When X=O compounds of formula XX, or their precursors, can be synthesized by glycosylation of a suitably protected donor VII with a suitably protected acceptor VIII. Compounds of formula III' could then be accessed following suitable protecting group manipulation to allow introduction of a leaving group (LG) at position 6 of the sugar, for example halogen, OTs, OMs, OTf (Scheme 1).

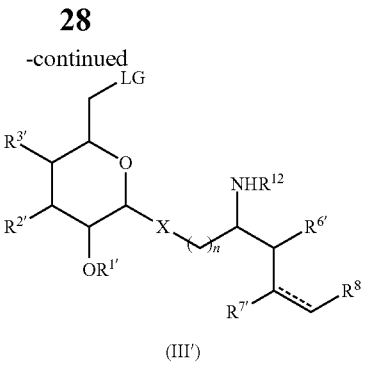

(III')

Scheme 1

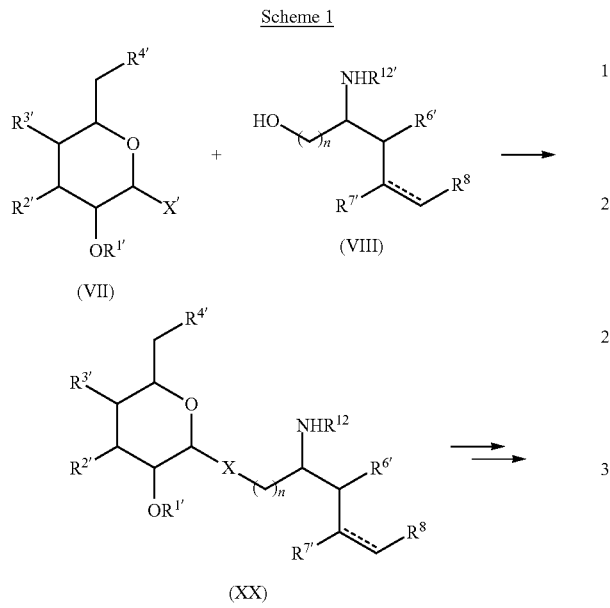

A wide variety of donors of formula VII ($R^{1'}$=a protecting group, prot, e.g. Bn or Ac, $R^{2'}=R^{3'}=R^{4'}$=Oprot, e.g. where Oprot is OBn or OAc) have been used in the synthesis of α-GalCer analogues, which allows variation of groups $R^{1'}$-$R^{4'}$ and the stereochemistry of these groups. For example, compounds where $R^{3'}$=H, F can be accessed from 2,3,6-tri-O-benzyl phenylthio glycoside via deoxygenation or treatment with DAST (Scheme 2). Compounds where $R^{2'}$=H can be synthesized from donor (VIIc) and compounds where $R^{2'}$=F can be obtained from donor (VIId). Methods for the synthesis of donors where $R^{1'}$ is glycosyl (Veerapen, Brigl et al. 2009), $R^{2'}$ or $R^{3'}$ is O-glycosyl (Kawano, Cui et al. 1997), and $R^{2'}$ or $R^{3'}$ is either H or F (Raju, Castillo et al. 2009) have been reported.

Scheme 2

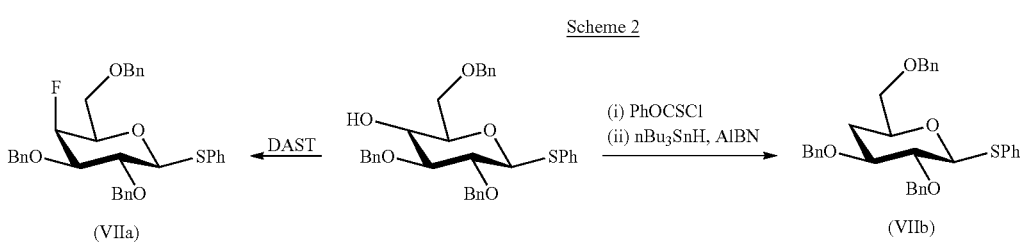

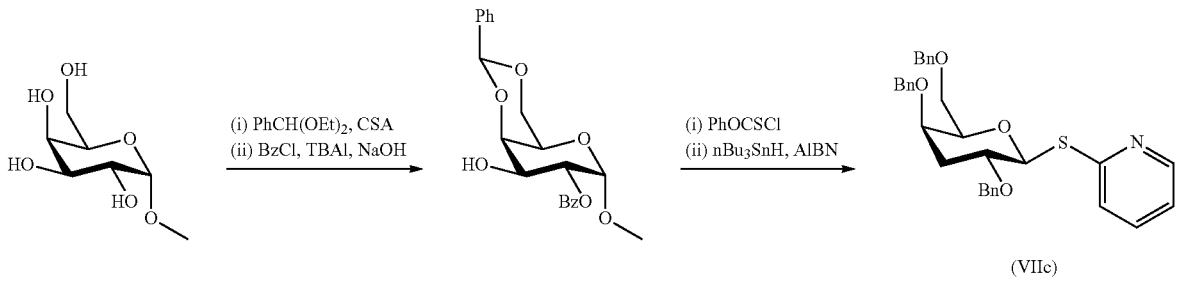

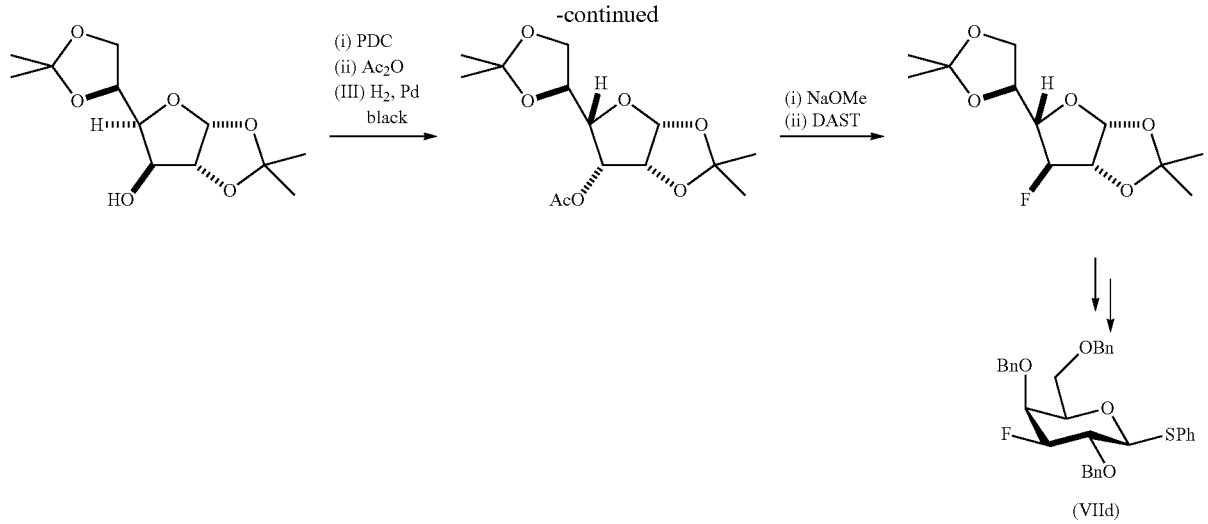

An equally large variety of acceptors have also been employed. For example, all 8 stereoisomers of a protected phytospingosine acceptor have been synthesized in an approach that also allows modification of the group $R^8$ (Park, Lee et al. 2008; Baek, Seo et al. 2011). Furthermore, 3-deoxy (Baek, Seo et al. 2011) and 4-deoxy phytosphingosine (Morita, Motoki et al. 1995; Howell, So et al. 2004; Du, Kulkarni et al. 2007) derivatives have also been described. Combination of these acceptors with various donors leads to protected α-GalCer derivatives which are transformed, by literature methods referenced above, to the unprotected α-GalCer analogues, which comprise the starting materials (III) (where X is O) described herein.

For example, when $R^8 = C_{14}H_{29}$ various acceptors (VIII) can be synthesized from D-ribo-phytoshingosine by conversion of the amine group to an azide followed by protecting group manipulation (Trappeniers, Goormans et al. 2008) and, for (VIIIb) and (VIIIe) (Scheme 3) deoxygenation with tin hydride (Raju, Castillo et al. 2009) to reveal acceptors (VIIIa-e). (Scheme 3). In this approach $R^{12}$ can be installed after glycosylation by routine azide reduction and amide bond-formation methodology (Atherton, Fox et al. 1978; Fields and Noble 1990).

Scheme 3

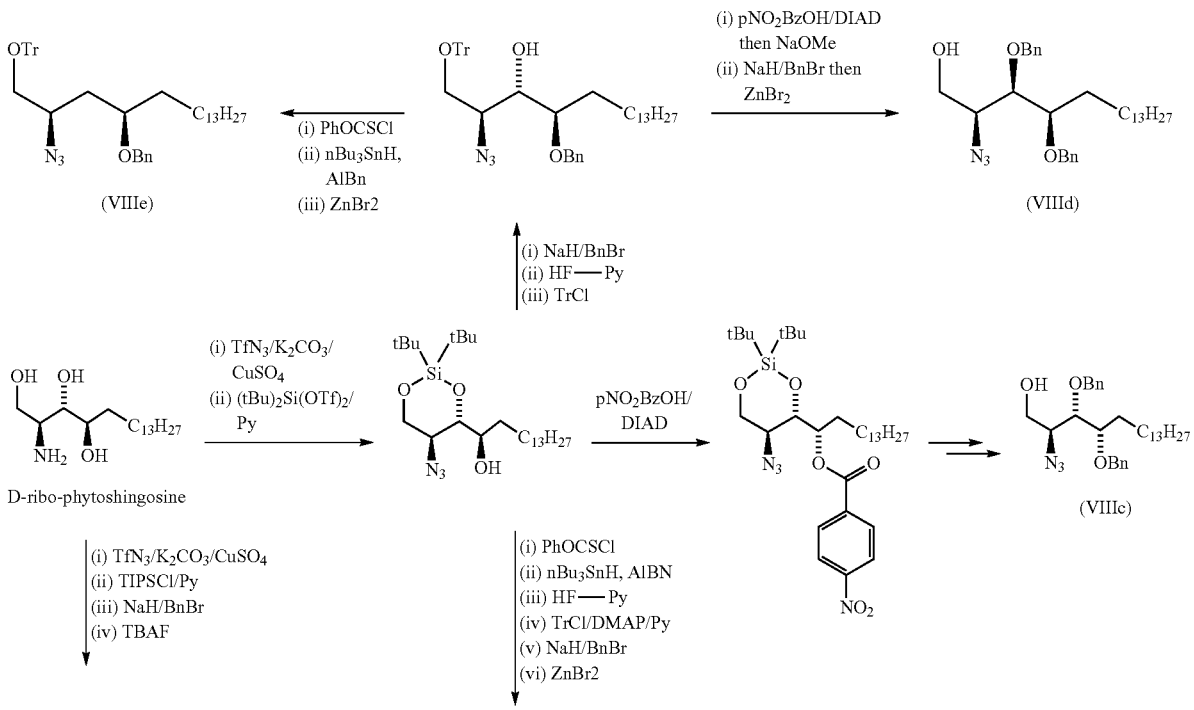

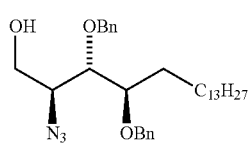

(VIIIa)

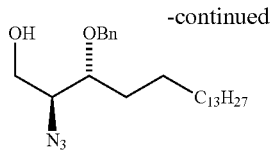

(VIIIb)

After glycosylation of the acceptor with the donor the resulting adduct XX can be further manipulated to introduce a suitable LG at position 6 of the sugar using standard methods. Installation of a sulfur-containing moiety at position 6 of the sugar can be achieved by displacement of LG with a nucleophilic source of sulfur such as M-SC(O)CH$_3$ or M-S-Alkyl, or M-S-Aryl where M is a metal for example Li, Na, K. (Scheme 4). For example tosylate 2 may be derived from known diol 1 (Lee at al 2006) by a regioselective reaction (primary hydroxyl verses secondary). The tosylate 2 or alternate LG compound could be used to synthesize compounds where R$^3$=H, F or glycosyl by the combination of methods mentioned above—for example glycosylation of trichloroacetimate donor (VIIf) with acceptors (VIIIa-e) would afford compounds 1' that could be manipulated further to afford compounds of general formula I.

For glycosylation products (XX) in which X is CH$_2$ and R$^7$ is OH, syntheses have been described (Chen, Schmieg et al. 2004; Lu, Song et al. 2006; Wipf and Pierce 2006; Pu and Franck 2008). For glycosylation products (XX) where X is CH$_2$ and R$^7$ is H, these are synthesized according to reported methods (Chen, Schmieg et al. 2004) using sphingosine as the starting material in place of phytosphingosine. For glycosylation products (XX) in which X is S or CH$_2$, syntheses have been described (Dere and Zhu 2008; O'Reilly and Murphy 2011).

Scheme 4

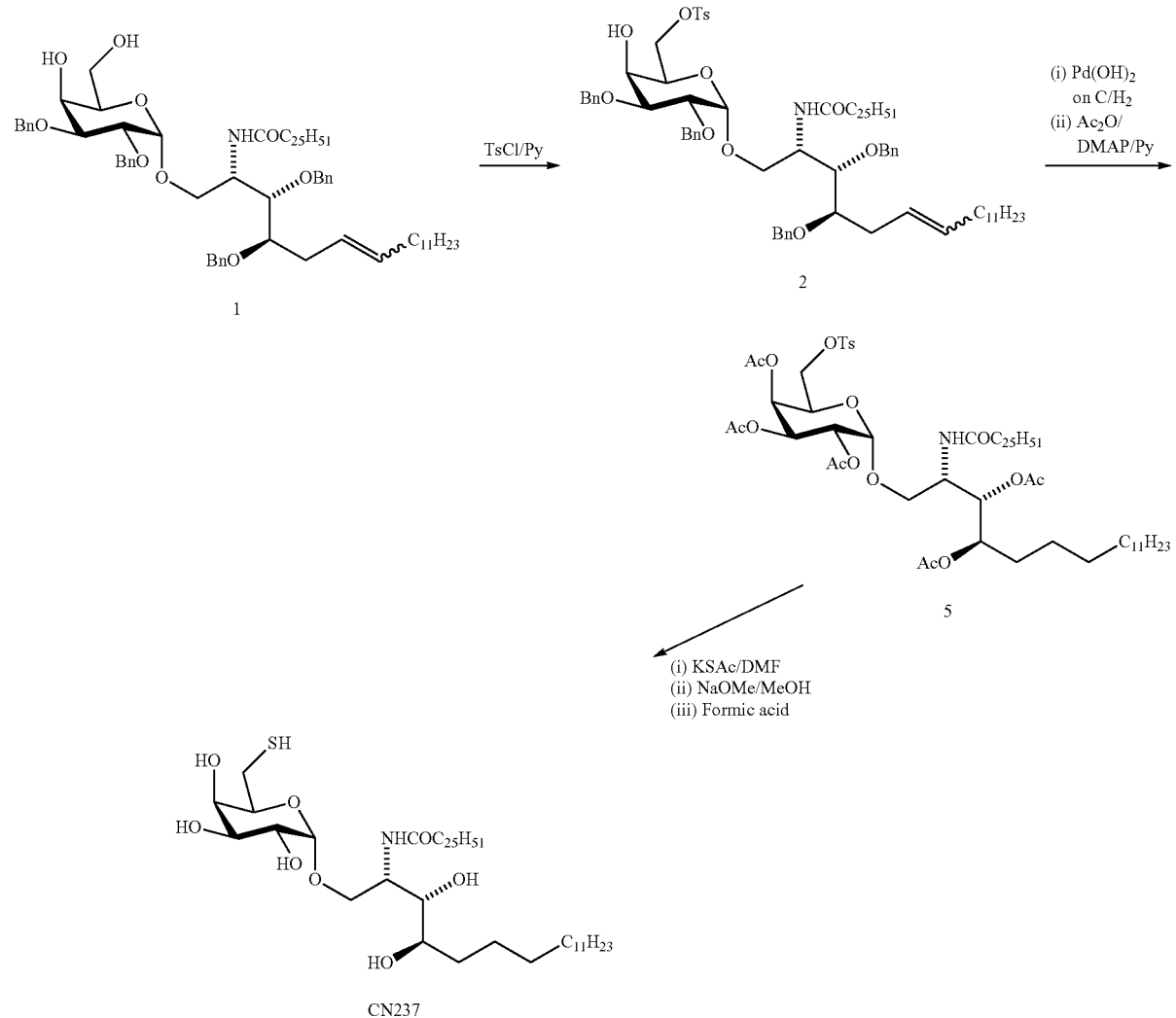

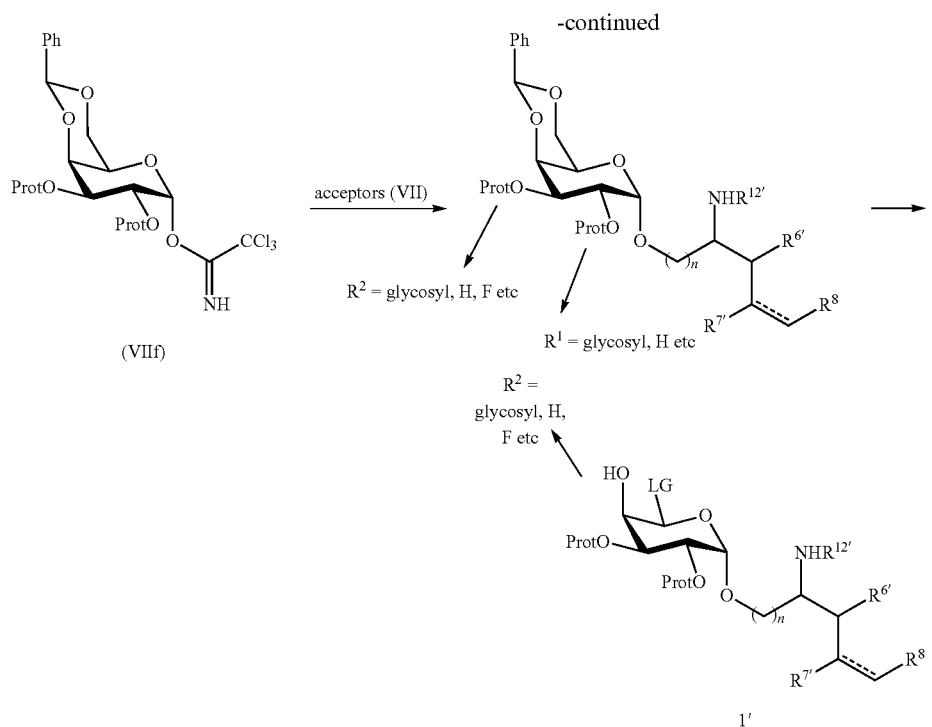

General Method (1) for the Synthesis of Compounds of Formula (I) where Z is S (wherein Z=S; D=hydrogen, an optionally substituted alkyl group, an optionally substituted alkenyl group, an optionally substituted alkynyl group, an optionally substituted aralkyl group, an optionally substituted aryl group, an optionally substituted aryl group, a radical of formula D1, a radical of formula D2 or a radical of formula D3.)

Scheme 5

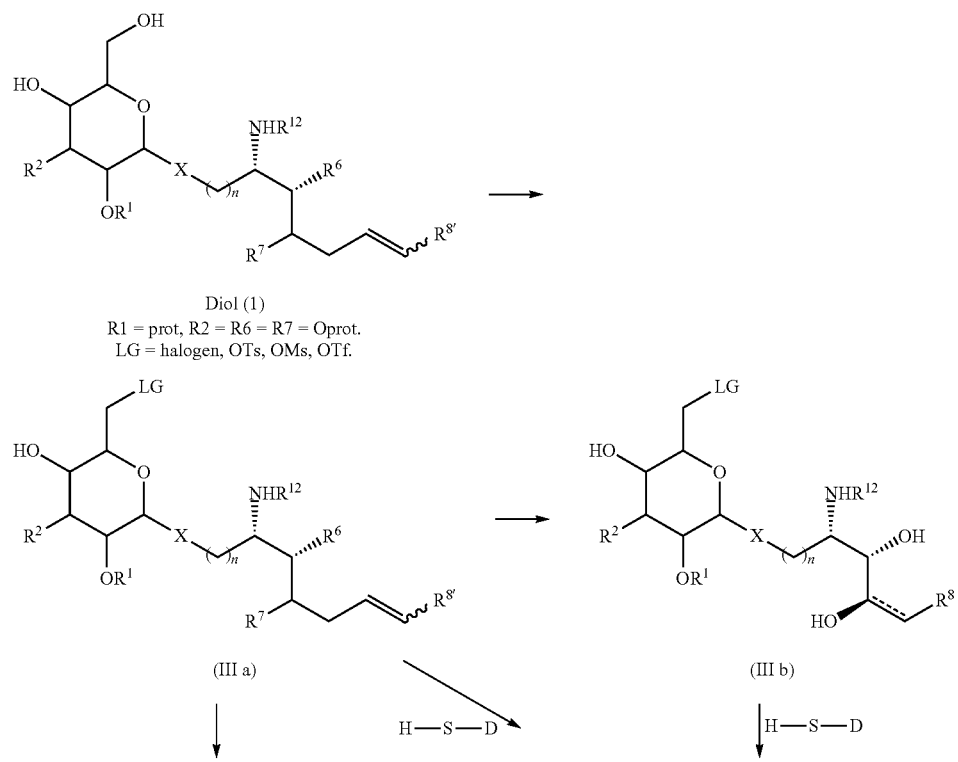

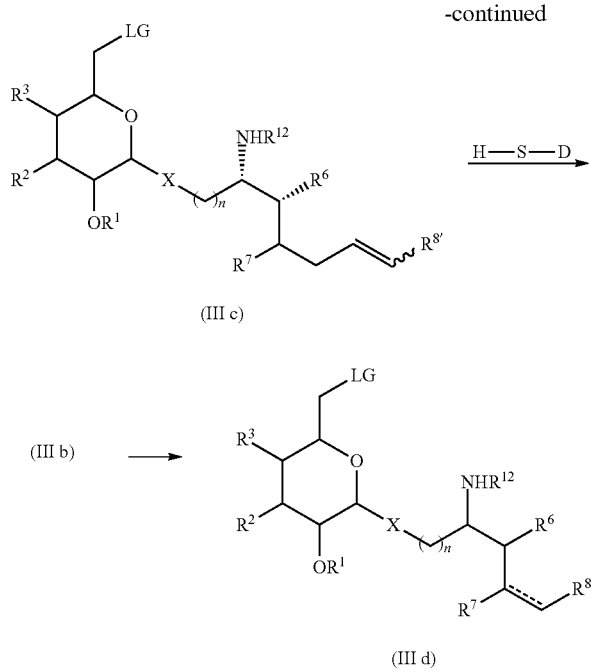

(III c)

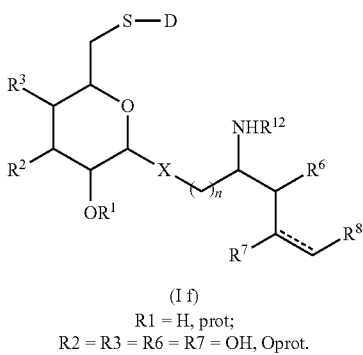

(I f)
R1 = H, prot;
R2 = R3 = R6 = R7 = OH, Oprot.

(III b) →

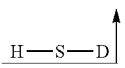

(III d)

Starting materials discussed in these General Methods are produced from known diol 1 (which is prepared as described in Lee, A., K. J. Farrand, et al. (2006). "Novel synthesis of alpha-galactosyl-ceramides and confirmation of their powerful NKT cell agonist activity." *Carbohyd Res* 341(17): 2785-2798). In the initial step, the primary alcohol at C-6 of the pyranose ring in diol 1 is converted into an appropriate leaving group (III a; LG=halogen, OTs, OMs, OTf) using routine chemical transformations (Scheme 1). Where LG=halogen, this can alternatively be accessed via the corresponding tolylate (OTs), mesylate (OMs) or triflate (OTf) derivative by a displacement reaction. Compound III a can then be reacted with a suitable thiol reagent (H—S-D) to access compounds of formula I f directly. Alternatively, III a can be deprotected (III b) using methods compatible with the leaving group present and subsequently reacted with the thiol reagent of choice to generate deprotected I f ($R^1$=H, $R^2$=$R^3$=$R^6$=$R^7$=OH).

In a situation where it is necessary to protect the free 4-OH of III a before introducing the thiol, the 4-hydroxyl can be suitably protected with standard protection chemistry, as illustrated in III c, before accessing I f by similar methods as detailed herein. Suitable protecting groups include benzyl, acetate, benzoyl and TMS.

Should the protecting groups in III a be incompatible with the chemistry required for introducing the thiol, it may be appropriate to access III b and then re-protect the compound with a more appropriate protecting group, such as benzyl, acetate or benzoyl to yield III d. Reaction of III d with the desired thiol reagent would again generate I f.

For the synthesis of III a (where LG=halogen), triphenyl phosphine (1.0-3.0 equiv) and carbon tetrabromide (1.0-3.0 equiv) are added to a solution of diol 1 (1.0 equiv) stirring in a suitable solvent under an inert atmosphere at an appropriate temperature (0° C.-RT) (Chen, Xu et al. 2012). Once the reaction is complete (TLC) the mixture is filtered, concentrated and purified by chromatography on the appropriate solid phase (e.g. silica gel, C4, and/or C18 silica).

Alternative halogenating reagents include iodine, sodium iodide, TBAI, while appropriate solvents include THF, DMF, $CH_2Cl_2$, toluene, pyridine, acetone and mixtures thereof. It may also be necessary to heat the reaction and/or add a base such as NaH, imidazole, $NEt_3$ or DIPEA.

An alternative synthesis of III a (where LG=tosylate) involves adding tosyl chloride (1.0-3.0 equiv) to diol 1 (1.0 equiv) stirring in a suitable solvent at an appropriate temperature (0° C.-RT). The reaction is monitored and heated if necessary (RT-reflux) with the addition of more reagent (tosyl chloride) until the reaction is considered to be complete (TLC). Following this, the mixture is diluted with an appropriate solvent, water is added and the organic layer concentrated. Purification of the crude material is achieved by chromatography on the appropriate solid phase (e.g. silica gel, C4, and/or C18 silica). Suitable solvents include THF, $Et_2O$, DMF, toluene, pyridine, $CH_2Cl_2$, MeCN and 1,4-dioxane. It may also aid the reaction to include a base such as $NEt_3$, DMAP or 2,6-lutidine Compounds III b are prepared from compounds III a by routine deprotection methods known to those skilled in the art, e.g. where $R^1$=Bn and $R^2$=$R^6$=$R^7$=OBn, hydrogenation using an appropriate catalyst can be utilised.

Similarly, the formation of compounds III c from III a, and III d from compounds III b can be achieved using standard protection chemistry well known to those skilled in the art, e.g. per-acetylating III b using $Ac_2O$ and pyridine to generate III d (where $R^1$=Ac and $R^2$=$R^3$=$R^6$=$R^7$=OAc).

For the preparation of compounds of formula I f, a mixture of compound of type III (1.0 equiv), thiol (H—S-D where D is as defined above for General Method (1); 1.0-10.0 equiv) and NaH (1.0-2.0 equiv) is stirred in a suitable solvent at an appropriate temperature (RT-reflux). More thiol reagent can be added until the reaction is essentially complete (TLC). After quenching the reaction with water, the mixture is washed and the organic phases concentrated. The resulting residue is purified by chromatography on the appropriate solid phase (e.g. silica gel, C4, and/or C18 silica). Alternative bases include NaOH, NaH, $NEt_3$, DBU, $K_2CO_3$, $KHCO_3$, while suitable solvents include THF, DMF, toluene, MeCN, EtOH, water or mixtures thereof. Appropriate thiolating reagents also include potassium thioacetate, thiourea and potassium thiocyanate.

Generation of the final deprotected compounds of type I f is achieved by standard deprotection chemistry known to those skilled in the art.

General Method (2) for the Synthesis of Compounds of Formula (I) where Z is Substituted Thiol (wherein Z=S; D=an optionally substituted alkyl group, an optionally substituted alkenyl group, an optionally substituted alkynyl group, an optionally substituted aralkyl group, an optionally substituted aryl group, an optionally substituted aryl group, a radical of formula D1, a radical of formula D2 or a radical of formula D3.)

Scheme 6

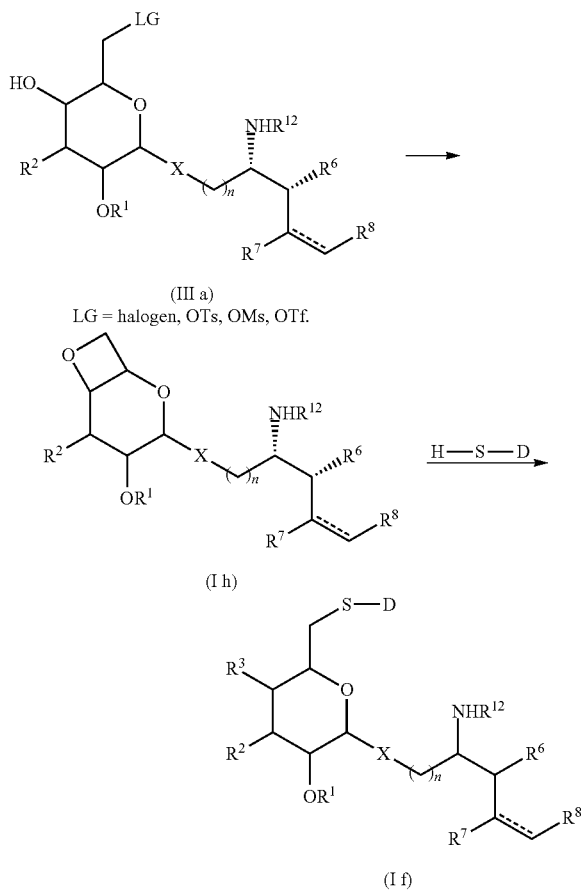

R1 = H, prot;
R2 = R3 = R6 = R7 = OH, Oprot.

An alternative route to I f proceeds via oxetane I h. Ring opening of the oxetane ring may require the use of an organometallic reagent and optionally a Bronsted or Lewis acid.

Oxetane I h can be accessed by adding sodium hydride (1.0-3.0 equiv) to a solution of III a (1.0 equiv) stirring in a suitable solvent at an appropriate temperature (0° C.-RT) under an inert atmosphere. The reaction is monitored and heated if necessary (RT-reflux) until deemed to be complete (TLC). The reaction is then quenched, diluted with solvent and washed. Concentration of the organic phase gives the crude material which is purified by chromatography on the appropriate solid phase (e.g. silica gel, C4, and/or C18 silica). Alternative bases include NaOH, DBU, NEt$_3$ and DIPEA, while appropriate solvents can be Et$_2$O, MeOH, THF, DMF, DME, acetone, pyridine and mixtures thereof.

A solution of the appropriate organometallic (1.0-3.0 equiv) in a suitable solvent is added dropwise to a stirred solution of oxetane I h (1.0 equiv) and thiol (H—S—D; 1.0-3.0 equiv) dissolved in an appropriate solvent at room temperature. After complete addition the solution is stirred for another hour and heated to reflux for a period of a few hours (Bach, Kather et al. 1998). The reaction is quenched, diluted with additional solvent, filtered and concentrated. The crude material is purified by chromatography on the appropriate solid phase (e.g. silica gel, C4, and/or C18 silica). The organometallic reagent can be an organo-lithium or an organo-grignard reagent, while appropriate solvents can be Et$_2$O, THF and DME. The reaction may require the use of a suitable Bronsted or Lewis acid such as BF$_3$.OEt$_2$, AlCl$_3$ or Ti(OR)$_4$ (R=alkyl), and/or high temperatures.

Generation of the deprotected versions of compounds I h and I f is achieved by standard deprotection chemistry known to those skilled in the art.

General Method (3) for the Synthesis of Compounds of Formula (I) where Z is Disulfide (wherein Z=S—S; D=an optionally substituted alkyl group, an optionally substituted alkenyl group, an optionally substituted alkynyl group, an optionally substituted aralkyl group, an optionally substituted aryl group, an optionally substituted aryl group, a radical of formula D1, a radical of formula D2 or a radical of formula D3.)

Scheme 7

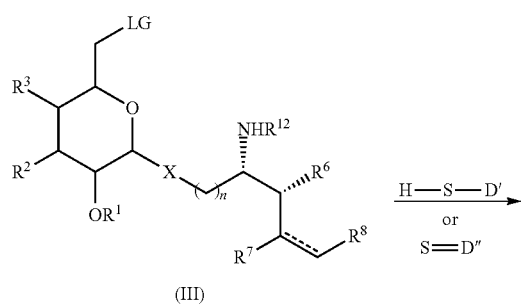

LG = halogen, OTs, OMs, OTf.
D' = alkyl, acyl, nitrile, aryl.
D" = C(NH$_2$)$_2$.

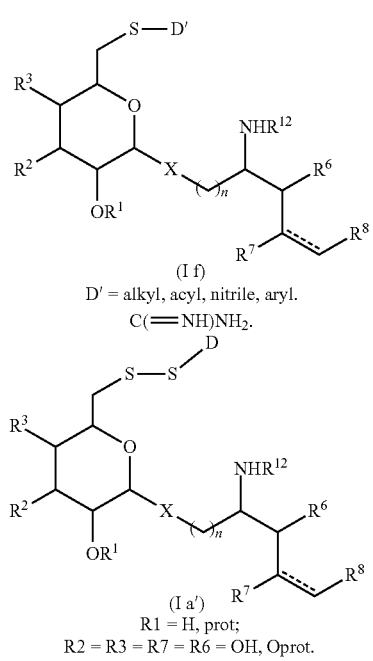
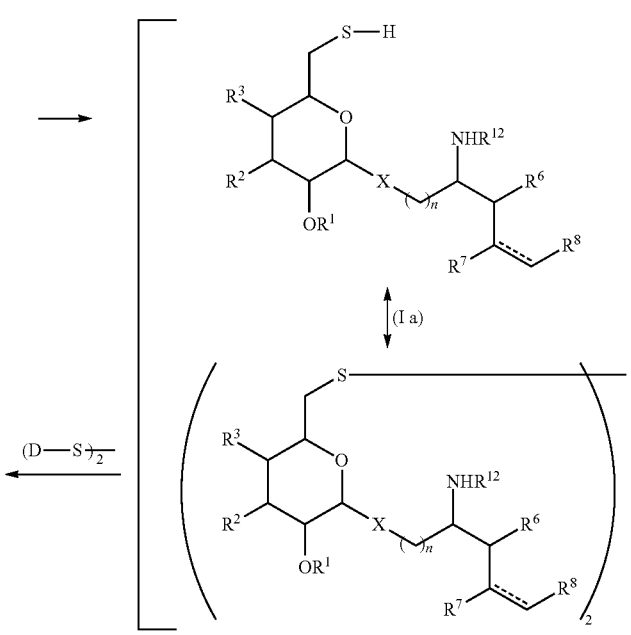

In the case of compounds of formula (I) where Z is a disulfide, these materials can be accessed using thiol-exchange chemistry. This requires the generation of compounds I a which can be accessed by deprotection of a specific subset of compounds of type I f (wherein D'=alkyl, acyl, nitrile, aryl, C(=NH)NH$_2$) (Scheme 7). The removal of standard thiol protecting groups can be carried out using well documented procedures (Greene and Wutz, 1991), or using more specific procedures as outlined below, to generate the free thiol material (I a). Compounds such as thiol I a are in equilibrium with the corresponding disulfide and will often exist solely as the disulfide in the absence of a suitable oxidant. Therefore it may be advantageous to add an oxidant into the reaction mixture, e.g. β-mercaptoethanol, TCEP-HCl or DTT, when trying to form compound I a' from I a. The conversion of I f to I a' as detailed in Scheme 3 can optionally be carried out as a one-pot procedure whereby I a would be generated in situ and immediately reacted on to I a' with the disulfide D-S—S-D (where D=as defined in Statements of Invention).

In the deprotection of compounds of type I f, it is feasible that D' can be selectively removed in the presence of the other protecting groups that may be present. Alternatively, a global deprotection may be carried out to remove all protecting groups and D' in the generation of I a, allowing access to the deprotected version of I a'.

Where D'=alkyl (e.g. t-Bu, CPh$_3$) mercury salts (Fujiwara and Fu, 2011), acids (Divakar, Mottoh, et al. 1990) or silane reagents (Zhu, 2006) can be used; where D'=nitrile, use sodium tetraborohydride (Specha, 1993); where D'=acyl, sodium methoxide or hydrazine can be used (Froehlich, Schrank et al. 2012; Sherry, Loy et al. 2004) and where D'=aryl, sodium methoxide can also be used; where D'=C(=NH)NH$_2$, sodium hydroxide can be utilised (Yoshikiyo, Ohta et al. 2008). Suitable solvents include THF, MeOH, AcOH, DMF, water and mixtures thereof.

For the preparation of compounds I a', a mixture of thiol/disulfide I a (1.0 equiv) and the disulfide of interest (1.0-3.0 equiv) (e.g. dipyridyl disulphide, dithiothreitol) are allowed to react at room temperature under an inert atmosphere in an appropriate solvent system buffered to pH 6.5-7.5 (Widdison, Wilhelm et al. 2006). Suitable solvents may include chloroform, THF, methanol, DMF, DMSO, t-butanol, water or mixtures thereof.

Where deprotection of I a is required, this can be achieved by standard deprotection chemistry known to those skilled in the art.

General Method (4) for the Synthesis of Compounds of Formula (I) where Z is Substituted Thiol

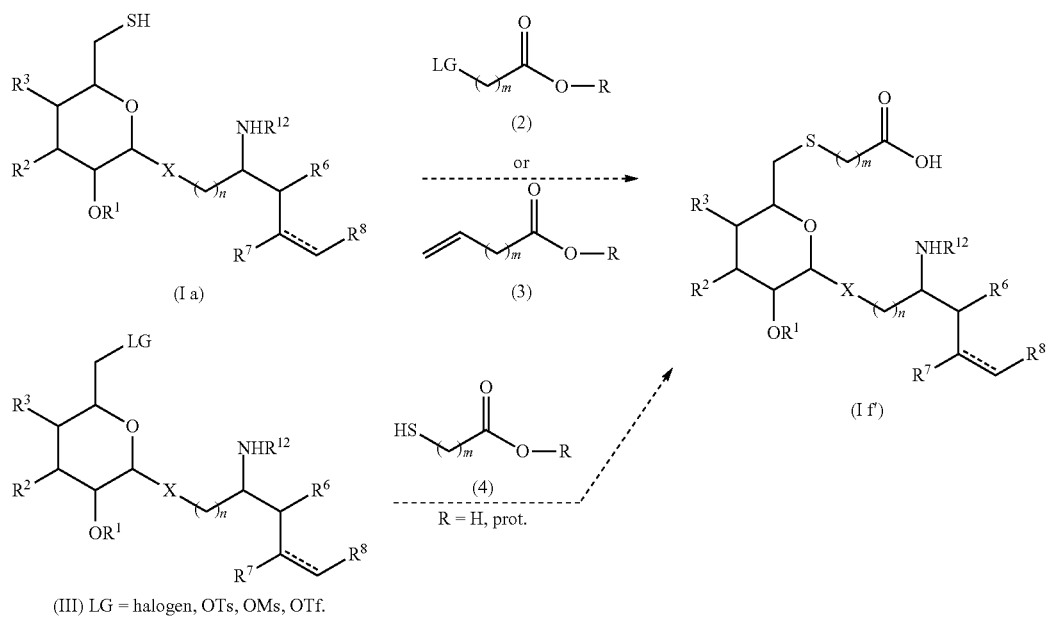

(III) LG = halogen, OTs, OMs, OTf.

The acetic acid terminated 6-thio-αGalCer compound (I f') can be generated via known methods (Smeenk, Dailly et al. 2012; Chen, Li et al. 2006) using commercially available substituted alkyl esters/carboxylic acids bearing appropriate leaving groups (2) or thiols (4). Alkenyl esters/carboxylic acids (3) can also be used in this strategy (Rim, Lahey et al. 2009).

These substituted alkyl and alkenyl esters/carboxylic acids can alternatively be synthesised using routine methods. In the case of the ester derivatives, a suitable deprotection method would be utilised to access the corresponding carboxylic acid (I f').

Generation of the deprotected versions of compounds I f' is achieved by standard deprotection chemistry known to those skilled in the art.

General Method (5) for the Synthesis of Compounds of Formula (I) where Z is Sulfoxide (wherein X=O, $CH_2$; Z=SO; D=an optionally substituted alkyl group, an optionally substituted alkenyl group, an optionally substituted alkynyl group, an optionally substituted aralkyl group, an optionally substituted aryl group, an optionally substituted aryl group or a radical of formula D3.)

Scheme 9

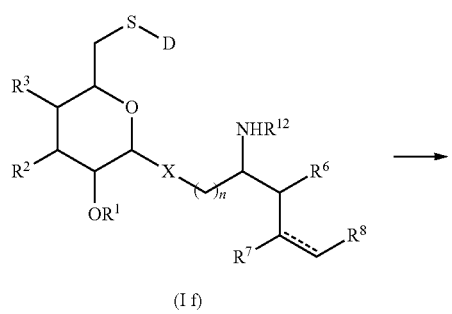

(wherein Z=S; D=a radical of formula D3.)

-continued

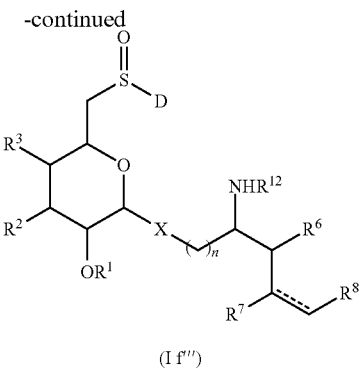

R1 = prot; R2 = R3 = R7 = R6 = Oprot.

To access compounds of type I f''', a solution of m-CPBA (1.0-2.0 equiv) in an appropriate solvent is added to a solution of compound I f (1.0 equiv) stirring in a suitable solvent under an inert atmosphere at low temperatures (−78-0° C.). After a short time period (5-30 mins), the reaction is quenched and diluted with additional solvent before the organic phase is washed and concentrated (Fascione, Webb et al. 2012). The crude material is then purified by flash column chromatography on the appropriate solid phase (e.g. silica gel, C4, and/or C18 silica).

Alternative oxidants include $H_2O_2$, $NaIO_4$, oxone and 3,3-dimethyldioxirane, while suitable solvents include THF, MeCN, MeOH, EtOH, $CH_2Cl_2$, water and mixtures thereof.

Generation of the deprotected versions of compounds I f''' is achieved by standard deprotection chemistry known to those skilled in the art.

General Method (6) for the Synthesis of Compounds of Formula (I) where Z is Sulfone (wherein X=O, $CH_2$; Z=$SO_2$; D=an optionally substituted alkyl group, an optionally substituted alkenyl group, an optionally substituted alkynyl group, an optionally substituted aralkyl group, an optionally substituted aryl group, an optionally substituted aryl group or a radical of formula D3.)

Scheme 10

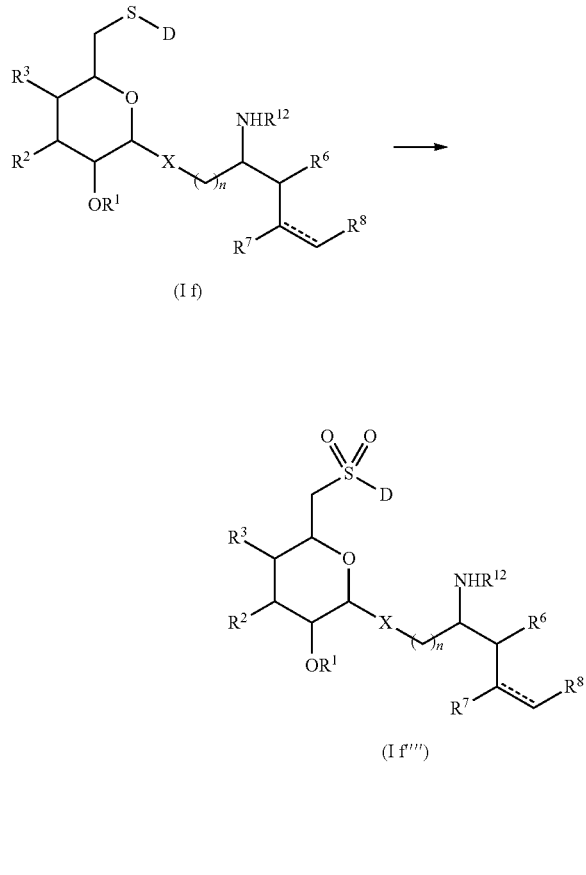

(I f)

(I f'''')

R1 = prot; R2 = R3 = R7 = R6 = Oprot.

For the preparation of compounds I f'''', a solution of m-CPBA (1.0-2.0 equiv) in an appropriate solvent is added to a solution of compound I f (1.0 equiv) stirring in a suitable solvent under an inert atmosphere at low temperatures (−20-0° C.) (Park, Kong et al. 2011). After a suitable time period (30 mins-2 hours), the reaction is quenched, diluted with additional solvent and the organic phase washed. Once concentrated, the crude material is purified by flash column chromatography on the appropriate solid phase (e.g. silica gel, C4, and/or C18 silica).

Alternative oxidants include $H_2O_2$, $NaIO_4$, oxone and 3,3-dimethyldioxirane, while suitable solvents include THF, MeCN, MeOH, EtOH, $CH_2Cl_2$, water and mixtures thereof.

Generation of the deprotected versions of compounds I f'''' is achieved by standard deprotection chemistry known to those skilled in the art.

General Method (7) for the Synthesis of Compounds of Formula (I) where Z-D is Thio-Succinimide or Thio-Maleimide (wherein Z=S; D=a radical of formula D1 or a radical of formula D2.)

Scheme 11

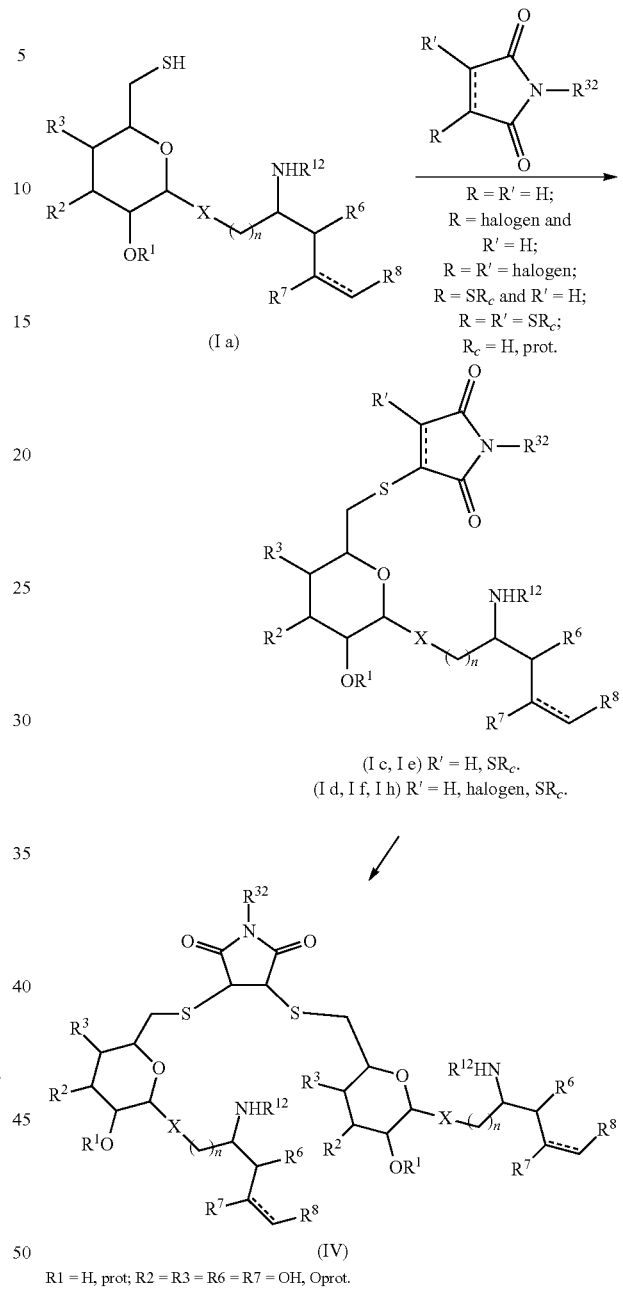

(I a)

R = R' = H;
R = halogen and R' = H;
R = R' = halogen;
R = $SR_c$ and R' = H;
R = R' = $SR_c$;
$R_c$ = H, prot.

(I c, I e) R' = H, $SR_c$.
(I d, I f, I h) R' = H, halogen, $SR_c$.

(IV)

R1 = H, prot; R2 = R3 = R6 = R7 = OH, Oprot.

Conversion of compound (I a) to the corresponding thio-succinimide derivatives (I c, I e) is carried out using well documented chemistry (Girouard, Houle et al. 2005) between thiol/disulfide I a, the unsubstituted maleimide reagent (R=R'=H, for I c) and the mono-substituted maleimide (R=H, R'=halogen, for I e). Synthesis of thio-maleimide compounds I d, I f and I h can be achieved by reaction of I a with a halogenated maleimide using well known literature procedures: unsubstituted maleimide (Gonzalez-Temporano, Osante et al. 2004), mono-halo maleimide (Tedaldi, Aliev et al. 2012; Smith, Schumacher et al. 2010) and di-halo maleimide (Muus, Hose et al. 2010; Smith, Schumacher et al. 2010).

Alternatively, thiomaleimides I d, I f and I h can be accessed via a thiol-exchange reaction using a mono- or di-thiomaleimide reagent (R=SR$_c$ and R'=H, or R=R'=SR$_C$) (Schumacher, Nobles et al. 2011). It may be necessary to add a suitable oxidant into the reaction mixtures such as β-mercaptoethanol, TCEP-HCl or DTT.

To access compounds of type I c and I e, the unsubstituted maleimide (R=R'=H) (1.0-5.0 equiv) is added to thiol/disulfide I a (1.0 equiv) stirring in a suitable solvent under an inert atmosphere at room temperature. Once the reaction is complete (TLC), water is added and the solution extracted with an appropriate solvent. The organic layers are combined, concentrated and purified by flash column chromatography on the appropriate solid phase (e.g. silica gel, C4, and/or C18 silica). Suitable solvents include THF, DMF, DMSO, toluene or mixtures thereof.

For the preparation of compounds I d, I f and I h, thiol/disulfide I a (1.0 equiv) is added to a solution of the desired halogenated maleimide (R=halogen and R'=H, or R=R'=halogen) (1.0-3.0 equiv) and imidazole (1.0-3.0 equiv) in a suitable solvent stirring at room temperature. After the reaction is complete (TLC), the product mixture is partitioned between ammonium and a suitable solvent and the combined organic layers concentrated. The crude material is purified by flash column chromatography on the appropriate solid phase (e.g. silica gel, C4, and/or C18 silica). Suitable solvents include THF, DMF, DMSO, CHCl$_3$, toluene, water and mixtures thereof.

Generation of the deprotected versions of compounds I c-I f and I h is achieved by standard deprotection chemistry known to those skilled in the art.

Compounds of formula (IV) where ╌╌╌ is an optional double bond are formed directly from thio-maleimide compounds I d, I f and I h where R' is halogen or H and ╌╌╌ is a double bond.

General Method (8) for the Synthesis of Compounds of Formula (I) where Z is Sulfoxide or Sulfone (wherein X=O, CH$_2$; when Z=SO or SO$_2$; D=halogen.)

Scheme 12

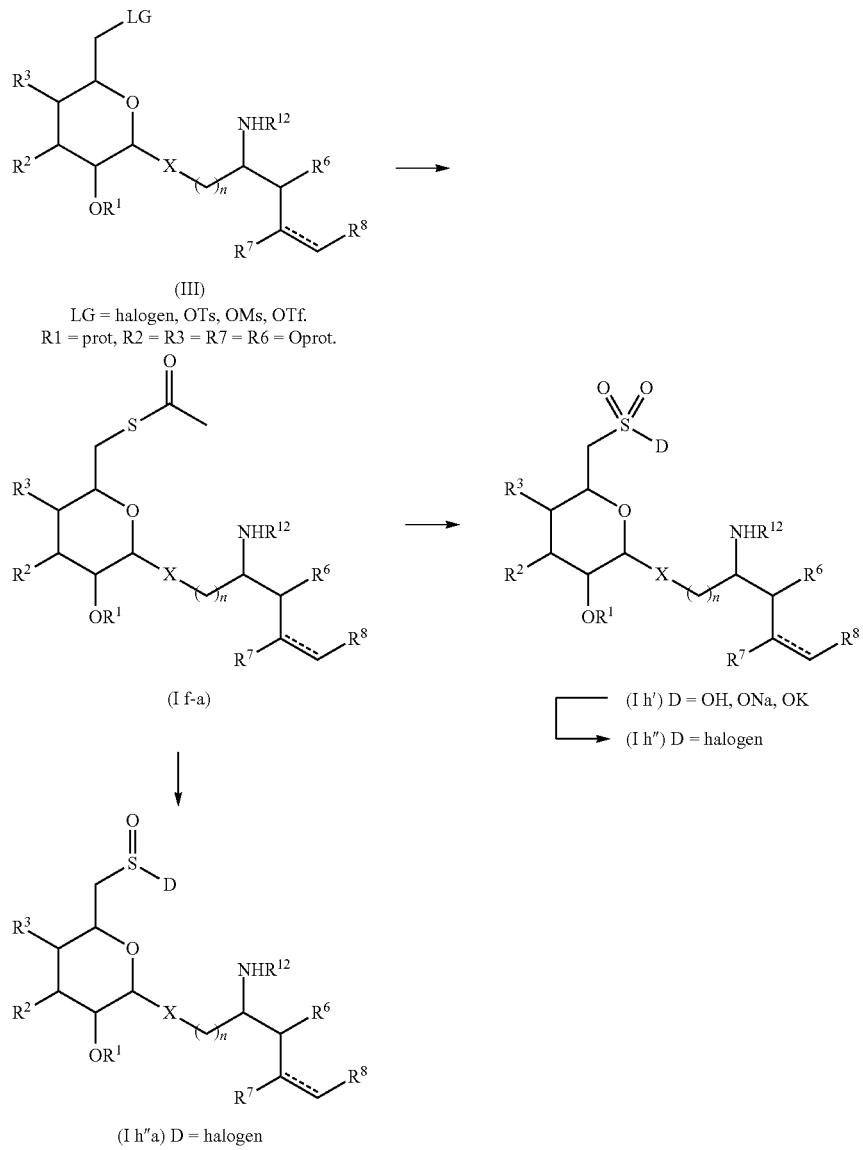

(III)
LG = halogen, OTs, OMs, OTf.
R1 = prot, R2 = R3 = R7 = R6 = Oprot.

(I f-a)

(I h') D = OH, ONa, OK
(I h") D = halogen (I h"a) D = halogen

A range of sulfonyl derivatives of type I h" can be readily accessed via thioacetate I f-a as illustrated in Scheme 8 above.

Starting from compound III, the leaving group at the 6-position can be displaced by reaction with potassium thioacetate to give the intermediate thioacetate I f-a which can then be oxidised to give the desired sulfonic acid or sulfonate salt I h' (Liptak, Balla et al. 2004; Manzo, Tramice et al. 2012). Appropriate oxidising agents include $H_2O_2$ and oxone. Sulfone derivative I h' can alternatively be accessed directly from compound III by reaction with sodium sulphite (Liptak, Balla et al. 2004).

Conversion of compounds I h' into the corresponding sulfonyl chlorides (I h") can be achieved through the use of appropriate chlorinating agents (Kærnø, Werder et al. 2005; Obreza and Gobec 2004). These include N-chlorosuccinimide (NCS), $PX_3$ and $PX_5$ (X=halogen), $SOCl_2$, $COCl_2$, oxalyl chloride and triphosgene.

This strategy can also be applied to the corresponding sulfinyl derivatives (Scheme 12). Treatment of thioacetate I f-a with an appropriate reagent gives access to sulfinyl chlorides of type I h"a. Appropriate reagents for this step include those specified above as well as sulfuryl chloride or chlorine in the presence of $Ac_2O$ (Moree, van der Marel et al. 1996).

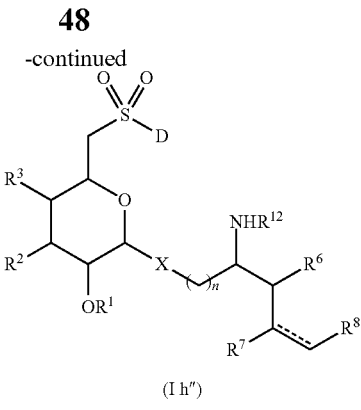

(I h")

D = halogen

Additionally, I h" can be accessed directly from I a (Scheme 13) by reaction with an oxidant and a chlorinating reagent, e.g. $H_2O_2$ and $SOCl_2$ (Bahrami, Khodaei et al. 2009). Alternative oxidants include potassium nitrate, peracetic acid, mCPBA, oxone, $NaIO_4$ and $KMMnO_4$, while suitable chlorinating reagents include $POCl_3$, $TiCl_4$, $Cl_2$, sulfuryl chloride and NCS.

Generation of the deprotected versions of compounds of type I h' and I h" is achieved by standard deprotection chemistry known to those skilled in the art.

General Method (9) for the Preparation of Thioalkyl Reagents

Scheme 13

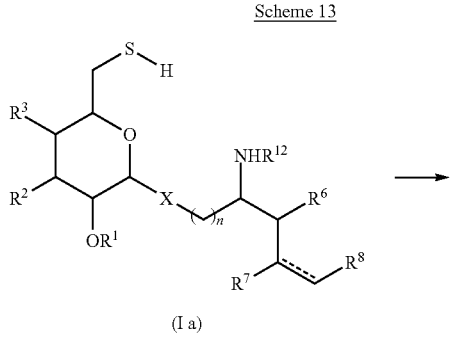

(I a)

Scheme 14

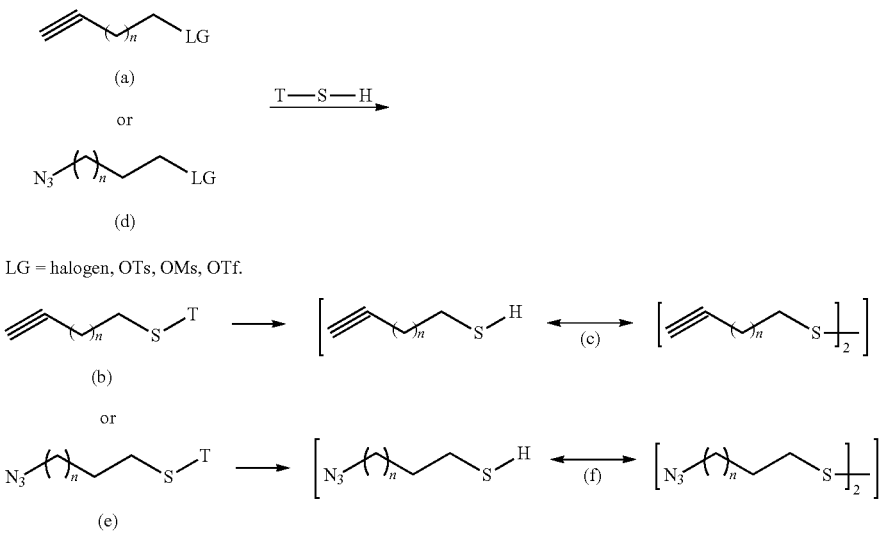

LG = halogen, OTs, OMs, OTf.

T = H, prot.

The desired thiol reagents used in the preparation of compounds of formula I f and I a can be generated by reaction of an alkynyl alkane (a) (Ren, Turos et al. 1995) or azido alkane (d) (Isobe, Cho et al. 2007) bearing an appropriate leaving group, with a suitable thiolating reagent (T-S—H). The alkynes and azides documented here are either commercially available or accessible by routine chemical methods. Any protecting groups present in T of b and e are removed using standard deprotection methods to give the free thiol/disulfide (c or f). Starting material a also encompasses alkenes which can be generated by reduction of the corresponding alkynyl reagents.

To a solution of thiol T-S—H (1.0 equiv) and 3-azido-1-iodo-propane d (1.0-3.0 equiv) in a suitable solvent under an inert atmosphere, is added aqueous NaOH (1.0-3.0 equiv) in small portions over 10-30 mins. The solution is stirred at room temperature until deemed to be complete (TLC), neutralized and concentrated. The crude material is purified by chromatography on the appropriate solid phase (e.g. silica gel, C4, and/or C18 silica). Suitable thiolating reagents include potassium thioacetate, thiourea, dipyridyldisulfide and dibenzyldisulfide. Alternative bases include $NEt_3$, DBU and $KHCO_3$, while appropriate solvents include THF, DMF, $Et_2O$, toluene, water or mixtures thereof.

General Method (10) for the Preparation of Maleimide Reagents

In the case of the dibromo-maleimide series (h, $R_a=R_b$=halogen), the primary amine of choice can also be reacted with dibromomaleic acid (j) to yield the corresponding dibromo-N-substituted maleimide h (Muus, Hose et al. 2010; Wilson, Thalji et al. 2006). The same strategy can be applied to succinic acid (Groutas, Brubaker et al. 1989). Additionally, bromination of N-substituted maleimides such as k will also access the desired N-substituted bromomaleimide h (Banwell, Jones et al. 2010).

The primary amines and haloalkanes used in Scheme 15 are either commercially available or easily accessible by general chemical methods.

Scheme 16

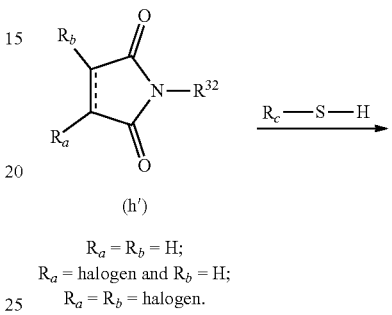

(h')

$R_a = R_b = H$;
$R_a$ = halogen and $R_b = H$;
$R_a = R_b$ = halogen.

Scheme 15

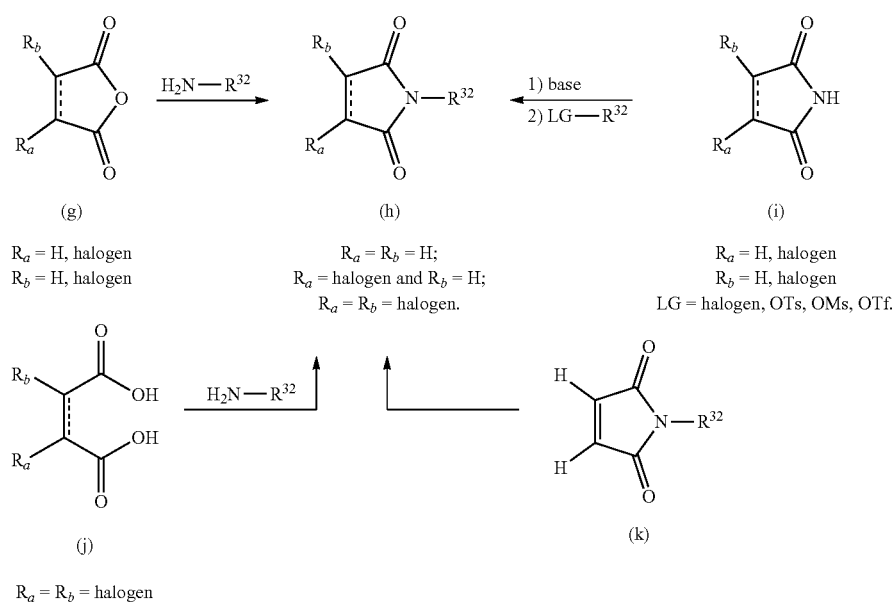

(g)
$R_a$ = H, halogen
$R_b$ = H, halogen (h)
$R_a = R_b = H$;
$R_a$ = halogen and $R_b = H$;
$R_a = R_b$ = halogen.

(i)
$R_a$ = H, halogen
$R_b$ = H, halogen
LG = halogen, OTs, OMs, OTf.

(j)
$R_a = R_b$ = halogen (k)

The maleimides (h) ($R_a=R_b$=H, or $R_a$=halogen and $R_b$=H, or $R_a=R_b$=halogen) utilised in the synthesis of compounds of formula I c-I f and I h can be prepared using a variety of well documented procedures. The main methods used are the condensation reaction between a maleic anhydride (g) and a primary amine ($H_2N$—$R^{32}$) (Stewart, Polomska et al. 2007; Jones, Strickland et al. 2012), coupling of a bromomaleic anhydride with an amine (Jones, Strickland et al. 2012) or a displacement reaction between an alkyl bearing a leaving group (LG-$R^{32}$) and the N-unsubstituted bromomaleimide i (Joyce, Gainor et al. 1987). Similar chemistry can be applied to the succinic anhydride derivatives (Verschueren, Dierynck et al. 2005).

-continued

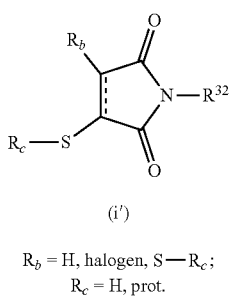

(i')

$R_b$ = H, halogen, S—$R_c$;
$R_c$ = H, prot.

Thiolyated succinimide and maleimide reagents can be utilised in Scheme 1 to access I f (D=D1 or D2) and Scheme 7 to generate compounds of type I c-I f and I h (D=radical of formula D1 or D2) via thiol-exchange chemistry. The synthesis of the thio-maleimide compounds is shown in Scheme 16.

Thiolyated succinimide derivative i' can be generated from maleimide compound h' ($R_a$=$R_b$=H) and thiol $R_c$—S—H using thiol-ene chemistry as referenced herein, or alternatively by halogen displacement of succinimide analogue h' ($R_a$=halogen, $R_b$=H) (Dietz, Rieck et al. 1989). This displacement chemistry can be extended to the maleimide compounds, to access thiolyated maleimides ($R_b$=H, halogen, S—$R_c$) (Muus, Farnsworth et al. 2010 and other relevant references as detailed in General Method 7).

Thiol reagent $R_c$—S—H can also be DTT, thiourea and dipyridyldisulfide.

To thiol $R_c$—S—H (1.0-3.0 equiv) in a suitable solvent system buffered to pH 7.0-8.5, the halogenated maleimide in a suitable solvent is added. The reaction is stirred at room temperature for a suitable time period and a salt then added (Schumacher, Nobles et al. 2011). Once complete (TLC) the reaction mixture is extracted with an appropriate extracting solvent, the organic layers combined and the solvent removed. The crude material is purified by flash column chromatography on the appropriate solid phase (e.g. silica gel, C4, and/or C18 silica). Suitable solvents include DMF, dioxane, DMSO, water and mixtures thereof.

Where the thiol in i' is protected ($R_c$=prot), this group can be removed to access the free thiol using standard deprotection methods known to those skilled in the art, some of which are detailed herein.

Other Aspects

The compounds of the invention may be administered to a patient by a variety of routes, including orally, parenterally, by inhalation spray, topically, rectally, nasally, buccally, intravenously, intra-muscularly, intra-dermally, subcutaneously or via an implanted reservoir, preferably intravenously. The amount of compound to be administered will vary widely according to the nature of the patient and the nature and extent of the disorder to be treated. Typically the dosage for an adult human will be in the range 50-4800 μg/m². The specific dosage required for any particular patient will depend upon a variety of factors, including the patient's age, body weight, general health, sex, etc.

For oral administration the compounds of the invention can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried corn-starch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant. In one preferred embodiment, the compounds are administered by intravenous injection, where the diluent comprises an aqueous solution of sucrose, L-histidine and a pharmaceutically acceptable surfactant, e.g. Tween 20.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

ABBREVIATIONS

Figure 1:
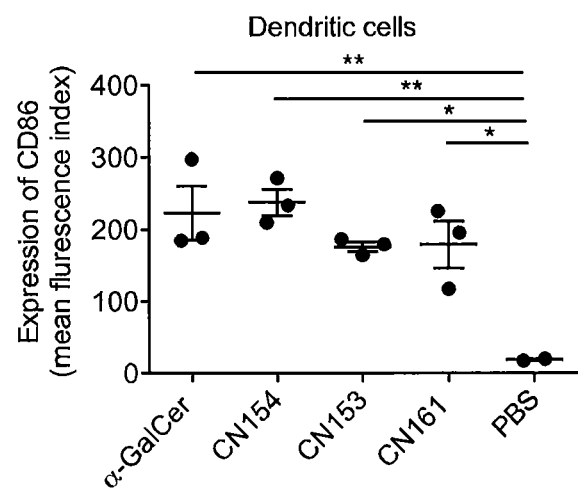
FIG. 1 shows CD86 expression on dendritic cells. The data show that injection of compounds of the invention induces activation of iNKT cells and subsequent maturation of dendritic cells, as indicated by up-regulation of expression of the activation marker CD86. Groups of C57BL/6 mice (n=3) are injected intravenously with 0.23 nmol of the indicated compounds and then the spleens removed 20 h later for the analysis of CD86 expression on CD11c$^+$dendritic cells by antibody labelling and flow cytometry. Mean fluorescence index (MFI)±SEM are presented. *P<0.05, *P<0.01, ***P<0.001
Figure 2:
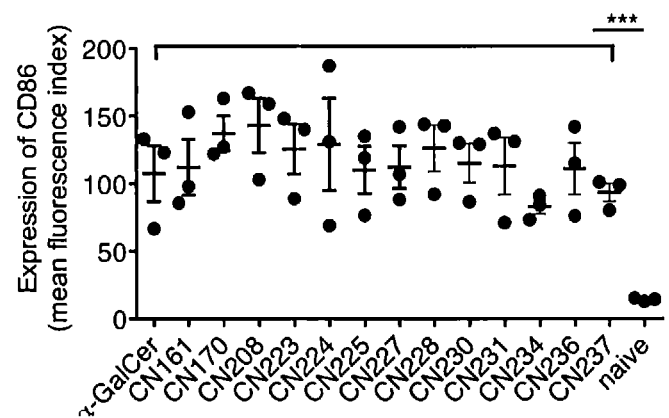
FIG. 2 shows CD86 expression on dendritic cells. The data show that injection of compounds of the invention induces activation of iNKT cells and subsequent maturation of dendritic cells, as indicated by up-regulation of expression of the activation marker CD86. Groups of C57BL/6 mice (n=3) are injected intravenously with 0.23 nmol of the indicated compounds and then the spleens removed 20 h later for the analysis of CD86 expression on CD11c$^+$ dendritic cells by antibody labelling and flow cytometry. Mean fluorescence index (MFI)±SEM are presented. *P<0.05, *P<0.01, ***P<0.001
Figure 3:
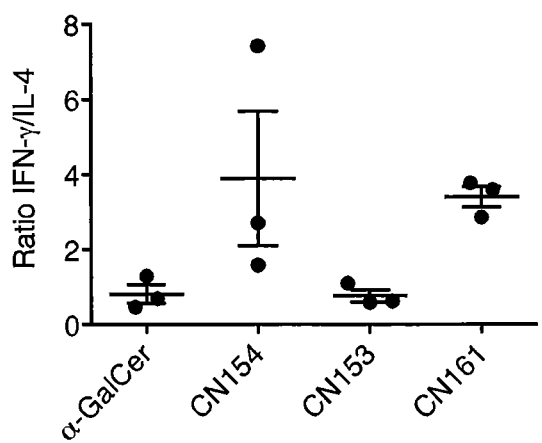
FIG. 3 shows the ratio of cytokines IFN-γ/IL-4 as measured in blood at 18 h (IFN-γ) and 3 h (IL-4) respectively. The data show that injection of some compounds of the invention induces higher ratios of IFN-γ/IL-4 as compared to α-GalCer. Groups of C57BL/6 mice (n=3) are injected intravenously with 0.23 nmol of the indicated compounds.
Figure 4:
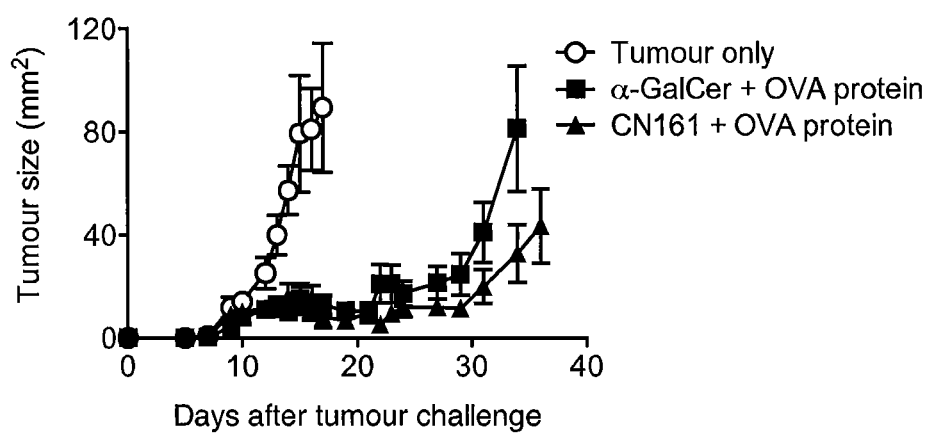
FIG. 4 shows progression of B16.OVA melanoma over 37 days after challenge. Groups of C57BL/6 mice (n=5) are injected with 1×10$^5$ live B16.OVA tumour cells subcutaneously on day 0. On day 6 0.23 nmol of the indicated compounds (α-GalCer or CN161) mixed with OVA protein (200 μg) are administered intraveneously. The tumour size is monitored regularly with calipers until the first animal in each group reached 200 mm², at which point the whole group is culled.
Figure 5:
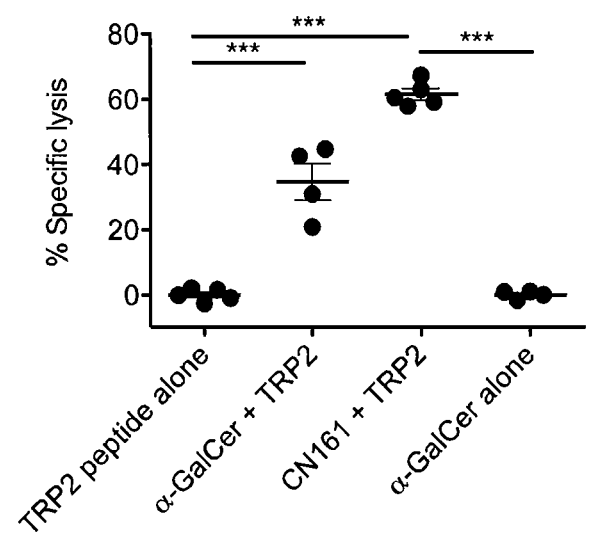
FIG. 5 shows the cytotoxic capacity of T cells with specificity for the H-2K$^b$-restricted peptide SVYDFFVWL from the tumour-associated antigen TRP-2 following intravenous administration of vaccines comprising compounds of the invention (0.23 nmol) and the long peptide sequence SVYDFFVWLKFFHRTCKCTGNFA from the TRP-2 protein (0.57 nmol). Control animals are injected with the long peptide alone, or α-GalCer alone. Flow cytometry is used to assess the killing of target cells comprised of syngeneic splenocytes loaded ex vivo with 5 μM SVYDFFVWL injected intravenously 7 days after vaccination. To discriminate the targets from host tissue, the injected cells are labelled with the fluorescent dye carboxyfluorescein succinimidyl ester (CFSE). A cohort of syngeneic splenocytes (without peptide) labelled with the fluorescent dye cell tracker orange are also injected to serve as controls. Killing is defined as the percentage of peptide-loaded targets killed relative to control cells. Each treatment group contained 5 animals with mean percentage of killing per group±SEM shown. The data show that injection of CN161 with the long TRP2 peptide induces a greater cytotoxic response against SVYDFFVWL-loaded targets than co-injection with α-GalCer or injection of peptide alone.
Figure 6:
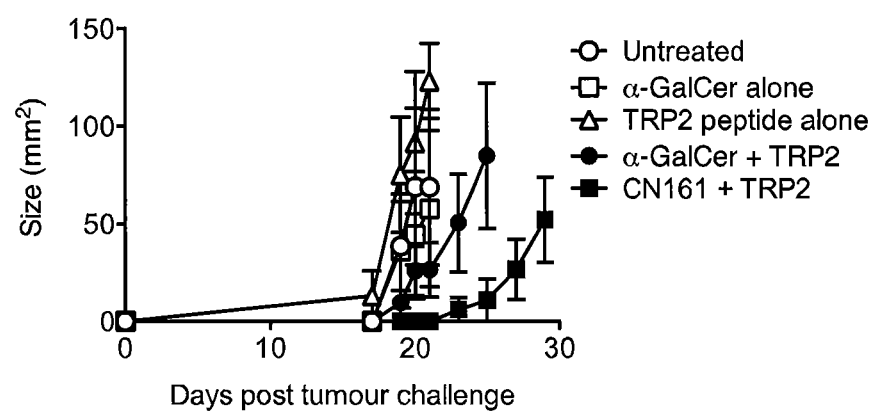
FIG. 6 shows the antitumour activity against B16.OVA melanoma following intravenous administration of vaccines comprising compounds of the invention (0.23 nmol) and the long peptide sequence SVYDFFVWLKFFHRTCKCT-GNFA from the TRP2 protein (0.57 nmol). Control animals are injected with the long peptide alone, α-GalCer alone, or left untreated. The mean tumour sizes per group (n=5)±SEM are shown. These data show that vaccination with CN161 and long TRP2 peptide results in anti-tumour activity.
Figure 7:
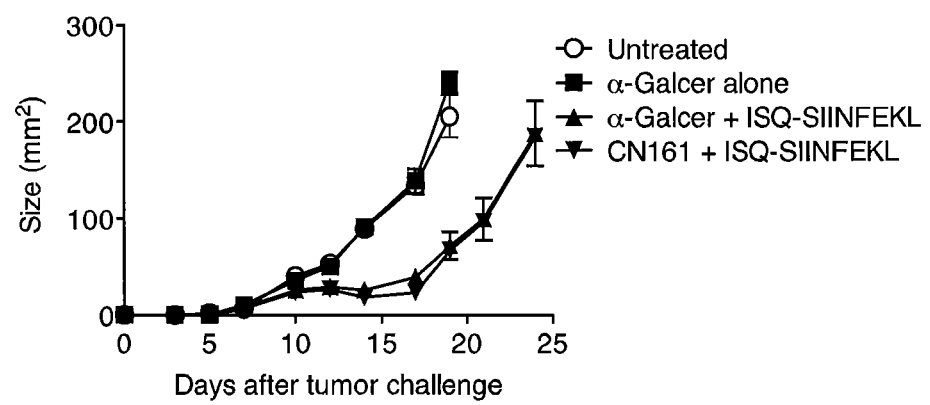
FIG. 7 shows the antitumour activity against B16.OVA melanoma following intravenous administration of vaccines comprising compounds of the invention and the long peptide sequence KISQAVHAAHAEINEAGRESIINFEKLTEWT from chicken ovalbumin (OVA) protein, a "model" tumour antigen encoded by the melanoma cells. These data show that vaccination with CN161 and long OVA peptide results in equivalent anti-tumour activity compared to injection of the peptide with α-GalCer.
Figure 8A:
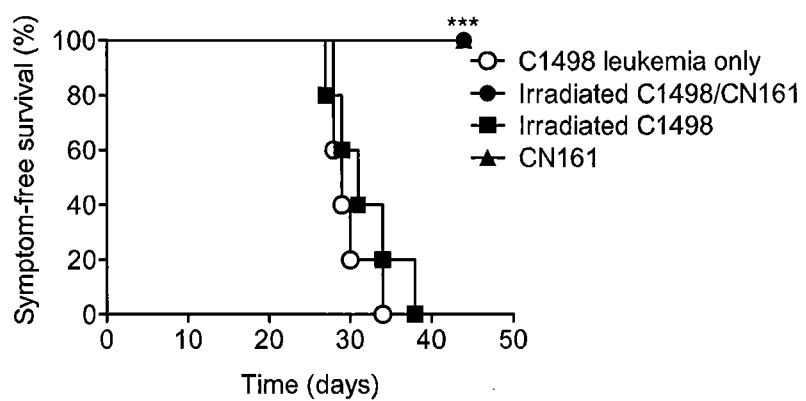
FIG. 8 shows the anti-leukemia activity of intravenously administered cell-based vaccines used to prevent challenge with C1498 acute leukemia cells. The prophylactic vaccines consist of irradiated C1498 cells that are incubated with compounds of the invention for 24 h. Control animals are injected with irradiated C1498 cells alone, compound alone, or left untreated. The time to onset of leukemia-associated symptoms are shown. (A) Analysis of vaccines incorporating CN161. (B) Analysis of vaccines incorporating α-GalCer. These data show that cell-based vaccines incorporating CN161 or α-GalCer provide significant protection against leukemia development. Also, CN161 alone, but not α-GalCer alone, can provide protection in this model.
Figure 8B:
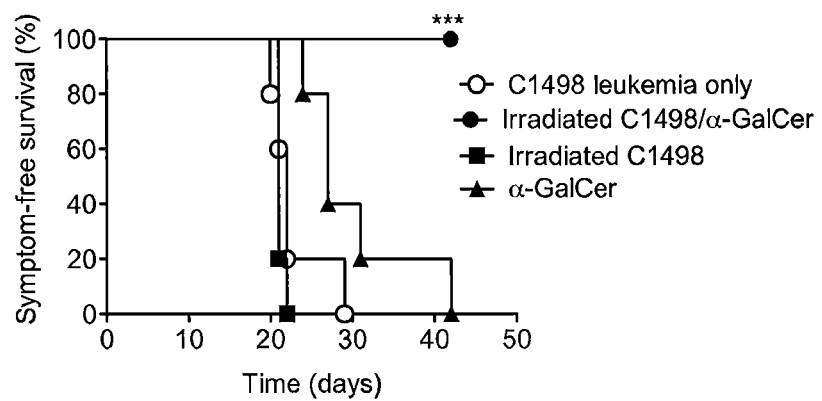
Figure 9A:
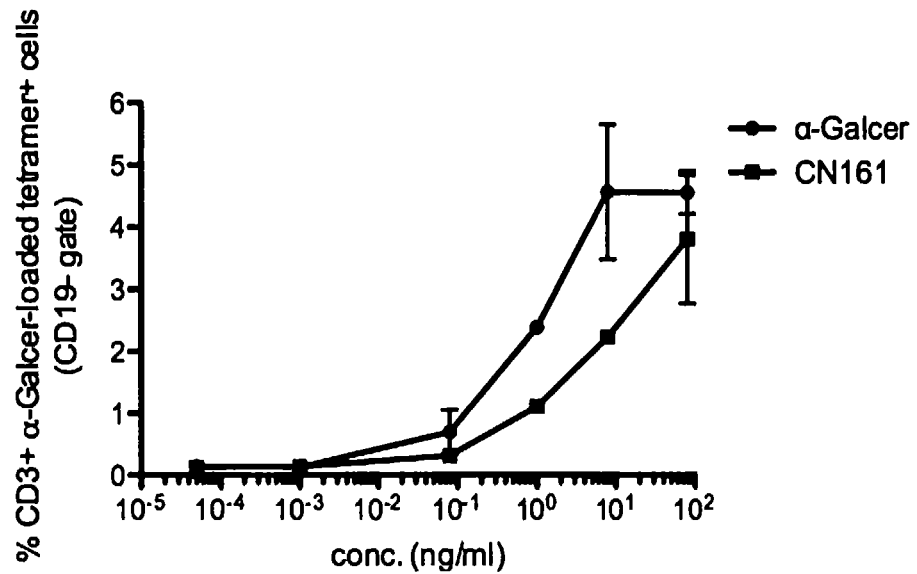
FIG. 9 shows the effect of compounds of the invention on proliferation of human NKT cells. Peripheral blood mononuclear cells from one donor are cultured for 7 days with different doses of the indicated compounds in the presence of IL-2, and then the percentages of NKT cells in the final cultures determined by flow cytometry with fluorescent α-GalCer-loaded CD1d tetramers and anti-CD3. Data are expressed as percentage of NKT cells (α-GalCer/CD1d tetramer and anti-CD3-binding cells) of total T cells (all anti-CD3-binding cells).
Figure 9B:
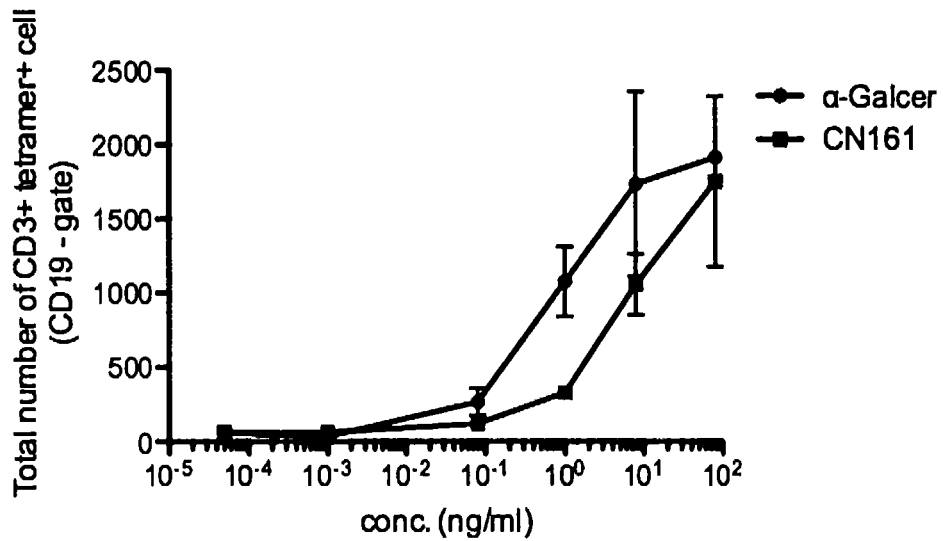

NKT cells Natural killer T-cells
iNKT cells Invariant natural killer T-cells
CD1 Cluster of differentiation 1
DC Dendritic cells
MHC Major histocompatibility complex
PBMC Peripheral blood mononuclear cell
TLR2 Toll-like receptor 2
MUC-1 Mucin 1, cell surface associated
Th1 T helper cells, type 1
Th2 T helper cells, type 2
MFI Mean fluorescence index
SEM Structural equation modelling
IFN-γ Interferon-gamma
IL-4 Interleukin 4
TMS Trimethylsilyl
TBAI Tetrabutylammonium iodide
DIPEA Diisopropylethylamine
NMR Nuclear magnetic resonance spectrometry
HRMS High resolution mass spectrometry
ESI Electrospray ionisation
Q-Tof Quadrupole time-of-flight mass spectrometer
RT Room temperature
TLC Thin layer chromatography
THF Tetrahydrofuran
m-CPBA meta-chloroperoxybenzoic acid
DAST Diethylaminosulfur trifluoride
DCM Dichloromethane
DMF Dimethylformamide
DMSO Dimethylsulfoxide
DMAP Dimethylaminopyridine
DME Dimethoxyethane
DTT Dithiothreitol
TCEP-HCl Tris(2-carboxyethyl)phosphine hydrochloride
NHS N-hydroxy succinimide
NCS N-chloro succinimide
OTs O-Tosyl (O-p-toluenesulfonyl)
OMs O-Mesyl (O-methane sulfonyl)
OTf O-Triflate (O-trifluoromethanesulfonyl)
EDC 1-Ethyl-3-(3-dimethylaminopropyl)carbodiimide
IgE Immunoglobulin E
FACS Fluorescence-activated cell sorting
EDTA Ethylenediaminetetraacetic acid
Ab Antibody
RBC Red blood cell
cDNA Complementary deoxyribonucleic acid
PBS Phosphate-buffered saline
FCS Fetal calf serum
OVA Chicken ovalbumin

EXAMPLES

The invention is further described with reference to the following examples. It will be appreciated that the invention as claimed is not intended to be limited in any way by these examples. The examples described herein are for the purposes of illustrating embodiments of the invention. Other embodiments, methods, and types of analyses are within the capabilities of persons of ordinary skill in the art and need not be described in detail herein. Other embodiments within the scope of the art are considered to be part of this invention.

Anhydrous solvents are obtained commercially. Air sensitive reactions are carried out under Ar. Thin layer chromatography (TLC) is performed on aluminium sheets coated with 60 $F_{254}$ silica. Flash column chromatography is performed on Merck or SiliCycle silica gel (40-63 μm) or SiliCycle reversed phase (C18) silica gel (40-63 μm). NMR spectra are recorded on a Bruker 500 MHz spectrometer. $^1$H NMR spectra are referenced to tetramethylsilane at 0 Ppm (internal standard) or to residual solvent peak (CHCl$_3$ 7.26 ppm, CHD$_2$OD 3.31 ppm). $^{13}$C NMR spectra are referenced to tetramethylsilane at 0 ppm (internal standard) or to the deuterated solvent peak (CDCl$_3$ 77.0 ppm, CD$_3$OD 49.0

Example 1

Synthesis of (2S,3S,4R)-1-(6-Deoxy-64-butylthio-α-D-galactopyranosyloxy)-2-hexacosanoylamino-3,4-octadecandiol (CN153)

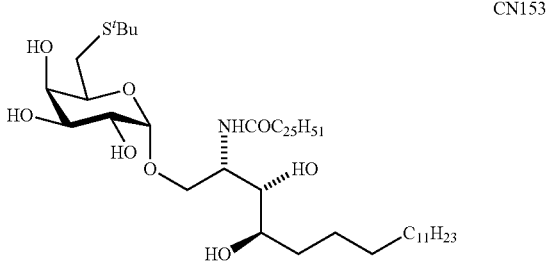

Example 1.1

(2S,3S,4R)-1-(2,3-Di-O-benzyl-6-O-(4-toluenesulfonyl)-α-D-galactopyranosyloxy)-3,4-di(benzyloxy)-2-hexacosanoylamino-octadeca-6-ene

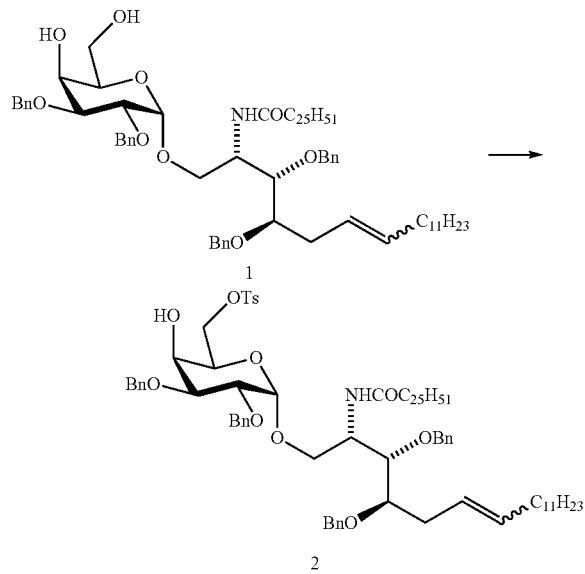

Tosyl chloride (0.400 g, 2.10 mmol) is added to diol 1 (0.180 g, 0.154 mmol) (which is prepared as described in Lee, A., K. J. Farrand, et al. (2006) "Novel synthesis of alpha-galactosyl-ceramides and confirmation of their powerful NKT cell agonist activity." *Carbohydr Res* 341(17): 2785-2798.) stirring in pyridine (8 mL) at RT. After 5 h the reaction mixture is diluted with CH$_2$Cl$_2$ (50 mL) and MeOH (10 mL) and stirred at RT for 18 h. The solvent is removed in vacuo. Purification of the resulting residue by silica gel chromatography (100% toluene changing to 20% EtOAc/toluene) gave the mono-tosylated material 2 (0.470 g, 0.343 mmol, 93%) as a white foam $[\alpha]_D^{20}=+16.4$ (c 0.005, CHCl$_3$); $^1$H NMR (500 MHz, CDCl$_3$) δ 0.88 (t, J=6.8 Hz, 6H), 1.22-1.32 (m, 62H), 1.47-1.51 (m, 2H), 1.86-1.95 (m, 2H), 2.02-2.06 (m, 2H), 2.40 (s, 3H), 2.43-2.53 (m, 2H), 3.60-3.63 (m, 1H), 3.74-3.77 (m, 4H), 3.80 (dd, J=9.7, 3.2 Hz, 1H), 3.93-3.94 (m, 1H), 3.97-3.99 (m, 1H), 4.09-4.17 (m, 2H), 4.33-4.38 (m, 1H), 4.51-4.54 (m, 2H), 4.58 (d, J=11.7 Hz, 1H), 4.60 (d, J=11.6 Hz, 1H), 4.66 (d, J=11.6 Hz, 1H), 4.70 (d, J=11.7 Hz, 2H), 4.74 (d, J=11.5 Hz, 1H), 4.77 (d, J=3.4 Hz, 1H), 5.43-5.52 (m, 2H), 5.68-5.72 (m, 1H), 7.22-7.32 (m, 22H), 7.74 (d, J=8.3 Hz, 2H); $^{13}$C NMR (126 MHz, CDCl$_3$) δ 14.1, 22.7, 25.6, 27.6, 27.8, 29.3, 29.4, 29.6, 29.7, 31.9), 36.7, 49.8, 67.1, 67.9, 68.5, 68.9, 71.5, 72.7, 73.3, 75.7, 77.0, 79.29, 79.31, 98.5, 125.4, 127.5, 127.6, 127.68, 127.72, 127.76, 127.8, 128.0, 128.3, 128.4, 128.5, 129.8, 132.1, 137.8, 138.2, 138.5, 138.6, 144.8, 172.8; HRMS (ESI): m/z calcd for C$_{85}$H$_{127}$NO$_{11}$SNa [M+Na]$^+$ 1392.9028, found 1392.9031.

Example 1.2

(2S,3S,4R)-1-(2,3-Di-O-benzyl-6-deoxy-6-t-butyl-thio-α-D-galactopyranosyloxy)-3,4-di(benzyloxy)-2-hexacosanoylamino-octadeca-6-ene

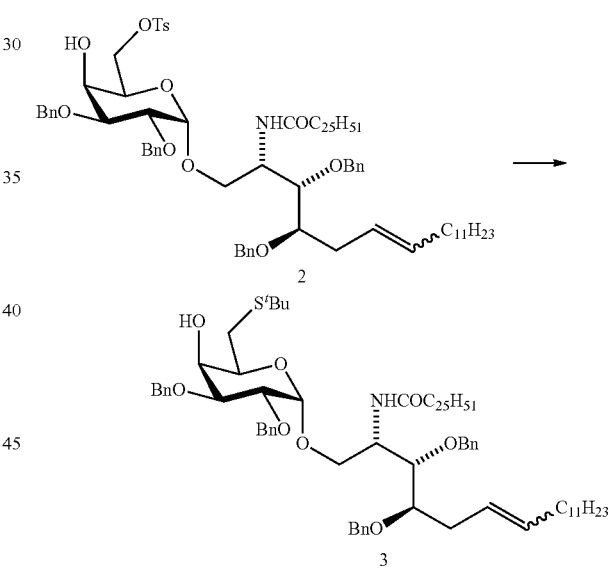

2-Methyl-2-propanethiol (0.016 ml, 0.146 mmol) and NaH (5.0 mg, 0.125 mmol) are added to tosylate 2 (0.100 g, 0.073 mmol) stirring in anhydrous THF (2 mL) at RT. After 18 h, the reaction is warmed to 30° C. and additional 2-Methyl-2-propanethiol (0.016 ml, 0.146 mmol) and NaH (5.0 mg, 0.208 mmol) are added. After a further 18 h the reaction is quenched by the addition of H$_2$O and stirred for 15 mins. The layers are then separated, and the organic phase is washed with H$_2$O, brine, dried (MgSO$_4$) and concentrated in vacuo. Purification by silica gel chromatography (10% EtOAc/petroleum ether changing to 18% EtOAc/petroleum ether) gives product 3 (61 mg, 0.047 mmol, 65%). $[\alpha]_D^{20}=+24.0$ (c 0.007, CHCl$_3$); $^1$H NMR (500 MHz, CDCl$_3$) δ 0.86-0.87 (m, 6H), 1.21-1.33 (m, 62H), 1.30 (s, 9H), 1.48-1.51 (m, 2H), 1.90-1.99 (m, 2H), 2.01-2.05 (m, 2H), 2.41-2.51 (m, 2H), 2.81 (d, J=7.0 Hz, 2H), 3.58-3.61

(m, 1H), 3.79-3.85 (m, 6H), 4.08 (br s, 1H), 4.29-4.34 (m, 1H), 4.52-4.62 (m, 4H), 4.70-4.77 (m, 4H), 4.817-4.822 (m, 1H), 5.42-5.51 (m, 2H), 5.85-5.89 (m, 1H), 7.23-7.35 (m, 20H); $^{13}$C NMR (126 MHz, CDCl$_3$) δ 14.1, 22.7, 25.7, 27.6, 27.9, 28.7, 29.36, 29.44, 29.7, 30.9, 31.9, 36.8, 42.3, 50.0, 68.1, 68.4, 69.8, 71.8, 72.5, 73.3, 73.5, 75.8, 77.7, 79.3, 79.7, 98.7, 125.7, 127.5, 127.6, 127.8, 127.9, 128.31, 128.36, 128.4, 128.5, 132.0, 138.0, 138.3, 138.64, 138.67, 172.7; HRMS (ESI): m/z calcd for C$_{82}$H$_{129}$NO$_8$SNa [M+Na]$^+$ 1310.9337, found 1310.9340.

Example 1.3

(2S,3S,4R)-1-(6-Deoxy-6-t-butylthio-α-D-galactopyranosyloxy)-2-hexacosanoylamino-3,4-octadecandiol (CN153)

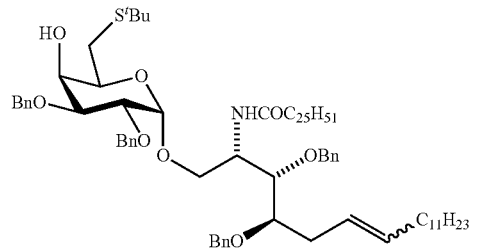

3

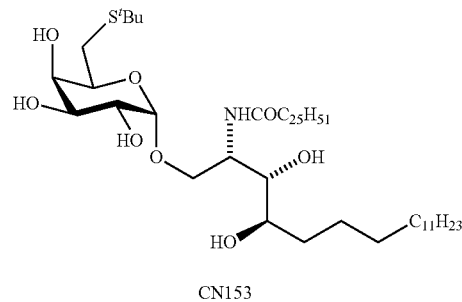

CN153

Protected 6-S$^t$Bu 3 (0.060 g, 0.047 mmol) is dissolved in MeOH (5 mL) and anhydrous THF (3 mL) before the addition of formic acid (0.3 mL) and Pd(OH)$_2$/C (10% Pd; 104 mg). The reaction vessel is evacuated, flushed with hydrogen and stirred at 30° C. for 5 h followed by 20° C. for 68 h. Once cooled, the product mixture is filtered through celite, washing repeatedly with CHCl$_3$:MeOH (3:1), and is then concentrated. The crude material is then purified by silica gel chromatography (100% CH$_2$Cl$_2$ changing to 5% MeOH/CH$_2$Cl$_2$) to isolate the target material CN153 as the major fraction alongside some partially hydrogenated material. This partially hydrogenated material is resubmitted to the same hydrogenation conditions as detailed above and purified by silica gel chromatography (100% CH$_2$Cl$_2$ changing to 5% MeOH/CH$_2$Cl$_2$) to give the product CN153 as a white solid, which is combined with that obtained earlier (30 mg, 0.032 mmol, 68%). [α]$_D^{20}$=+44.7 [c 0.003, CHCl$_3$: MeOH (3:1)]; $^1$H NMR (500 MHz, CDCl$_3$/CD$_3$OD 3:1) δ 0.88 (t, J=7.0 Hz, 6H), 1.24-1.41 (m, 68H), 1.33 (s, 9H), 1.52-1.68 (m, 4H), 2.19-2.23 (m, 2H), 2.79 (d, J=7.0 Hz, 2H), 3.35-3.37 (m, 1H), 3.54-3.59 (m, 2H), 3.70-3.74 (m, 2H), 3.78 (dd, J=10.0, 3.8 Hz, 1H), 3.83 (dd, J=7.4, 7.1 Hz, 1H), 3.90 (dd, J=10.6, 4.3 Hz, 1H), 3.94 (d, J=2.7 Hz, 1H), 4.18-4.21 (m, 1H), 4.87 (d, J=3.8 Hz, 1H); $^{13}$C NMR (126 MHz, CDCl$_3$/CD$_3$OD 3:1) δ 14.1, 22.9, 26.1, 28.8, 29.55, 29.60, 29.64, 29.8, 29.9, 30.0, 31.0, 32.1, 32.7, 36.8, 49.9, 50.3, 68.1, 69.0, 70.2, 70.7, 70.9, 72.4, 74.9, 100.0, 174.4; HRMS (ESI): m/z calcd for C$_{54}$H$_{107}$NO$_8$SNa [M+Na]$^+$ 952.7615, found 952.7623.

Example 2

(2S,3S,4R)-1-(6-Deoxy-6-mercapto-α-D-galactopyranosyloxy)-2-hexacosanoylamino-3,4-octadecandiol (CN237)

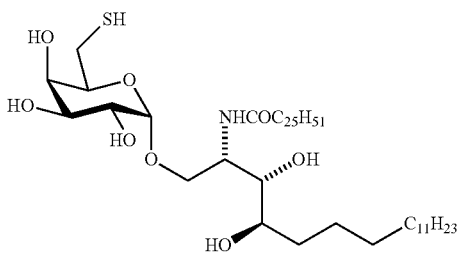

Example 2.1

(2S,3S,4R)-2-Hexacosanoylamino-1-(6-O-(4-toluenesulfonyl)-α-D-galactopyranosyloxy)-3,4-octadecandiol

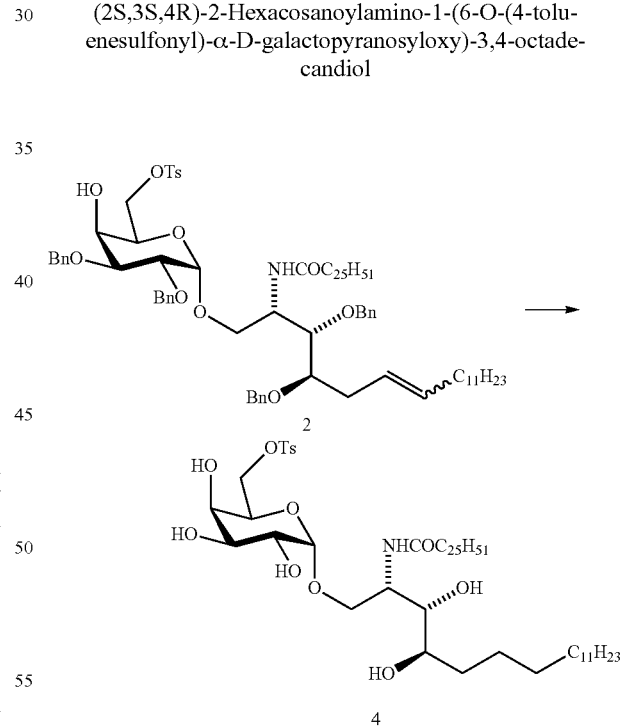

Pd(OH)$_2$/C (20% Pd; ~5 mg) is added to protected tosylate 2 (0.040 g, 0.029 mmol) stirring in anhydrous CH$_2$Cl$_2$: MeOH (4 mL; 1:1). The reaction vessel is evacuated and flushed with hydrogen and stirred at RT for 24 h. The product mixture is filtered through celite, washed repeatedly with CHCl$_3$:MeOH (3:1) and then concentrated. Purification by silica gel chromatography (100% CHCl$_3$ changing to 10% MeOH/CHCl$_3$) gives the target 4 (23 mg, 0.023 mmol, 79%) as a white solid. $^1$H NMR (500 MHz, CDCl$_3$/CD$_3$OD 3:1) δ 0.88 (t, J=6.9 Hz, 6H), 1.23-1.42 (m, 68H), 1.52-1.68 (m, 4H), 2.16-2.26 (m, 2H), 2.46 (s, 3H), 3.35-3.36 (m, 1H), 3.52-3.58 (m, 2H), 3.64 (dd, J=10.7, 4.0 Hz, 1H), 3.70-3.76 (m, 2H), 3.83-3.87 (m, 2H), 4.03-4.06 (m, 1H), 4.13-4.23 (m, 2H), 4.85 (d, J=3.4 Hz, 1H), 7.58 (d, J=8.1 Hz, 2H), 7.79 (d, J=8.1 Hz, 2H); $^{13}$C NMR (126 MHz, CDCl$_3$/CD$_3$OD 3:1) δ 14.2, 21.7, 22.9, 26.1, 29.59, 29.63, 29.7, 29.8, 29.92, 29.95, 30.04, 32.2, 32.8, 36.8, 50.4, 68.1, 68.9, 69.2, 69.6, 70.1, 72.4, 74.9, 77.8, 99.9, 128.2, 130.2, 132.8, 145.5, 174.6; HRMS (ESI): m/z calcd for C$_{57}$H$_{105}$NO$_{11}$SNa [M+Na]$^+$ 1034.7306, found 1034.7317.

Example 2.2

(2S,3S,4R)-2-Hexacosanoylamino-1-(2,3,4-tri-O-acetyl-6-O-(4-toluenesulfonyl)-α-D-galactopyranosyloxy)-3,4-di(acetyloxy)octadecane

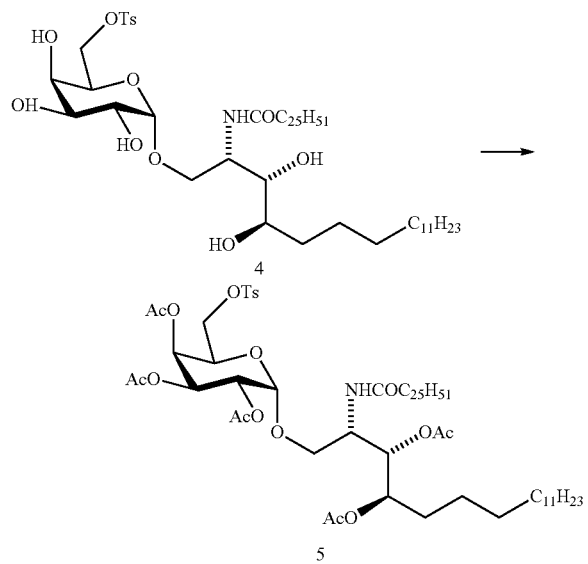

Tosylate 4 (10 mg, 9.9 μmol) is dissolved in pyridine (0.10 mL, 1.2 mmol) and cooled to 0° C. Acetic anhydride (0.10 mL, 1.0 mmol) and 4-(dimethylamino)pyridine (1.0 mg, 8.1 μmol) are then added and stirred at RT for 5 h. The product mixture is diluted with CH$_2$Cl$_2$, and is washed with 1M HCl, saturated NaHCO$_3$, brine, dried (MgSO$_4$) and the solvent removed in vacuo. Purification by silica gel chromatography (20% EtOAc/petroleum ether changing to 30% EtOAc/petroleum ether) affords the acetylated compound 5 (10 mg, 8.2 μmol, 83%) as a colourless oil. $^1$H NMR (500 MHz, CDCl$_3$) δ 0.88 (t, J=6.9 Hz, 6H), 1.22-1.33 (m, 68H), 1.62-1.75 (m, 4H), 1.97 (s, 3H), 1.99 (s, 3H), 2.05 (s, 3H), 2.07 (s, 3H), 2.08 (s, 3H), 2.23-2.29 (m, 2H), 2.45 (s, 3H), 3.37 (dd, J=10.8, 2.7 Hz, 1H), 3.62 (dd, J=10.8, 2.9 Hz, 1H), 3.98 (dd, J=10.3, J=5.9 Hz, 1H), 4.04 (dd, J=10.2, J=6.7 Hz, 1H), 4.16 (t, J=6.9 Hz, 1H), 4.36 (tt, J=9.7, 2.7 Hz, 1H), 4.87-4.90 (m, 2H), 5.10 (dd, J=10.9, 3.6 Hz, 1H), 5.23 (dd, J=9.8, 2.5 Hz, 1H), 5.29 (dd, J=10.9, 3.4 Hz, 1H), 5.41 (br d, J=2.8 Hz, 1H), 6.24 (d, J=9.7 Hz, 1H), 7.34 (d, J=8.2 Hz, 2H), 7.75 (d, J=8.2 Hz, 2H); $^{13}$C NMR (126 MHz, CDCl$_3$) δ 14.1, 20.4, 20.5, 20.6, 20.7, 20.9, 21.6, 22.6, 25.6, 25.7, 27.4, 29.27, 29.33, 29.4, 29.5, 29.6, 31.9, 36.7, 47.8, 66.6, 66.7, 67.2, 67.4, 67.6, 67.7, 70.9, 73.4, 97.2, 128.0, 129.9, 132.5, 145.1, 169.8, 169.88, 169.94, 170.5, 171.0, 172.8; HRMS (ESI): m/z calcd for C$_{67}$H$_{115}$NO$_{16}$SNa [M+Na]$^+$ 1244.7834, found 1244.7844.

Example 2.3

(2S,3S,4R)-2-Hexacosanoylamino-1-(2,3,4-tri-O-acetyl-6-deoxy-6-acetylthio-α-D-galactopyranosyloxy)-3,4-di(acetyloxy)octadecane

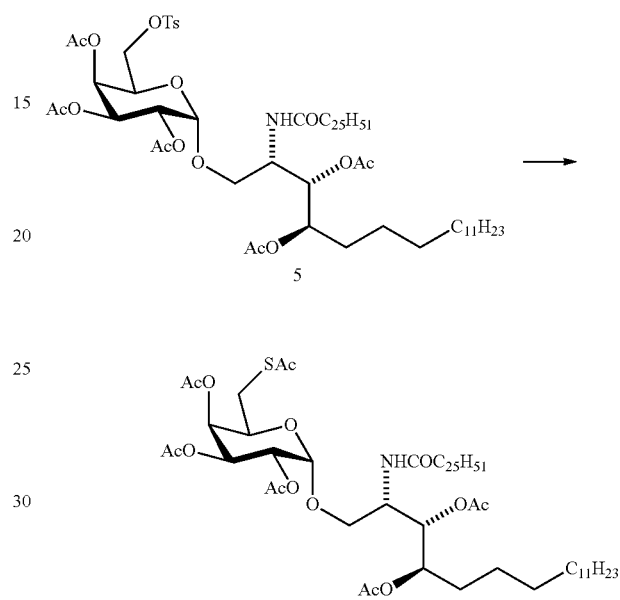

Potassium thioacetate (0.010 g, 8.2 μmol) is added to a solution of acetylated tosylate 5 (0.010 g, 8.2 μmol) stirring in anhydrous DMF (0.3 mL, 4 mmol) under Ar. The reaction mixture is heated to 80° C. and potassium thioacetate is added in aliquots until the reaction is complete by TLC (30% EtOAc/petroleum ether). Once cool, Et$_2$O and H$_2$O are added, the layers are separated and the aqueous layer is extracted with Et$_2$O several times. The combined organics are washed with H$_2$O, brine, dried (MgSO$_4$) and then concentrated. Purification of the crude residue by silica gel chromatography (20% EtOAc/petroleum ether changing to 25% EtOAc/petroleum ether) affords thioacetate 6 (5 mg, 4.4 μmol, 54%). $^1$H NMR (500 MHz, CDCl$_3$) δ 0.88 (t, J=6.9 Hz, 6H), 1.21-1.35 (m, 68H), 1.55-1.66 (m, 4H), 1.986 (s, 3H), 1.989 (s, 3H), 2.06 (s, 3H), 2.09 (s, 3H), 2.15 (s, 3H), 2.24-2.28 (m, 2H), 2.32 (s, 3H), 2.85 (dd, J=13.9, 8.0 Hz, 1H), 3.08 (dd, J=13.8, 5.9 Hz, 1H), 3.38 (dd, J=10.7, 2.3 Hz, 1H), 3.67 (dd, J=10.6, 2.8 Hz, 1H), 3.89 (t, J=7.0 Hz, 1H), 4.36 (tt, J=10.0, 2.4 Hz, 1H), 4.86-4.89 (m, 2H), 5.10 (dd, J=10.9, 3.7 Hz, 1H), 5.26 (dd, J=10.2, 2.3 Hz, 1H), 5.30 (dd, J=10.9, 3.3 Hz, 1H), 5.46 (br d, J=2.6 Hz, 1H), 6.30 (d, J=9.8 Hz, 1H); $^{13}$C NMR (126 MHz, CDCl$_3$) δ 14.1, 20.5, 20.6, 20.7, 20.9, 21.6, 22.6, 25.6, 25.7, 27.2, 28.8, 29.28, 29.34, 29.4, 29.7, 29.6, 30.4, 31.9, 36.7, 47.7, 67.2, 67.6, 67.7, 67.9, 69.0, 70.5, 73.5, 97.0, 169.6, 170.1, 170.2, 170.7, 171.1, 172.9, 194.5; HRMS (ESI): m/z calcd for C$_{62}$H$_{111}$NO$_{14}$SNa [M+Na]$^+$ 1148.7623, found 1148.7627.

Example 2.4

6,6'-Disulfanediylbis[6-deoxy-1-((2S,3S,4R)-3,4-dihydroxy-2-(hexacosanoylamino)octadecyl)-α-D-galactopyranose]

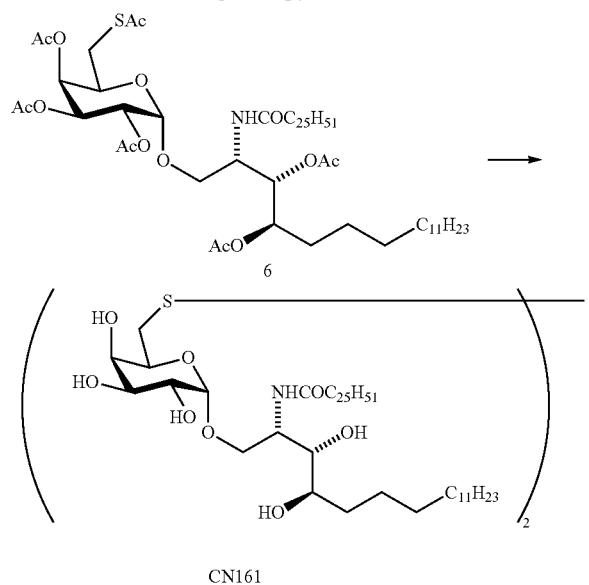

Sodium methoxide (30% in MeOH; 5.0 μL, 0.027 mmol) is added to compound 6 (4.00 mg, 3.55 μmol) stirring in anhydrous $CH_2Cl_2$:MeOH (0.5 mL; 1:1) under Ar at RT for 24 h. TLC analysis (12% MeOH/$CHCl_3$) during this time showed the presence of the target material, although this is not always reproducible. The product mixture is concentrated and purified by silica gel chromatography (100% $CHCl_3$ changing to 20% MeOH/$CHCl_3$) to yield target thiol CN161 as the disulfide (2 mg, 2.3 μmol, 64%) as a white solid. $^1H$ NMR (500 MHz, $CDCl_3$/$CD_3OD$ 3:1) δ 0.89 (t, J=7.0 Hz, 6H), 1.23-1.41 (m, 68H), 1.51-1.69 (m, 4H), 2.20-2.23 (m, 2H), 3.00 (d, J=6.7 Hz, 2H), 3.54-3.59 (m, 2H), 3.65-3.68 (m, 1H), 3.74-3.79 (m, 3H), 3.90 (br d, J=2.5 Hz, 1H), 3.93 (dd, J=10.7, 4.7 Hz, 1H), 3.97 (dd, J=6.9, 6.8 Hz, 1H), 4.20-4.23 (m, 1H), 4.89 (d, J=3.4 Hz, 1H); $^{13}C$ NMR (126 MHz, $CDCl_3$/$CD_3OD$ 3:1) 14.2, 22.9, 26.1, 26.2, 29.6, 29.67, 29.72, 29.9, 30.0, 32.2, 32.8, 36.8, 40.22, 50.5, 67.9, 69.0, 69.7, 70.4, 70.6, 72.4, 75.0, 99.9, 174.6; HRMS (ESI): m/z calcd for $C_{50}H_{99}NO_8SNa$ [M+Na]$^+$ 896.6989, found 896.7007. MS on CN161 is obtained in the presence of reducing agent DTT.

Example 2.5

(2S,3S,4R)-1-(6-Deoxy-6-mercapto-α-D-galactopyranosyloxy)-2-hexacosanoylamino-3,4-octadecandiol (CN237)

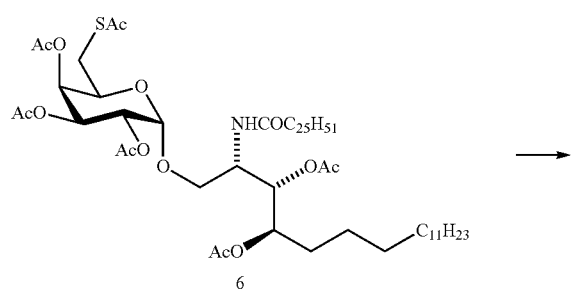

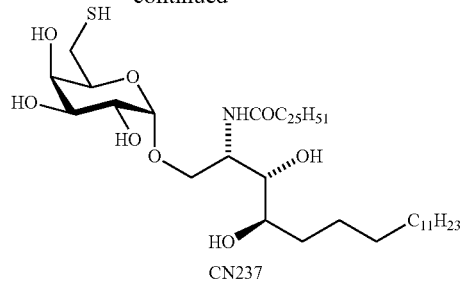

Sodium methoxide (0.5 M in MeOH; 500 μL, 0.25 mmol) is added to compound 6 (130 mg, 0.115 mmol) stirring in anhydrous $CH_3Cl$:MeOH (2:1, 6 mL) under Ar at RT for 1 h. Formic acid (100 μL) is added, the product mixture concentrated and purified by silica gel chromatography (100% $CHCl_3$ changing to 20% MeOH/$CHCl_3$) to yield target thiol CN237 (74 mg, 0.083 mmol, 72%) as a white solid. $^1H$ NMR (500 MHz, $CDCl_3$/$CD_3OD$ 3:1) δ 0.88 (t, J=7.1 Hz, 6H), 1.23-1.33 (m, 68H), 1.50-1.69 (m, 4H), 2.21 (td, J=8.0, 2.3 Hz, 2H), 2.66 (dd, J=13.7, 6.5 Hz, 1H), 2.79 (dd, J=13.7, 7.6 Hz, 1H), 2.79-3.59 (m, 4H), 3.68-3.79 (m, 5H), 3.94 (dd, J=10.5, 4.5 Hz, 1H), 3.99-4.01 (m, 1H), 4.18-4.23 (m, 1H), 4.89 (d, J=3.8 Hz, 1H) 7.17 (d, J=8.5 Hz, 1H); $^{13}C$ NMR (126 MHz, $CDCl_3$/$CD_3OD$ 3:1) δ 14.8, 23.4, 25.3, 26.7, 30.1, 30.2, 30.4, 30.5, 32.7, 33.4, 37.4, 50.9, 68.5, 69.6, 70.2, 71.2, 73.0, 73.4, 75.5, 100.4, 175.0; HRMS (ESI): m/z calcd for $C_{50}H_{99}NO_8SNa$ [M+Na]$^+$ 896.6989, found 896.6997.

Example 3

Synthesis of (2S,3S,4R)-1-(4,6-Anhydro-α-D-galactopyranosyloxy)-2-hexacosanoylamino-3,4-octadecandiol (CN154)

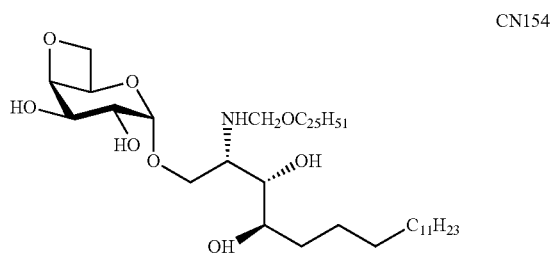

Example 3.1

(2S,3S,4R)-1-(4,6-Anhydro-2,3-di-O-benzyl-α-D-galactopyranosyloxy)-3,4-di(benzyloxy)-2-(hexacosanoylamino)octadeca-6-ene

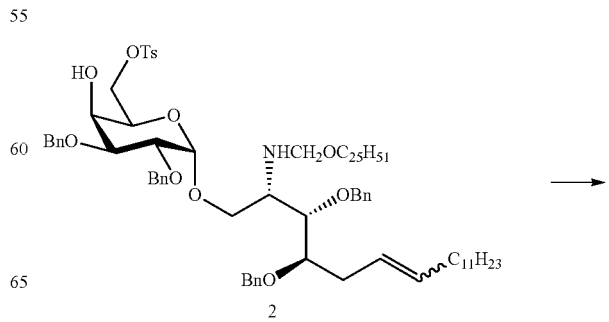

-continued

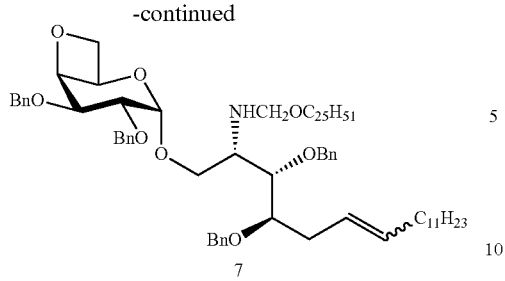

7

-continued

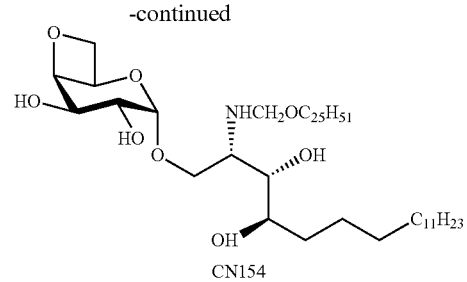

CN154

Tosylated galactose 2 (0.029 g, 0.021 mmol) is dissolved in anhydrous Et$_2$O (0.3 mL) under an Ar atmosphere and cooled to 0° C. Sodium hydride (0.002 g, 0.042 mmol; 60% dispersion in mineral oil) is then added and the reaction mixture left to warm to RT over 18 h. After this time, the mixture is warmed to 25° C. and NaH added in aliquots to push the reaction to completion. Once all the starting material is consumed (TLC), the mixture is diluted with EtOAc and H$_2$O added. The layers are separated and the aqueous layer re-extracted with EtOAc. The combined organics were washed with H$_2$O, brine, dried (MgSO$_4$) and the solvent removed in vacuo. Purification of the resulting residue by silica gel chromatography (23% EtOAc/petroleum ether changing to 30% EtOAc/petroleum ether) afforded the target material 7 as a colourless oil (0.019 g, 0.016 mmol, 54%).

$[\alpha]_D^{20}$=+27.1 (c 0.0095, CHCl$_3$); $^1$H NMR (500 MHz, CDCl$_3$) δ 0.86-0.89 (m, 6H), 1.21-1.33 (m, 62H), 1.42-1.48 (m, 2H), 1.83-1.86 (m, 2H), 2.00-2.04 (m, 2H), 2.38-2.50 (m, 2H), 3.56 (dt, J=6.4, 4.8 Hz, 1H), 3.66-3.70 (m, 2H), 3.81 (dd, J=9.4, 5.1 Hz, 1H, H-3), 3.85 (dd, J=10.4, 4.6 Hz, 1H), 4.03 (dd, J=9.5, 2.7 Hz, 1H), 4.08 (d, J=7.3 Hz, 1H), 4.30-4.34 (m, 1H), 4.36 (td, J=3.9, 1.5 Hz, 1H), 4.47 (d, J=11.6 Hz, 2H), 4.58 (d, J=11.6 Hz, 1H), 4.63-4.67 (m, 3H), 4.69 (d, J=11.8 Hz, 1H), 4.70 (d, J=11.8 Hz, 1H), 4.84 (d, J=11.8 Hz, 1H), 4.88 (d, J=2.6 Hz, 1H), 5.09 (t, J=4.5 Hz, 1H), 5.42-5.51 (m, 2H), 5.56 (d, J=8.6 Hz, 1H), 7.23-7.36 (m, 20H); $^{13}$C NMR (126 MHz, CDCl$_3$) δ 14.1 (CH$_3$), 22.7, 23.3, 23.8, 24.7, 25.7, 27.6, 28.1, 29.3, 29.4, 29.7, 31.9, 36.6, 36.7, 50.1, 67.8, 69.4, 71.7, 72.0, 73.4, 73.7, 74.1, 74.8, 77.7, 78.1, 79.2, 80.0, 98.9, 125.1, 127.6, 127.72, 127.77, 127.82, 128.3, 128.36, 128.43, 132.3, 138.3, 138.4, 138.5, 172.7; HRMS (ESI): m/z calcd for C$_{78}$H$_{120}$NO$_8$ [M+H]$^+$ 1198.9014, found 1198.9014; m/z calcd for C$_{78}$H$_{119}$NO$_8$Na [M+Na]$^+$ 1220.8833, found 1220.8818.

Example 3.2

(2S,3S,4R)-1-(4,6-Anhydro-α-D-galactopyranosyloxy)-2-hexacosanoylamino-3,4-octadecandiol (CN154)

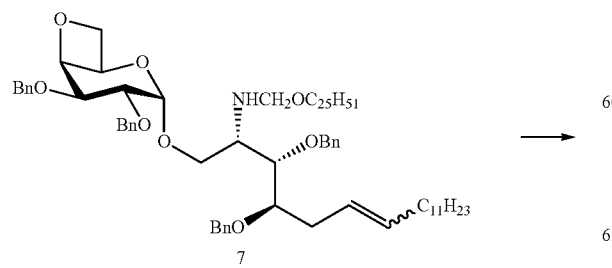

7

Pd(OH)$_2$ on carbon (20% Pd; ~5 mg) is added to protected oxetane 7 (19 mg, 16 μmol) stirring in anhydrous CH$_2$Cl$_2$:MeOH (4 mL; 1:1). The reaction vessel is evacuated and flushed with hydrogen (×4) and stirred at 25° C. for 20 hrs. Once cooled, the product mixture is filtered through celite, washed repeatedly with CHCl$_3$:MeOH (3:1), and then concentrated. Purification by silica gel chromatography (100% CHCl$_3$ changing to 10% MeOH/CHCl$_3$) yielded the target oxetane CN154 as a white solid (6 mg, 7 μmol, 44%).

$[\alpha]_D^{20}$=+66.0 [c 0.0025, CHCl$_3$:MeOH (3:1)]; $^1$H NMR (500 MHz, CDCl$_3$/CD$_3$OD 3:1) δ 0.88 (t, J=7.0 Hz, 6H), 1.52-1.68 (m, 76H), 2.18-2.21 (m, 2H), 3.50-3.56 (m, 2H), 3.68 (dd, J=10.7, 4.0 Hz, 1H), 3.71 (br s, 1H), 3.77 (dd, J=9.6, 5.2 Hz, 1H), 3.87 (dd, J=10.6, 5.0 Hz, 1H), 3.98 (dd, J=9.6, 2.8 Hz, 1H), 4.14-4.18 (m, 2H), 4.48 (td, J=3.9, 1.5 Hz, 1H), 4.78 (dd, J=7.3, 3.8 Hz, 1H), 4.99 (d, J=2.8 Hz, 1H), 5.08 (t, J=4.6 Hz, 1H); $^{13}$C NMR (126 MHz, CDCl$_3$/CD$_3$OD 3:1) δ 14.1, 22.9 26.1, 29.5, 29.6, 29.9, 32.1, 32.7, 36.7, 50.4, 67.36, 67.43, 69.5, 70.7, 72.2, 74.7, 75.4, 80.5, 100.2, 174.5; HRMS (ESI): m/z calcd for C$_{50}$H$_{97}$NO$_8$Na [M+Na]$^+$ 862.74112, found 862.7109.

Example 4

(2S,3S,4R)-1-(6-Deoxy-6-carboxymethylthio-α-D-galactopyranosyloxy)-2-hexacosanoylamino-3,4-octadecandiol (CN224)

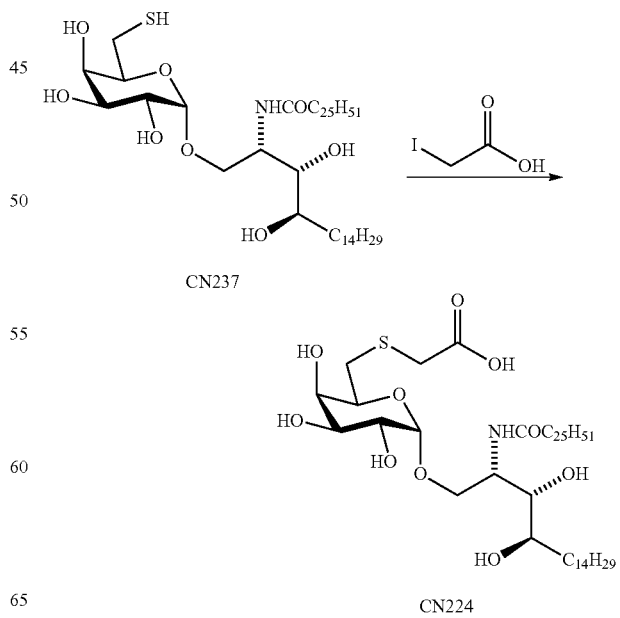

Iodoacetic acid (2.0 mg, 0.011 mmol) is added to CN237 (5.2 mg, 0.0059 mmol) and triethylamine (10 μL, 0.072 mmol) stirring in anhydrous DMF (5 mL) under Ar. The solution was heated to 70 C for 2 h. TLC analysis (10% MeOH/CHCl$_3$) during this time showed the presence of the target material. The product mixture is concentrated and purified by silica gel chromatography (100% CHCl$_3$ changing to 20% MeOH/CHCl$_3$ with 1% formic acid) to yield target acid CN224 (3 mg, 0.0032 mmol, 56%) as a white solid. $^1$H NMR (500 MHz, CDCl$_3$/CD$_3$OD 3:1) δ 0.88 (t, J=7.0 Hz, 6H), 1.22-1.42 (m, 68H), 1.49-1.71 (m, 4H), 2.18-2.25 (m, 2H), 2.80-2-95 (m, 2H), 3.20-3.30 (m, 2H), 3.56-3.63 (m, 2H), 3.65-3.71 (m, 1H), 3.72-3.80 (m, 2H) 3.90-4.03 (m, 3H), 4.20-4.24 (m, 1H), 4.85 (d, J=2.6 Hz, 1H); HRMS (ESI): m/z calcd for C$_{52}$H$_{101}$NO$_{10}$SNa [M+Na]$^+$ 954.7044, found 954.7039.

Example 5

2S,3S,4R)-1-(6-Deoxy-6-((4-iodo-N-phenylmaleimid-3-yl)thio)-α-D-galactopyranosyloxy)-2-hexacosanoylamino-3,4-octadecandiol (CN170)

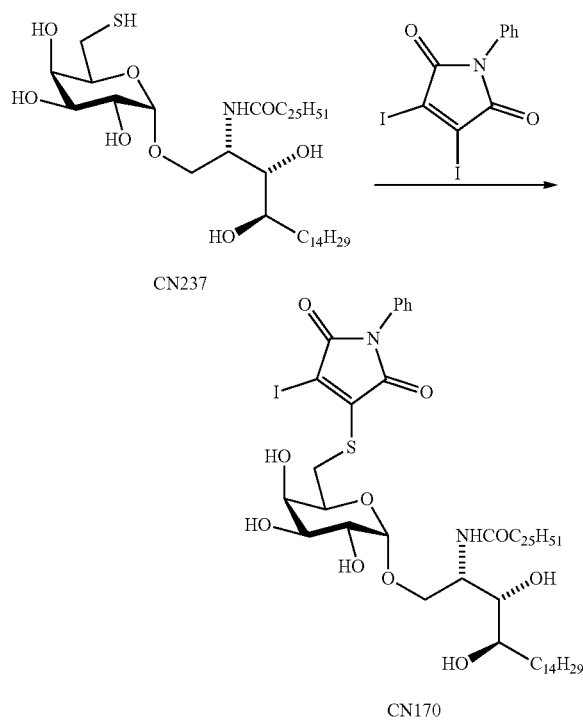

Triethylamine (30 μL, 0.22 mmol) is added to 3,4-diiodo-N-phenylmaleimide (50 mg, 0.12 mmol) and CN237 (10 mg, 0.011 mmol) stirring in anhydrous CHCl$_3$/MeOH (1:1, 5 mL) under Ar at RT. After 60 min. the product mixture is concentrated and purified by silica gel chromatography (100% CHCl$_3$ changing to 30% MeOH/CHCl$_3$) to yield the target compound CN170 (10 mg, 0.0085 mmol, 77%) as a yellow solid. $^1$H NMR (500 MHz, CDCl$_3$/CD$_3$OD 3:1) δ 0.88 (t, J=6.8 Hz, 6H), 1.20-1.38 (m, 68H), 1.48-1.68 (m, 4H), 2.16 (td, J=7.7, 2.6 Hz, 2H), 3.38 (bt, J=1.5 Hz, 1H), 3.40-3.55 (m, 2H), 3.85 (dd, J=10.7, 3.9 Hz, 2H), 3.67-3.74 (m, 2H), 3.79 (dd, J=10.0, 3.9 Hz, 1H), 3.93 (dd, J=10.8, 5.3 Hz, 1H), 3.96-3.95 (m, 1H), 4.01 (t, J=6.5 Hz, 1H), 4.20 (q, J=4.5 Hz, 1H), 4.91 (d, J=3.8 Hz, 1H), 7.30-7.40 (m, 3H), 7.44-7.49 (m, 3H); $^{13}$C NMR (126 MHz, CDCl$_3$/CD$_3$OD 3:1) δ 14.2 (CH$_3$), 22.8 (CH$_2$), 26.0 (CH$_2$), 29.5 (CH$_2$), 29.6 (CH$_2$), 29.9 (CH$_2$), 32.1 (CH$_2$), 32.3 (CH$_2$), 33.0 (CH$_2$) 36.7 (CH$_2$), 50.1, 67.9, 68.8, 70.1, 70.3, 70.9, 72.4, 75.1, 95.0, 99.9, 126.4, 128.4, 129.3, 131.6, 150.8, 164.4, 165.6, 174.5 (CO) HRMS (ESI): m/z calcd for C$_{60}$H$_{103}$N$_2$O$_{10}$SINa [M+Na]$^+$ 1193.6276, found 1193.6282.

Example 6

(2S,3S,4R)-1-(6-Deoxy-6-((4-iodo-N-propargylmaleimid-3-yl)thio)-α-D-galactopyranosyloxy)-2-hexacosanoylamino-3,4-octadecandiol (CN225)

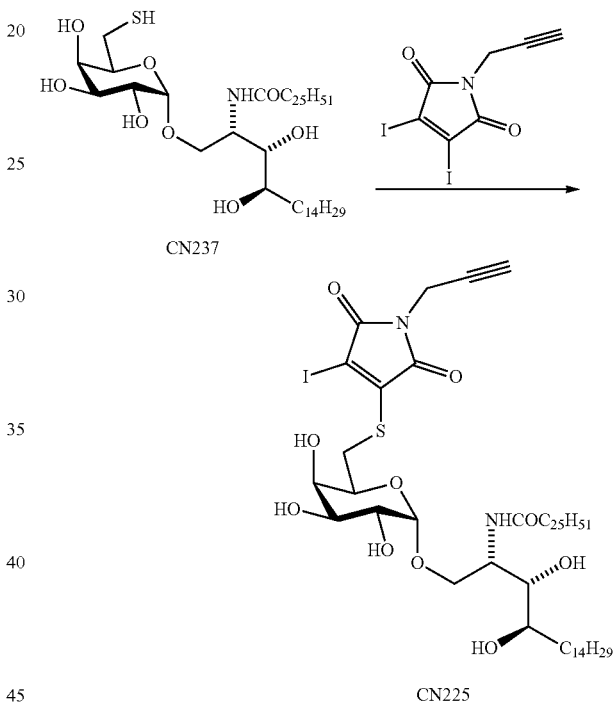

A solution of CN237 (5.0 mg, 0.0057 mmol) in CHCl$_3$/MeOH (1:1, 400 μL) is added to a stirred mixture of 3,4-diiodo-N-propargylmaleimide (16 mg, 0.041 mmol) and potassium acetate (0.60 mg, 00.61 mmol) in CHCl$_3$ (400 μL) at RT. After 60 min. the product mixture is concentrated and purified by silica gel chromatography (100% CHCl$_3$ changing to 30% MeOH/CHCl$_3$) to yield the target compound CN225 (3.0 mg, 0.0026 mmol, 46%) as a yellow solid. $^1$H NMR (500 MHz, CDCl$_3$/CD$_3$OD 3:1) δ 0.89 (t, J=7.0 Hz, 6H), 1.18-1.40 (m, 68H), 1.50-1.70 (m, 4H), 2.20 (bt, J=7.7 Hz, 2H), 2.43-2.45 (m, 1H), 2.53-3.56 (m, 2H), 3.60 (dd, J=13.8, 5.1 Hz, 1H), 3.65 (dd, J=10.5, 4.2 Hz, 1H), 3.72-3.81 (m, 3H), 3.91 (dd, J=10.8, 5.1 Hz, 1H), 3.95-4.01 (m, 2H), 4.07-4.24 (m, 3H), 4.28-4.38 (m, 2H), 4.90 (d, J=3.7 Hz, 1H), 7.38 (bt, J=8.0 Hz, 1H); $^{13}$C NMR (126 MHz, CDCl$_3$/CD$_3$OD 3:1) δ 15.1, 23.9, 27.17, 27.21, 29.4, 30.6, 30.7, 30.8, 30.9, 31.1, 33.2, 33.7, 37.8, 51.5, 68.6, 70.0, 71.4, 71.5, 72.2, 73.3, 73.4, 75.9, 78.1, 95.0, 101.0, 152.3, 165.6, 166.5, 175.6; HRMS (ESI): m/z calcd for C$_{57}$H$_{101}$N$_2$O$_{10}$NaSI [M+Na]+ 1155.6119, found 1155.6108.

Example 7

(2S,3S,4R)-1-(6-Deoxy-6-((N-propargylmaleimid-3-yl)thio)-α-D-galactopyranosyloxy)-2-hexacosanoylamino-3,4-octadecandiol (CN223)

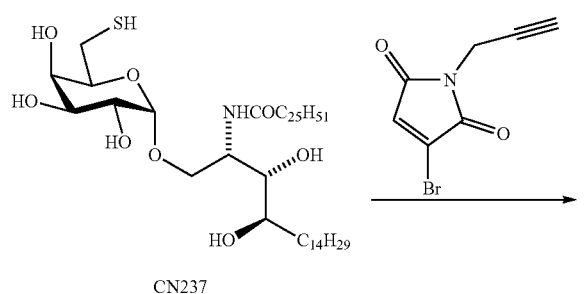

A solution of CN237 (5.0 mg, 0.0057 mmol) in CHCl$_3$/MeOH (1:1, 200 μL) is added to a stirred mixture of 3-bromo-N-propargymaleimide (3.4 mg, 0.016 mmol) and potassium acetate (0.60 mg, 0.0061 mmol) in MeOH (200 μL) at RT. After 10 hrs. the product mixture is concentrated and purified by silica gel chromatography (100% CHCl$_3$ changing to 20% MeOH/CHCl$_3$) to yield the target compound CN223 (3.0 mg, 0.0030 mmol, 52%) as a white solid. $^1$H NMR (500 MHz, CDCl$_3$/CD$_3$OD 3:1) δ 0.89 (t, J=7.2 Hz, 6H), 1.19-1.42 (m, 68H), 1.50-1.70 (m, 4H), 2.20 (td, J=7.7, 2.0 Hz, 2H), 2.37 (t, J=2.5 Hz, 1H), 3.18 (dd, J=13.3, 5.2 Hz, 1H), 3.30 (dd, J=13.3, 8.4 Hz, 1H), 3.51-3.57 (m, 2H), 3.62 (dd, J=10.7, 4.3 Hz, 1H), 3.74 (dd, J=10.0, 3.2 Hz, 1H), 3.80 (dd, J=10.1, 3.8 Hz, 1H), 3.88-3.92 (m, 2H), 4.00-4.05 (m, 3H), 4.21 (q, J=4.7, Hz, 1H), 4.28-4.38 (m, 2H), 4.91 (d, J=3.7 Hz, 1H), 6.31 (s, 1H); $^{13}$C NMR (126 MHz, CDCl$_3$/CD$_3$OD 3:1) δ 13.7, 22.5, 25.7, 25.8, 26.9, 29.2, 29.3, 29.5, 29.6, 31.8, 32.4, 50.0, 67.2, 68.5, 69.9, 70.0, 70.2, 71.5, 71.9, 74.6, 99.6, 118.2, 151.6, 166.8, 168.4, 174.3; HRMS (ESI): m/z calcd for C$_{57}$H$_{103}$N$_2$O$_{10}$S [M+H]+ 1007.7333, found 1007.7337.

Example 8

(2S,3S,4R)-1-(6-Deoxy-6-ethylthio-α-D-galactopyranosyloxy)-2-hexacosanoylamino-3,4-octadecandiol (CN227)

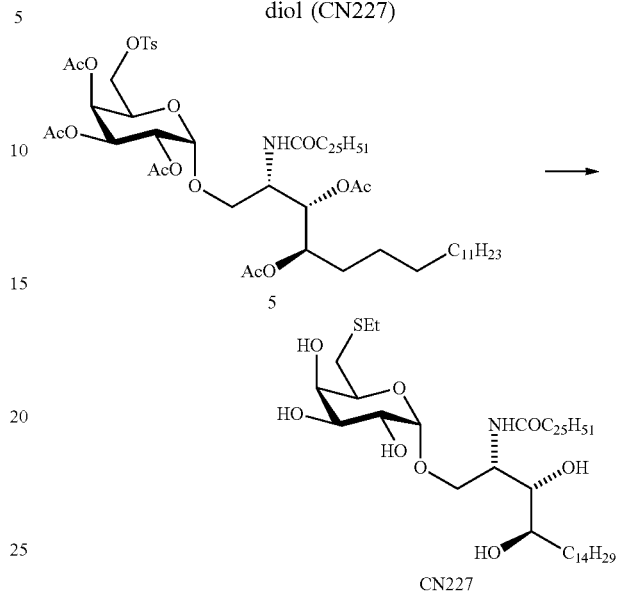

Sodium hydride (60% dispersion in mineral oil, 9.4 mg, 0.24 mmol) is added to a stirred solution of 5 (12.0 mg, 0.00981 mmol) and ethane thiol (21 μL, 0.27 mmol) in dry DMF (96 μL) under argon. After 3 days at RT the product mixture is concentrated and purified by silica gel chromatography (4% MeOH/CH$_2$Cl$_2$) changing to 10% MeOH/CH$_2$Cl$_2$) to yield the target compound CN227 (2.1 mg, 24%) as a white solid. $^1$H NMR (500 MHz, CDCl$_3$/CD$_3$OD 2:3) 0.86 (t, J=7.1 Hz, 6H), 1.23 (t, J=7.5 Hz, 3H), 1.22-1.39 (m, 68H), 1.50-1.65 (m, 4H), 2.20 (t, J=7.4, Hz, 2H), 2.58 (q, J=7.5 Hz, 2H), 2.68-2.78 (m, 2H), 2.68-2.78 (m, 2H), 3.52-3.58 (m, 2H), 3.66 (dd, J=10.6, 4.0 Hz, 1H), 3.72 (dd, J=10.0, 3.1 Hz, 1H), 3.76 (dd, J=10.0, 3.6 Hz, 1H), 3.84 (t, J=7.0 Hz, 1H), 3.88 (dd, J=10.4, 4.5 Hz, 1H), 3.90-3.92 (m, 1H), 4.20-4.16 (m, 1H), 4.84 (d, J=3.6 Hz); $^{13}$C NMR (126 MHz, CDCl$_3$/CD$_3$OD 2:3), d 14.3, 15.1, 23.3, 26.6, 26.7, 27.3, 30.0, 30.1, 30.2, 30.3, 30.4, 32.5, 32.6, 32.8, 37.1, 51.0, 67.9, 69.6, 70.9, 71.2, 71.7, 72.7, 75.0, 100.4, 175.1; HRMS (ESI): m/z calcd for C$_{52}$H$_{103}$NO$_8$SNa [M+Na]+ 924.7302, found 924.7299.

Example 9

(2S,3S,4R)-1-(6-Deoxy-6-ethylsulfinyl)-α-D-galactopyranosyloxy)-2-hexacosanoylamino-3,4-octadecandiol (CN228)

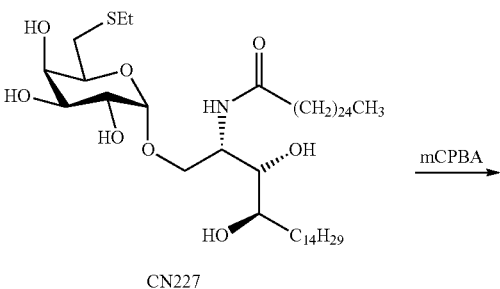

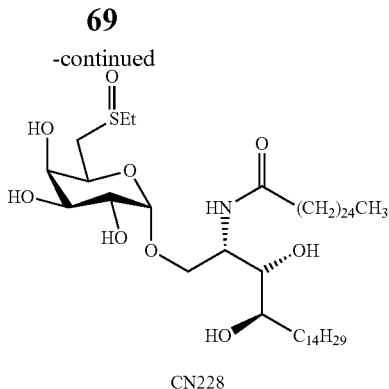

CN228

A solution of ~55% mCPBA in CH$_2$Cl$_2$ (10 mg/mL, 150 µL, 0.0048 mmol) is added to a stirred solution of CN227 (4.2 mg, 0.0047 mmol) in CH$_2$Cl$_2$/MeOH (10:1, 220 µL) cooled to −50° C. The mixture is warmed to RT over 4 hrs and diluted with CH$_2$Cl$_2$/MeOH (85:15, 20 mL) and sat aq sodium bicarbonate (20 mL). The phases are separated and the organic phase re-washed with sodium bicarbonate (2×20 mL). The organic phase is dried (MgSO$_4$) and the solvent removed in vacuo. Purification of the resulting residue by silica gel chromatography (4% MeOH/CH$_2$Cl$_2$ changing to 10% MeOH/CH$_2$Cl$_2$) afforded CN228 (0.34 mg, 8%) as a thin film. $^1$H NMR (500 MHz, CDCl$_3$/CD$_3$OD 1:1) δ 0.89 (t, J=7.0 Hz, 6H) 1.22-1.39 (m, 68H), 1.37 (t, J=7.3 Hz, 3H), 1.50-1.65 (m, 4H), 2.22 (t, J=7.5 Hz, 2H), 2.75-2.82 (m, 2H), 2.86-2.92 (m, 1H), 3.16 (dd, J=13.2, 11.2 Hz, 1H), 3.54-3.58 (m, 2H), 3.63 (dd, J=10.5, 5.2 Hz, 1H), 3.79-3.82 (m, 3H), 3.95 (dd, J=10.5, 5.4 Hz, 1H), 4.27 (dd, J=10.0, 4.9 Hz, 1H), 4.32 (bd, J=10.9 Hz, 1H), 4.90 (bs, 1H); HRMS (ESI): m/z calcd for C$_{52}$H$_{103}$NO$_9$SNa [M+Na]+ 940.7251, found 940.7244.

Example 10

(2S,3S,4R)-1-(3,6-Anhydro-α-D-galactopyranosyloxy)-2-hexacosanoylamino-3,4-octadecandiol (CN230)

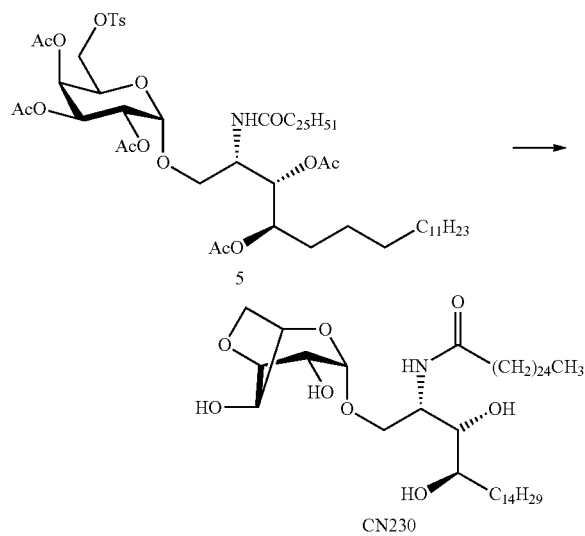

CN230

Sodium hydride (60% dispersion in mineral oil, 9.4 mg, 0.24 mmol) is added to a stirred solution of 5 (12.0 mg, 0.00981 mmol) and ethanethiol (21 µL, 0.27 mmol) in dry DMF (96 µL) under argon. After 3 days at RT the product mixture is concentrated and purified by silica gel chromatography (4% MeOH/CH$_2$Cl$_2$ changing to 10% MeOH/CH$_2$Cl$_2$) to yield a fraction containing a ~3:7 mixture of title compound CN230 and CN227. The mixture is treated with mCPBA to oxidise the thioether CN227 and repurified by silica gel chromatography to give CN230 as a white solid (1.1 mg, 13%). $^1$H NMR (500 MHz, CDCl$_3$/CD$_3$OD 2:3) δ 0.89 (t, J=7.1 Hz, 6H), 1.22-1.45 (m, 68H), 1.50-1.65 (m, 4H), 2.21 (t, J=7.5 Hz, 2H), 3.52-3.57 (m, 1H), 3.58-3.62 (m, 1H), 3.84 (dd, J=10.0, 4.3 Hz, 1H), 3.90 (dd, J=5.4, 2.4 Hz, 1H), 3.93 (dd, J=10.2, 3.7 Hz, 1H), 4.02 (dd, J=10.0, 2.4 Hz, 1H), 4.06 (d, J=10.0 Hz, 1H), 4.13-4.19 (m, 1H), 4.22-4.26 (m, 2H), 4.47-4.48 (m, 1H), 4.80 (d, J=2.5 Hz); $^{13}$C NMR (126 MHz, CDCl$_3$:CD$_3$OD 2:3) δ 14.3, 23.3, 26.6, 30.0, 30.1, 30.2, 30.3, 30.4, 32.5, 32.6, 37.1, 51.0, 69.6, 70.0, 70.6, 70.7, 73.0, 74.9, 78.4, 82.1, 97.9, 175.3; HRMS (ESI): m/z calcd for C$_{50}$H$_{97}$NO$_8$Na [M+Na]+ 862.7112, found 862.7114.

Example 11

(2S,3S,4R)-1-(6-Deoxy-6-phenylthio)-α-D-galactopyranosyloxy)-2-hexacosanoylamino-3,4-octadecandiol (CN231)

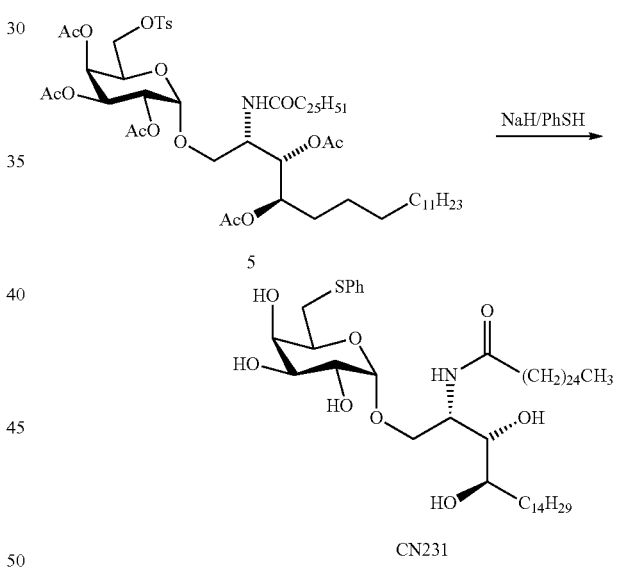

CN231

Sodium hydride (60% dispersion in mineral oil, 1.5 mg, 0.037 mmol) is added to a stirred solution of 5 (6.2 mg, 0.0051 mmol) and thiophenol (5.0 µL, 0.048 mmol) in dry DMF (50 µL) under argon. After 1 h at 65° C. the cooled reaction mixture is partitioned between ethyl acetate (1 mL) and sat aq sodium bicarbonate (1 mL). The aqueous phase is thoroughly extracted with ethyl acetate and the combined organic extracts are dried (MgSO$_4$) and concentrated at reduced pressure to afford a solid (9.2 mg). The crude material is dissolved in 2:3 CH$_2$Cl$_2$/MeOH (0.25 mL), treated with NaOMe (0.5 M in MeOH, 20 µL, 0.01 mmol) and stirred at RT for 1 h. The reaction mixture is quenched with the addition of formic acid (2 µL, 0.053 mmol), and purified by silica gel chromatography (2% MeOH/CH$_2$Cl$_2$ changing to 6% MeOH/CH$_2$Cl$_2$) to yield the target compound CN231 (3.0 mg, 62%) as a white solid. $^1$H NMR (500

MHz, CDCl$_3$/CD$_3$OD 2:3) δ 0.89 (t, J=7.1 Hz, 6H), 1.22-1.45 (m, 68H), 1.50-1.68 (m, 4H), 2.16 (t, J=7.7 Hz, 2H), 3.14-3.24 (m, 2H), 3.52-3.61 (m, 2H), 3.69 (dd, J=10.6, 3.8 Hz, 1H), 3.72 (dd, J=10.0, 3.4 Hz, 1H), 3.79 (dd, J=10.0, 3.9 Hz, 1H), 3.84 (dd, J=10.7, 4.4 Hz, 1H), 3.89-3.92 (m, 1H), 3.95-3.96 (m, 1H), 4.16-4.19 (m, 1H), 4.88 (d, J=3.9 Hz) 7.15-7.18 (m, 1H), 7.26-7.30 (m, 2H), 7.33-7.36 (m, 2H); $^{13}$C NMR (126 MHz, CDCl$_3$/CD$_3$OD 2:3) δ 14.2, 23.0, 26.3, 29.7, 29.8, 30.0, 30.1, 30.2, 32.3, 32.7, 34.2, 36.9, 50.5, 68.1, 69.2, 70.27, 70.33, 70.8, 72.5, 74.9, 100.2, 126.4, 129.1, 129.4, 136.7, 174.6; HRMS (ESI): m/z calcd for C$_{56}$H$_{103}$NO$_8$SNa [M+Na]+ 972.7302, found 972.7294.

Example 12

(2S,3S,4R)-1-(6-Deoxy-6-napthalen-2-ylthio-α-D-galactopyranosyloxy)-2-hexacosanoylamino-3,4-octadecandiol (CN236)

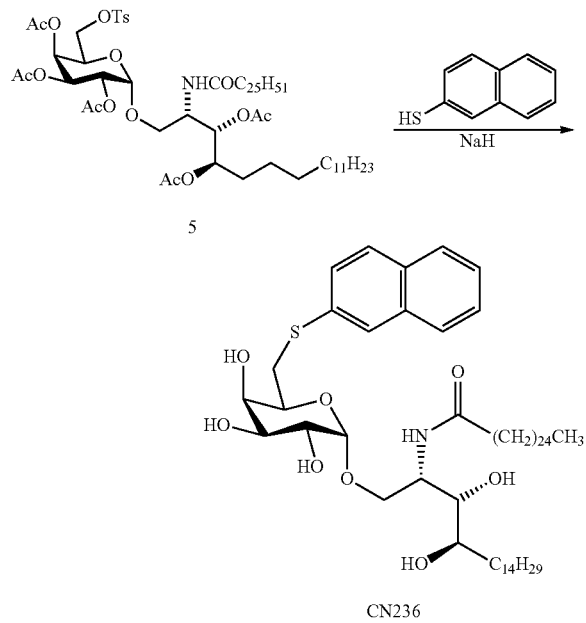

Sodium hydride (60% dispersion in mineral oil, 1.5 mg, 0.037 mmol) is added to a stirred solution of 5 (6.8 mg, 0.0056 mmol) and 2-napthalenethiol (8.6 mg, 0.053 mmol) in dry DMF (56 μL) under argon. After 1 h at 65° C. the cooled reaction mixture is partitioned between ethyl acetate (1 mL) and sat aq sodium bicarbonate (1 mL). The aqueous phase is thoroughly extracted with ethyl acetate and the combined organic extracts are dried (MgSO$_4$) and concentrated at reduced pressure to afford a solid (13.8 mg). The crude material is dissolved in 2:3 CH$_2$Cl$_2$/MeOH (0.28 mL), treated with NaOMe (0.5 M in MeOH, 22 μL, 0.011 mmol) and stirred at RT for 1 h. The reaction mixture is quenched with the addition of formic acid (2 μL, 0.053 mmol), and purified by silica gel chromatography (2% MeOH/CH$_2$Cl$_2$ changing to 6% MeOH/CH$_2$Cl$_2$) to yield the target compound CN236 (3.7 mg, 66%) as a white solid. $^1$H NMR (500 MHz, CDCl$_3$/CD$_3$OD 2:3) δ 0.89 (t, J=7.1 Hz, 6H), 1.20-1.34 (m, 68H), 1.47-1.65 (m, 4H), 2.04-2.07 (m, 2H), 3.26 (dd, J=13.6, 6.5 Hz, 1H), 3.33-3.37 (m, 1H), 3.52-3.59 (m, 2H), 3.73 (dd, J=10.2, 3.4 Hz, 1H), 3.81 (dd, J=9.9, 3.9 Hz, 1H), 3.89 (dd, J=10.5, 4.4 Hz, 1H), 3.97-4.00 (m, 2H), 4.17-4.20 (m, 1H), 4.91 (d, J=3.9 Hz, 1H), 7.40-7.49 (m, 3H), 7.73-7.80 (m, 4H); $^{13}$C NMR (126 MHz, CDCl$_3$/CD$_3$OD 2:3) δ 14.3, 23.3, 26.5, 29.9, 30.00, 30.02, 30.1, 30.31, 30.34, 30.37, 30.41, 32.6, 32.7, 34.4, 37.0, 50.9, 68.2, 69.5, 70.8, 70.9, 71.1, 72.7, 75.0, 100.5, 126.3, 126.9, 127.3, 127.5, 127.7, 128.3, 129.2, 132.6, 134.7, 134.8, 175.0; HRMS (ESI): m/z calcd for C$_{60}$H$_{105}$NO$_8$SNa [M+Na]+ 1022.7459, found 1022.7456.

Example 13

(2S,3S,4R)-1-O-[6-Deoxy-6-(2-pyridyl)disulfanyl]-α-D-galactopyranosyl)-2-hexacosanoylamino-3,4-octadecandiol (CN208)

Example 13.1

(2S,3S,4R)-1-(2,3,4-Tri-O-acetyl-[6-deoxy-6-(2-pyridyl)disulfanyl]-α-D-galactopyranosyloxy)-3,4-di(acetyloxy)-2-hexacosanoylamino-octadecaene

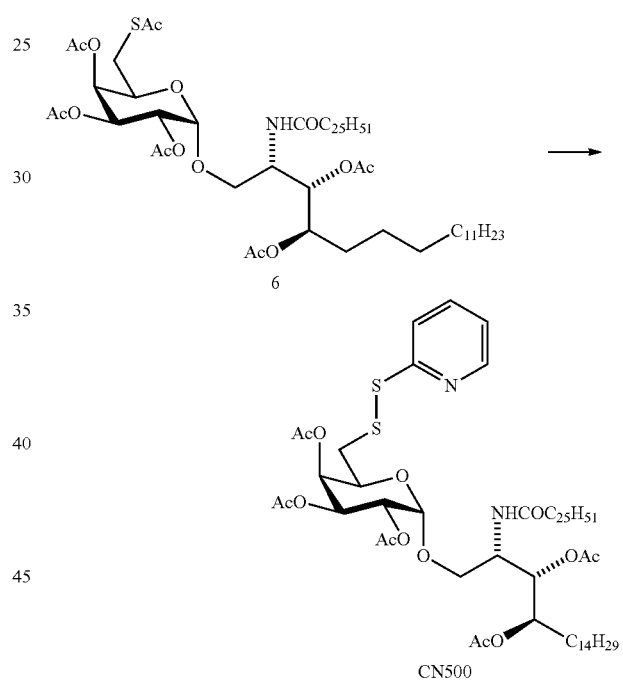

A degassed solution of hydrazine acetate (1.00 mL, 5 mg/mL, DMF/MeOH, 7:3, 0.054 mmol) is added over 2 hrs to a degassed solution of 6 (12 mg, 0.011 mmol) and 2,2'-dithiodipyridine (36 mg, 0.16 mmol) in DMF (5.5 mL). After 14 hrs at RT the mixture is diluted with CH$_2$Cl$_2$ (20 mL) and brine (sat. 20 mL). The layers are separated and the aqueous is re-extracted with EtOAc (20 mL) and the combined organic layers are dried (MgSO$_4$) and the solvent removed in vacuo. Purification of the resulting residue by silica gel chromatography (100% PE changing to 80% PE/EtOAc) afforded CN500 (4.0 mg, 31%) as a yellow solid. $^1$H NMR (500 MHz, CDCl$_3$) δ 0.88 (t, J=7.2 Hz, 6H), 1.22-1.32 (m, 68H), 1.60-1.72 (m, 4H), 1.98 (s, 3H), 1.99 (s, 3H), 2.06 (s, 3H), 2.10 (s, 3H), 2.12 (s, 3H), 2.19-2.30 (m, 2H), 2.81 (dd, J=13.7, 5.2 Hz, 1H), 2.93 (dd, J=13.7, 5.2 Hz, 1H), 3.41 (dd, J=10.7, 2.6 Hz, 1H), 3.75 (dd, J=10.7, 2.8 Hz, 1H), 4.29 (bt, J=7.0 Hz, 1H), 4.42 (tt, J=10.0, 2.8 Hz, 1H), 4.87-4.92 (m, 2H), 5.13 (dd, J=10.5, 3.7 Hz, 1H), 5.28 (dd, J=9.8, 2.2 Hz, 1H), 5.32 (dd, J=10.9, 3.5 Hz, 1H), 5.49 (br d, J=2.8 Hz, 1H), 6.40 (d, J=9.6 Hz, 1H), 7.11-7.15 (m, 1H), 7.54-7.57 (m, 1H), 7.61-7.65 (m, 1H), 8.52-8.55 (m, 1H); $^{13}$C NMR (126 MHz, CDCl$_3$) δ 14.1, 20.58, 20.63 (2×), 20.7, 21.0, 22.7, 25.7, 25.8, 27.3, 29.3, 29.4, 29.7, 31.9, 36.7, 39.1, 47.7, 67.5, 67.8, 69.4, 70.9, 73.5, 97.2, 121.0, 121.4, 137.1, 150.1, 158.7, 169.7, 170.0, 170.2, 170.7, 171.1, 172.8; HRMS (ESI): m/z calcd for C$_{65}$H$_{112}$N$_2$O$_{13}$S$_2$Na [M+Na]$^+$ 1215.7504, found 12.15.7491.

Example 13.2

(2S,3S,4R)-1-O-[6-Deoxy-6-(2-pyridyl)disulfanyl]-α-D-galactopyranosyl)-2-hexacosanoylamino-3,4-octadecandiol (CN208

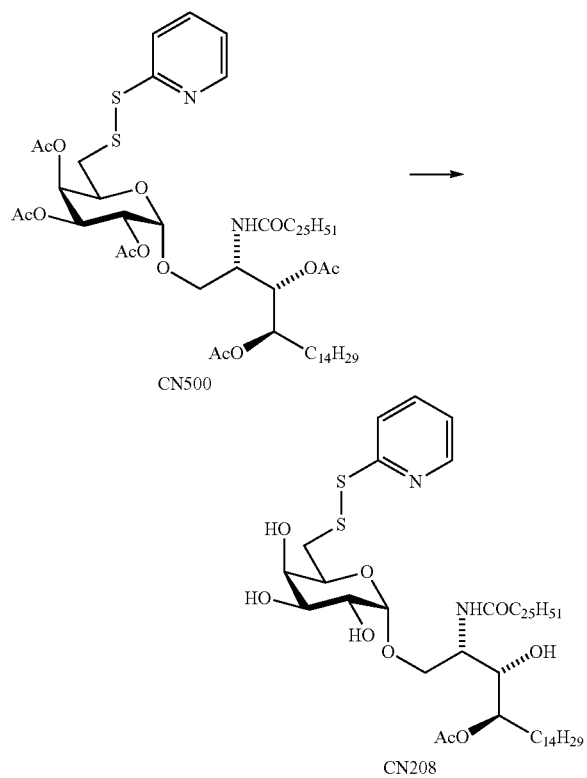

A solution of NaOMe (0.5 M, in MeOH, 40 μL, 0.020 mmol) is added to a stirred solution of CN500 (10.0 mg, 0.0083 mmol) in CHCl$_3$/MeOH (3:2, 2 mL). After 2 hrs formic acid (50 μL) was added and the mixture concentrated. Purification of the resulting residue by silica gel chromatography (100% CHCl$_3$ changing to 90% CHCl$_3$/MeOH) afforded CN208 (7.0 mg, 0.0071 mmol, 85%) as a white solid. $^1$H NMR (500 MHz, CDCl$_3$/CD$_3$OD 3:1) δ 0.88 (t, J=7.2 Hz, 6H), 1.20-1.42 (m, 68H), 1.50-1.72 (m, 4H), 2.22 (td, J=7.5, 3.3 Hz, 2H), 3.02 (dd, J=13.7, 6.1 Hz, 1H), 3.11 (dd, J=13.7, 7.5 Hz, 1H), 3.54-3.62 (m, 2H), 3.67-3.72 (m, 2H), 3.75-3.80 (m, 2H), 3.94 (dd, J=10.2, 5.0 Hz, 1H), 4.07 (t, J=6.7 Hz, 1H), 4.23 (q, J=4.9 Hz, 1H), 4.90 (d, J=3.9 Hz, 1H), 7.16-7.19 (m, 1H), 7.72-7.80 (m, 2H) 8.41-8.43 (m, 1H); $^{13}$C NMR (126 MHz, CDCl$_3$/CD$_3$OD 3:1) δ 15.2, 24.0, 27.2, 30.7, 31.0, 33.2, 34.0, 37.9, 40.8, 51.5, 69.2, 70.1, 70.5, 70.9, 71.2, 71.6, 73.4, 76.2, 101.1, 122.2, 122.6, 139.1, 150.7, 161.1, 175.6; HRMS (ESI): m/z calcd for C$_{55}$H$_{103}$N$_2$O$_8$S$_2$Na [M+Na]+ 983.7156, found 983.7156.

Example 14

(2S,3S,4R)-1-(6-Deoxy-6-((4-iodo-N-(5-azidopentyl)-maleimid-3-yl)thio)-α-D-galactopyranosyloxy)-2-hexacosanoylamino-3,4-octadecandiol (CN235)

Example 14.1

N-(5-azidopentyl)-3,4-diiodomaleimide

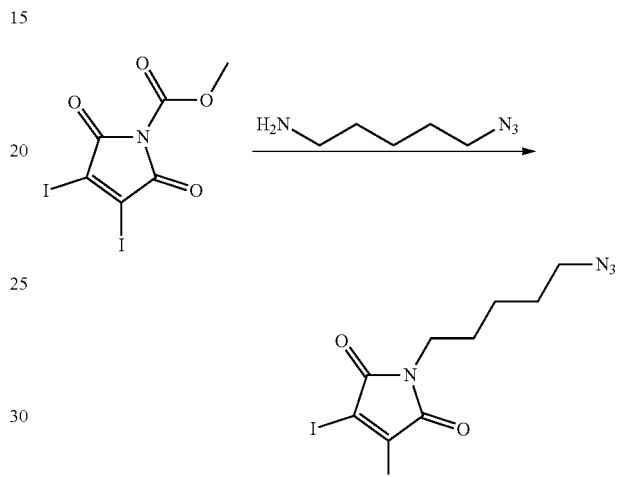

A solution of 5-azidopentan-1-amine (10 mg, 0.078 mmol) in CH$_2$Cl$_2$ (100 μL) is added to a stirred solution of N-methoxycarbonyl-3,4-diiodomaleimide (29 mg, 0.071 mmol) in CH$_2$Cl$_2$ (1 mL) at 0° C. After 20 min. the solvent removed in vacuo. Purification of the resulting residue by silica gel chromatography (100% PE changing to 70% PE/EtOAc) afforded the title compound (30 mg, 92%) as a yellow solid. $^1$H NMR (500 MHz, CDCl$_3$) δ 1.35-1.41 (m, 2H), 1.59-1.67 (m, 4H), 3.27 (t, J=6.9 Hz, 2H), 3.64 (t, J=7.2 Hz, 2H); $^{13}$C NMR (126 MHz, CDCl$_3$) δ 23.8, 28.0, 28.3, 39.9, 51.4, 117.2, 166.3; HRMS (ESI): m/z calcd for C$_9$H$_{10}$N$_4$O$_2$I$_2$Na [M+Na]+ 482.8791, found 482.8785.

Example 14.2

2S,3S,4R)-1-(6-Deoxy-6-((4-iodo-N-(5-azidopentyl)-maleimid-3-yl)thio)-α-D-galactopyranosyloxy)-2-hexacosanoylamino-3,4-octadecandiol (CN235)

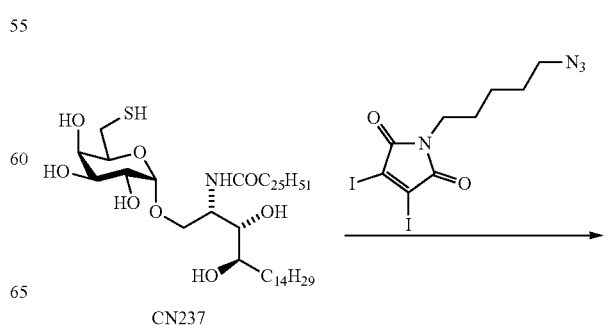

-continued

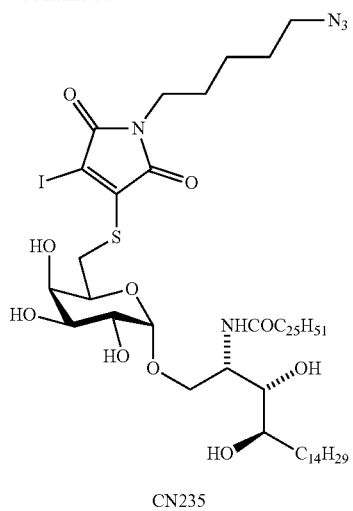

CN235

-continued

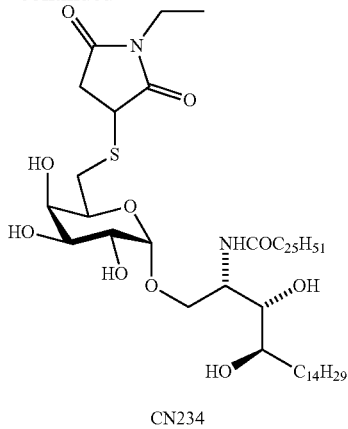

CN234

A solution of CN237 (5.0 mg, 0.0057 mmol) in CHCl₃ (1 mL) is added to a stirred mixture of N-ethylmaleimide (30 mg, 0.240 mmol) and triethylamine (10 µL). After 60 min. at RT the product mixture is concentrated and purified by silica gel chromatography (100% CHCl₃ changing to 25% MeOH/CHCl₃) to yield a diastereomeric mixture of the target compound CN234 (5.0 mg, 0.005 mmol, 87%) as a white solid. $^1$H NMR (500 MHz, CDCl₃/CD₃OD 1:1) δ 0.89 (t, J=6.9 Hz, 12H), 1.18 (t, J=7.2 Hz, 6H), 1.125-1.37 (m, 140H), 1.50-1.70 (m, 8H), 2.21 (bt, J=7.7, 4H), 2.50 (dd, J=4.0, 18.1 Hz, 1H), 2.56 (dd, J=3.6, 18.1 Hz, 1H), 2.89 (dd, J=5.5, 13.8 Hz, 1H), 2.98 (dd, J=8.3, 14.0 Hz, 1H), 3.06 (dd, J=5.5, 14.1 Hz, 1H), 3.18 (dd, J=9.1, 18.2 Hz, 1H), 3.22 (dd, J=9.1, 18.2 Hz, 1H), 3.30 (dd, J=8.2, 13.8 Hz, 1H), 3.53-3.59 (m, 8H), 3.64-3.70 (m, 2H), 3.73-3.80 (m, 4H), 3.91-4.01 (m, 8H), 4.20-4.24 (m, 2H), 4.89 (d, J=4.4 Hz, 1H), 4.90 (d, J=4.4 Hz, 1H), $^{13}$C NMR (125 MHz, CDCl₃/CD₃OD 1:1) δ 13.0, 14.3, 23.2, 26.4, 26.5, 29.8, 29.9, 30.1, 30.18, 30.22, 30.3, 32.4, 32.6, 32.7, 32.9, 33.0, 34.5, 36.5, 36.6, 36.8, 36.9, 37.01, 37.03, 40.3, 40.4, 50.86, 50.92, 67.6, 67.7, 69.3, 70.6, 70.79, 70.84, 71.8, 72.5, 75.1, 75.2, 100.1, 100.2, 174.98, 175.04, 176.0, 176.1, 177.6, 178.1; HRMS (ESI): m/z calcd for C₅₆H₁₀₇N₂O₁₀S [M+H]+ 999.7646, found 999.7657.

A solution of CN237 (5.0 mg, 0.0057 mmol) in CHCl₃ (1.2 mL) is added to a stirred mixture of N-(5-azidopentyl)-3,4-diiodomaleimide (26 mg, 0.057 mmol) and potassium acetate (0.60 mg, 0.0061 mmol) in CHCl₃ (800 µL). After 60 min. at RT the product mixture is concentrated and purified by silica gel chromatography (100% CHCl₃ changing to 30% MeOH/CHCl₃) to yield the target compound CN235 (6.0 mg, 0.0026 mmol, 87%) as a yellow solid. $^1$H NMR (500 MHz, CDCl₃/CD₃OD 3:1) δ 0.89 (t, J=6.9 Hz, 6H), 1.18-1.40 (m, 70H), 1.50-1.70 (m, 8H), 2.20 (bt, J=7.7, 2H), 3.30 (t, J=6.8 Hz, 2H), 3.53-3.61 (m, 4H), 3.62-3.66 (m, 2H), 3.70-3.81 (m, 3H), 3.90-4.00 (3H), 4.19-4.22 (m, 1H), 4.90 (d, J=3.7 Hz); $^{13}$C NMR (126 MHz, CDCl₃/CD₃OD 3:1) δ 14.3, 23.2, 24.4, 26.5, 28.6, 28.8, 29.87, 29.92, 29.98, 30.18, 30.22, 30.35, 32.4, 33.0, 37.0, 39.6, 50.7, 51.7, 63.8, 67.8, 69.3, 69.5, 70.7, 70.8, 71.4, 72.5, 75.1, 94.6, 100.3, 150.9, 166.3, 167.1, 174.8; HRMS (ESI): m/z calcd for C₅₉H₁₀₉N₅O₁₀SI [M+H]+ 1206.6940, found 1206.6946.

Example 15

(2S,3S,4R)-1-(6-Deoxy-6-(N-ethylmaleimid-3-yl)thio)-α-D-galactopyranosyloxy)-2-hexacosanoylamino-3,4-octadecandiol (CN234)

Example 16

Methyl 1-(((2S,3S,4R)-1-(6-Deoxy-)-α-D-galactopyranosyloxy)-2-hexacosanoylamino-3,4-dihydroxyoctadecandyl)-5,8,11,14,17,20,23,26,29,32,35,38,41,44,47,50,53,56,59,62,65,68,71,74-tetracosaoxa-1,2-dithiaoctaheptacontan-77-oate (CN238)

Example 16.1

Methyl 1-(pyridin-2-yldisulfanyl)-3,6,9,12,15,18,21,24,27,30,33,36,39,42,45,48,51,54,57,60,63,66,69,72-tetracosaoxapentaheptacontan-75-oate

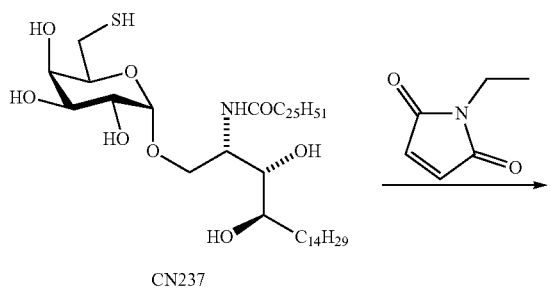

CN237

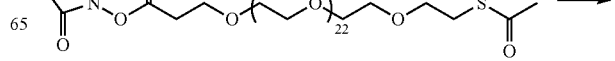

-continued

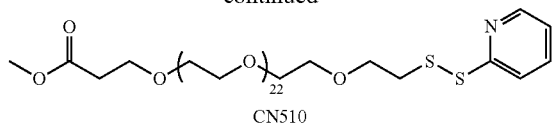

CN510

A solution of NaOMe (0.5 M, in MeOH, 100 µL, 0.05 mmol) is added to a solution of S-acetyl-dPEG$_{24}$-NHS ester (Quanta Biodesign, product #10188) (11.7 mg, 0.00898 mmol) and 2,2'-dipyridyl disulphide (25 mg, 0.113 mmol) in DMF (0.5 mL). After 2 h at RT MeOH (5 mL) is added and the solvents removed in vacuo. Purification of the resulting residue by silica gel chromatography (100% CHCl$_3$ changing to 85% CHCl$_3$/MeOH) afforded CN510 (7 mg, 0.0054 mmol, 60%) as a yellow oil. $^1$H NMR (500 MHz, CDCl$_3$/CD$_3$OD 1:1) δ 2.61 (t, J=6.3 Hz, 2H), 3.02 (t, J=6.1 Hz, 2H), 3.57-3.60 (m, 2H), 3.61-3.69 (m, 90H), 3.70 (s, 3H), 3.73 (t, J=6.1 Hz, 2H), 3.77 (t, J=6.3 Hz, 2H), 7.20 (bdd, J=4.8, 7.6 Hz, 1H), 7.80 (ddd, J=1.8, 7.6, 8.0 Hz, 1H), 7.91 (d, J=8.0 Hz, 1H), 8.39, (bd, J=4.8 Hz, 1H); $^{13}$C NMR (126 MHz, CDCl$_3$/CD$_3$OD 1:1) δ 35.4, 39.4, 52.1, 67.2, 69.4, 70.8, 70.98, 71.01, 71.05, 71.13, 71.2, 120.7, 121.7, 138.7, 149.7, 161.2, 173.3; HRMS (ESI): m/z calcd for C$_{57}$H$_{107}$NO$_{26}$S$_2$Na [M+Na]+ 1308.6420, found 1308.6423.

Example 16.2

Methyl 1-(((2S,3S,4R)-1-(6-Deoxy-)-α-D-galactopyranosyloxy)-2-hexacosanoylamino-3,4-dihydroxyoctadecandyl)-5,8,11,14,17,20,23,26,29,32,35,38,41,44,47,50,53,56,59,62,65,68,71,74-tetracosaoxa-1,2-dithiaoctaheptacontan-77-oate (CN238)

CHCl$_3$ changing to 70% CHCl$_3$/MeOH) afforded CN238 (4 mg, 0.0020 mmol, 43%) as a white solid. $^1$H NMR (500 MHz, CDCl$_3$/CD$_3$OD 9:1) δ 0.88 (t, J=6.8 Hz, 6H), 1.20-1.44 (m, 70H), 1.47-1.70 (m, 4H), 2.21 (bt, J=7.7, 2H), 2.61 (t, J=6.4 Hz, 2H), 2.87-2.92 (m, 2H), 2.95-3.04 (m, 2H), 3.51-3.56 (m, 2H), 3.62-3.69 (m, 93H), 3.70 (s, 3H), 3.73-3.80 (m, 4H), 3.89-3.99 (m, 3H), 4.19-4.23 (m, 1H), 4.88 (d, J=3.8 Hz, 1H); HRMS (ESI): m/z calcd for C$_{102}$H$_{201}$NO$_{34}$S$_2$Na [M+Na]+ 2071.3369, found 2071.3381.

Example 17

Formulating Compounds of the Invention for Intravenous Injection

Compounds of the invention are formulated analogously to reported methods for α-GalCer. Briefly, solubilisation is based on excipient proportions described by Giaccone et al (Giaccone, Punt et al. 2002). Thus, 100 µL of a 10 mg/mL solution of α-GalCer or a compound of the invention in 9:1 THF/MeOH is added to 1.78 mL of an aqueous solution of Tween 20 (15.9 mg), sucrose (177 mg) and L-histidine (23.8 mg). This homogeneous mixture is freeze dried and the resulting foam is stored under Ar at −18° C. This material is reconstituted with 1.0 mL of phosphate-buffered saline (PBS) or water prior to serial dilutions in PBS to achieve final injectable solutions of α-GalCer or compounds of the invention.

Example 18

Biological Studies

Mice.

C57BL/6 are from breeding pairs originally obtained from Jackson Laboratories, Bar Harbor, Me., and used according

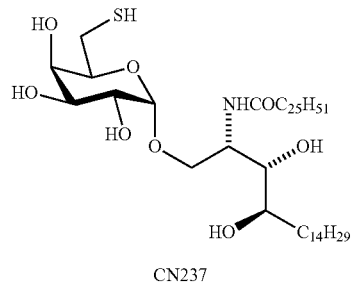

CN237

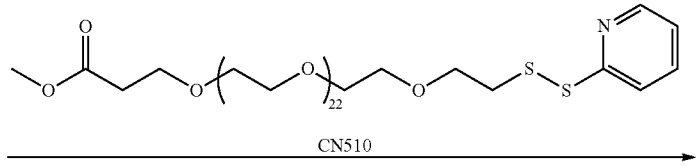

CN510

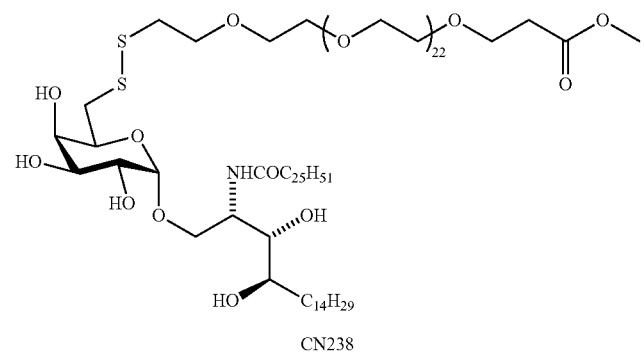

CN238

An aqueous solution of NaHCO$_3$ (1M, 30 µL) is added to a solution of CN237 (4 mg, 0.0046 mmol) and disulphide CN510 (6 mg, 0.0042 mmol) in CHCl$_3$/MeOH (1;1, 2 mL). After 1 h the reaction mixture is diluted with CHCl$_3$/MeOH (1;1, 10 mL) and the solvents removed in vacuo. Purification of the resulting residue by silica gel chromatography (100% to institutional guidelines with approval from the Victoria University of Wellington Animal Ethics Committee.

Media and Reagents

The tumour cells used (B16.OVA, C1498) are cultured in complete media consisting of Iscove's Modified Dulbecco's Medium (IMDM) supplemented with 5% FBS, 100 U/mL penicillin, 100 g/mL streptomycin, 50 M 2-mercaptoethanol.

Administration of Compounds of the Invention.

Each compound of the invention is supplied as formulated product (see example 3), and diluted in water for delivery (0.23 nmol/mouse) by intravenous injection into the lateral tail vein. In humans the expected therapeutic dose lies in the 50-4800 ($\mu g/m^2$) range (Giaccone, Punt et al. 2002). Note, 0.23 nmol in a mouse is a human equivalent dose of 30 $\mu g/m^2$ for α-GalCer.

All antibody labelling is performed on ice in FACS buffer (PBS supplemented with 1% FCS, 0.05% sodium azide, and 2 mM EDTA). Non-specific FcR-mediated antibody staining is blocked by incubation for 10 min with anti-CD16/32 Ab (24G2, prepared in-house from hybridoma supernatant). Flow cytometry is performed on a BD Biosciences FACSCalibur or BD LSRII SORP flow cytometer with data analysis using FlowJo software (Tree Star, Inc., OR, USA).

Phenotyping DC from Spleen.

Antibody staining and flow cytometry are used to examine the expression of maturation markers on dendritic cells in the spleen following injection of compounds of the invention. Splenocyte preparations are prepared by gentle teasing of splenic tissue through gauze in Iscove's Modified Dulbecco's Medium with 2 mM glutamine, 1% penicillin—streptomycin, $5\times10^{-5}$ M 2-mercapto-ethanol and 5% fetal bovine serum (all Invitrogen, Auckland, New Zealand), followed by lysis of red blood cells with RBC lysis buffer (Puregene, Gentra Systems, Minneapolis, Minn., USA). Antibody staining is performed in PBS 2% fetal bovine serum and 0.01% sodium azide. The anti-FcgRII monoclonal antibody 2.4G2 is used at 10 mg/mL to inhibit non-specific staining. Monoclonal antibodies (all BD Biosciences Pharmingen, San Jose, Calif., USA) are used to examine expression of the maturation markers CD40, CD80 and CD86 on CD11c+ dendritic cells.

Analysis of Cytokine Release into Serum.

Blood is collected from the lateral tail vein at different time intervals after glycolipid administration. Serum is collected after blood has clotted, and levels of cytokines IL-12p70, IL-4 and IFN-γ are assessed by cytokine bead array technology (Biolpex, Biorad), according to the manufacturer's instructions.

Analysis of Anti-Tumour Activity.

Groups of C57BL/6 mice (n=5) receive a subcutaneous injection into the flank of $1\times10^5$ B16.OVA melanoma cells, which express a cDNA encoding the chicken ovalbumin (OVA) sequence. The different groups are treated 7 days later, when tumours are fully engrafted, by intravenous injection of one of the following; vaccines as indicated in text and figure legends. Mice are monitored for tumour growth every 3-4 days, and tumour size for each group is calculated as the mean of the products of bisecting diameters (+SEM). Measurements are terminated for each group when the first animal develops a tumour exceeding 200 mm.

Analysis of Anti-Leukemia Activity.

To generate cell-based vaccines, C1498 acute leukemia cells are cultured for 24 h in complete IMDM supplemented with 200 ng/ml of α-GalCer or 200 ng/ml CN161, washed three times with PBS, and γ-irradiated (150 Gy). Vaccines comprising of $7.5\times10^5$ cells are administered intravenously via the lateral tail vein. Mice are monitored for onset of leukemia-associated symptoms, such as weight loss, hunching or reduced grooming. All experiments are conducted with five animals per treatment group, with controls including a leukemia-only group.

Analysis of Reactivity of Human NKT Cells to Compounds of the Invention.

Peripheral blood is drawn into heparinized tubes, diluted 1:1 in PBS, and layered over a sodium diatrizoate and polysaccharide solution (Lymphoprep; Axis-Shield, Oslo, Norway) before centrifugation at 800×g for 25 minutes at room temperature to collect the peripheral blood mononuclear cell (PBMC) fraction, which contains NKT cells. To assess proliferation of NKT cells, PBMC ($2\times10^5$ per well) are cultured at 37° C. in Iscove's Modified Dulbecco's Medium with 5% human AB serum and the indicated concentrations of α-GalCer, or CN161, with recombinant human IL-2 50 U/mL (Chiron Corporation, Emeryville, Calif.) added after 24 hours. After 7 days of culture, the cells are analysed by flow cytometry, using fluorescent soluble CD1d tetramers that have been loaded with α-GalCer to identify the NKT cells. Data are presented as percentage of NKT cells (CD1d/α-GalCer tetramer-binding cells) of total T cells (identified by binding of antibody specific for CD3) in the final cultures.

Where the foregoing description reference has been made to integers having known equivalents thereof, those equivalents are herein incorporated as if individually set forth.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

INDUSTRIAL APPLICABILITY

The invention relates to sphingoglycolipid analogues which are useful in treating or preventing diseases and conditions such as those relating to infection, atopic disorders, autoimmune diseases or cancer.

REFERENCES

Atherton, E., H. Fox, et al. (1978). "A mild procedure for solid phase peptide synthesis: use of fluorenylmethoxy-carbonylamino-acids." Journal of the Chemical Society, Chemical Communications(13): 537-539.

Baek, D. J., J.-H. Seo, et al. (2011). "The 3-Deoxy Analogue of α-GalCer: Disclosing the Role of the 4-Hydroxyl Group for CD1d-Mediated NKT Cell Activation." *ACS Medicinal Chemistry Letters* 2(7): 544-548.

Banchet-Cadeddu, A., E. Henon, et al. (2011). "The stimulating adventure of KRN 7000." *Org Biomol Chem* 9(9): 3080-3104.

Bendelac, A., P. B. Savage, et al. (2007). "The biology of NKT cells." *Annu Rev Immunol* 25: 297-336.

Bernard, D., M. S. Ventresca, et al. (2010). "Processing of tumor antigen differentially impacts the development of helper and effector CD4+ T-cell responses." Mol Ther 18(6): 1224-1232.

Bettinotti, M. P., C. J. Kim, et al. (1998). "Stringent allele/epitope requirements for MART-1/Melan A immunodominance: implications for peptide-based immunotherapy." *J Immunol* 161(2): 877-889.

Brossart, P., K. S. Heinrich, et al. (1999). "Identification of HLA-A2-restricted T-cell epitopes derived from the MUC1 tumor antigen for broadly applicable vaccine therapies." *Blood* 93(12): 4309-4317.

Butler, R. N., C. B. O'Regan, et al. (1978). "Reactions of fatty acids with amines. Part 2. Sequential thermal reactions of stearic (octadecanoic) acid with some 1,2- and 1,3-aminoalcohols and bis-amines." *Journal of the Chemical Society, Perkin Transactions* 1(4): 373-377.

Chang, J. (2006). "Efficient amplification of melanoma-specific CD8+ T cells using artificial antigen presenting complex." *Exp Mol Med* 38(6): 591-598.

Chen, G., J. Schmieg, et al. (2004). "Efficient synthesis of alpha-C-galactosyl ceramide immunostimulants: use of ethylene-promoted olefin cross-metathesis." *Org Lett* 6(22): 4077-4080.

Ciesielski, M. J., D. Kozbor, et al. (2008). "Therapeutic effect of a T helper cell supported CTL response induced by a survivin peptide vaccine against murine cerebral glioma." *Cancer Immunol Immunother* 57(12): 1827-1835.

Davidson, E. J., R. L. Faulkner, et al. (2004). "Effect of TA-CIN (HPV 16 L2E6E7) booster immunisation in vulval intraepithelial neoplasia patients previously vaccinated with TA-HPV (vaccinia virus encoding HPV 16/18 E6E7)." *Vaccine* 22(21-22): 2722-2729.

de Araujo, A. D., J. M. Palomo, et al. (2006). "Diels-Alder ligation of peptides and proteins." *Chemistry* 12(23): 6095-6109.

Deng, S., J. Mattner, et al. (2011). "Impact of sugar stereochemistry on natural killer T cell stimulation by bacterial glycolipids." *Org Biomol Chem* 9(22): 7659-7662.

Dere, R. T. and X. Zhu (2008). "The first synthesis of a thioglycoside analogue of the immunostimulant KRN7000." *Org Lett* 10(20): 4641-4644.

Du, W., S. S. Kulkarni, et al. (2007). "Efficient, one-pot syntheses of biologically active alpha-linked glycolipids." *Chem Commun (Camb)*(23): 2336-2338.

Ebensen, T., C. Link, et al. (2007). "A pegylated derivative of alpha-galactosylceramide exhibits improved biological properties." *J Immunol* 179(4): 2065-2073.

Fields, G. B. and R. L. Noble (1990). "Solid phase peptide synthesis utilizing 9-fluorenylmethoxycarbonyl amino acids." *Int J Pept Protein Res* 35(3): 161-214.

Friedrichs, B., S. Siegel, et al. (2006). "Survivin-derived peptide epitopes and their role for induction of antitumor immunity in hematological malignancies." *Leuk Lymphoma* 47(6): 978-985.

Fujii, S., K. Shimizu, et al. (2003). "Activation of natural killer T cells by alpha-galactosylceramide rapidly induces the full maturation of dendritic cells in vivo and thereby acts as an adjuvant for combined CD4 and CD8 T cell immunity to a coadministered protein." *J Exp Med* 198 (2): 267-279.

Giaccone, G., C. J. Punt, et al. (2002). "A phase I study of the natural killer T-cell ligand alpha-galactosylceramide (KRN7000) in patients with solid tumors." *Clin Cancer Res* 8(12): 3702-3709.

Hermans, I. F., J. D. Silk, et al. (2003). "NKT cells enhance CD4+ and CD8+ T cell responses to soluble antigen in vivo through direct interaction with dendritic cells." *J Immunol* 171(10): 5140-5147.

Hermans, I. F., J. D. Silk, et al. (2004). "The VITAL assay: a versatile fluorometric technique for assessing CTL- and NKT-mediated cytotoxicity against multiple targets in vitro and in vivo." *J Immunol Methods* 285(1): 25-40.

Hong, S., M. T. Wilson, et al. (2001). "The natural killer T-cell ligand alpha-galactosylceramide prevents autoimmune diabetes in non-obese diabetic mice." *Nat Med* 7(9): 1052-1056.

Huarte, E., P. Sarobe, et al. (2002). "Enhancing immunogenicity of a CTL epitope from carcinoembryonic antigen by selective amino acid replacements." *Clin Cancer Res* 8(7): 2336-2344.

Jager, E., H. Hohn, et al. (2002). "Peptide-specific CD8+ T-cell evolution in vivo: response to peptide vaccination with Melan-A/MART-1." *Int J Cancer* 98(3): 376-388.

Johansen, S. K., H. T. Kornø, et al. (1999). "Synthesis of carbasugars from aldonolactones: Ritter-type epoxide opening in the synthesis of polyhydroxylated aminocyclopentanes." *Synthesis* 1999(01): 171-177.

Karbach, J., S. Gnjatic, et al. (2010). "Tumor-reactive CD8+ T-cell responses after vaccination with NY-ESO-1 peptide, CpG 7909 and Montanide ISA-51: association with survival." *Int J Cancer* 126(4): 909-918.

Kawano, T., J. Cui, et al. (1997). "CD1d-restricted and TCR-mediated activation of valpha14 NKT cells by glycosylceramides." *Science* 278(5343): 1626-1629.

Kinjo, Y., P. Illarionov, et al. (2011). "Invariant natural killer T cells recognize glycolipids from pathogenic Gram-positive bacteria." *Nature Immunology*: 1-10.

Lee, A., K. J. Farrand, et al. (2006). "Novel synthesis of alpha-galactosyl-ceramides and confirmation of their powerful NKT cell agonist activity." *Carbohyd Res* 341 (17): 2785-2798.

Levy, A., J. Pitcovski, et al. (2007). "A melanoma multi-epitope polypeptide induces specific CD8+ T-cell response." *Cell Immunol* 250(1-2): 24-30.

Li, Y., E. Girardi, et al. (2010). "The Vα14 invariant natural killer T cell TCR forces microbial glycolipids and CD1d into a conserved binding mode." *J Exp Med* 207(11): 2383-2393.

Li, Z., Y. Oka, et al. (2008). "Identification of a WT1 protein-derived peptide, WT1, as a HLA-A 0206-restricted, WT1-specific CTL epitope." *Microbiol Immunol* 52(11): 551-558.

Lu, X.-L., Z.-H. Liang, et al. (2006). "Induction of the Epstein-Barr Virus Latent Membrane Protein 2 Antigen-specific Cytotoxic T Lymphocytes Using Human Leukocyte Antigen Tetramer-based Artificial Antigen-presenting Cells." *Acta Biochimica et Biophysica Sinica* 38(3): 157-163.

Lu, X., L. Song, et al. (2006). "Synthesis and evaluation of an alpha-C-galactosylceramide analogue that induces Th1-biased responses in human natural killer T cells." *Chembiochem* 7(11): 1750-1756.

Majireck, M. M. and S. M. Weinreb (2006). "A study of the scope and regioselectivity of the ruthenium-catalyzed [3+2]-cycloaddition of azides with internal alkynes." *J Org Chem* 71(22): 8680-8683.

Morita, M., K. Motoki, et al. (1995). "Structure-activity relationship of alpha-galactosylceramides against B16-bearing mice." *J Med Chem* 38(12): 2176-2187.

Motoki, K., M. Morita, et al. (1995). "Immunostimulatory and antitumor activities of monoglycosylceramides having various sugar moieties." *Biol Pharm Bull* 18(11): 1487-1491.

Noppen, C., F. Levy, et al. (2000). "Naturally processed and concealed HLA-A2.1-restricted epitopes from tumor-associated antigen tyrosinase-related protein-2." *Int J Cancer* 87(2):

Parekh, V. V., M. T. Wilson, et al. (2005). "Glycolipid antigen induces long-term natural killer T cell anergy in mice." *J Clin Invest* 115(9): 2572-2583.

Park, J. J., J. H. Lee, et al. (2008). "Synthesis of all stereoisomers of KRN7000, the CD1d-binding NKT cell ligand." *Bioorg Med Chem Lett* 18(14): 3906-3909.

Plettenburg, O., V. Bodmer-Narkevitch, et al. (2002). "Synthesis of alpha-galactosyl ceramide, a potent immunostimulatory agent." *J Org Chem* 67(13): 4559-4564.

Pu, J. and R. W. Franck (2008). "C-Galactosylceramide diastereomers via sharpless asymmetric epoxidation chemistry." *Tetrahedron* 64(37): 8618-8629.

Raju, R., B. F. Castillo, et al. (2009). "Synthesis and evaluation of 3"- and 4"-deoxy and -fluoro analogs of the immunostimulatory glycolipid, KRN7000." *Bioorg Med Chem Lett* 19(15): 4122-4125.

Rostovtsev, V. V., L. G. Green, et al. (2002). "A stepwise huisgen cycloaddition process: copper(I)-catalyzed regioselective "ligation" of azides and terminal alkynes." *Angew Chem Int Ed Engl* 41(14): 2596-2599.

Sakurai, K. and D. Kahne (2010). "Design and Synthesis of Functionalized Trisaccharides as p53-Peptide Mimics." *Tetrahedron Lett* 51(29): 3724-3727.

Saxon, E. and C. R. Bertozzi (2000). "Cell surface engineering by a modified Staudinger reaction." *Science* 287 (5460): 2007-2010.

Schmitz, M., P. Diestelkoetter, et al. (2000). "Generation of survivin-specific CD8+ T effector cells by dendritic cells pulsed with protein or selected peptides." *Cancer Res* 60(17): 4845-4849.

Silk, J. D., I. F. Hermans, et al. (2004). "Utilizing the adjuvant properties of CD1d-dependent NK T cells in T cell-mediated immunotherapy." *J Clin Invest* 114(12): 1800-1811.

Speiser, D. E. and P. Romero (2010). "Molecularly defined vaccines for cancer immunotherapy, and protective T cell immunity." *Semin Immunol* 22(3): 144-154.

Tashiro, T., R. Nakagawa, et al. (2008). "RCAI-61, the 6'-O-methylated analog of KRN7000: its synthesis and potent bioactivity for mouse lymphocytes to produce interferon-γ in vivo." *Tetrahedron Lett* 49(48): 6827-6830.

Trappeniers, M., S. Goormans, et al. (2008). "Synthesis and in vitro evaluation of alpha-GalCer epimers." *Chem Med Chem* 3(7): 1061-1070.

Tupin, E., A. Nicoletti, et al. (2004). "CD1d-dependent activation of NKT cells aggravates atherosclerosis." *J Exp Med* 199(3): 417-422.

Uchimura, A., T. Shimizu, et al. (1997). "Immunostimulatory activities of monoglycosylated α-d-pyranosylceramides." *Bioorg Med Chem* 5(12): 2245-2249.

Veerapen, N., M. Brigl, et al. (2009). "Synthesis and biological activity of alpha-galactosyl ceramide KRN7000 and galactosyl (alpha1->2) galactosyl ceramide." *Bioorg Med Chem Lett* 19(15): 4288-4291.

Widdison, W. C., S. D. Wilhelm, et al. (2006). "Semisynthetic maytansine analogues for the targeted treatment of cancer." *J Med Chem* 49(14): 4392-4408.

Wingender, G., P. Rogers, et al. (2011). "Invariant NKT cells are required for airway inflammation induced by environmental antigens." *J Exp Med* 208(6): 1151-1162.

Wipf, P. and J. G. Pierce (2006). "Expedient synthesis of the alpha-C-glycoside analogue of the immunostimulant galactosylceramide (KRN7000)." *Org Lett* 8(15): 3375-3378.

Wu, T.-N., K.-H. Lin, et al. (2011). "Avidity of CD1d-ligand-receptor ternary complex contributes to T-helper 1 (Th1) polarization and anticancer efficacy." *Proc Natl Acad Sci USA* 108(42): 17275-17280.

Zeng, D., Y. Liu, et al. (2003). "Activation of natural killer T cells in NZB/W mice induces Th1-type immune responses exacerbating lupus." *J Clin Invest* 112(8): 1211-1222.

Bach, T., K. Kather et al. (1998). "Synthesis of five-, six-, and seven-membered heterocycles by intramolecular ring opening reactions of 3-oxetanol derivatives." *J Org Chem* 63(6): 1910-1918.

Bahrami, K., M. M. Khodaei, et al. (2009). "Direct conversion of thiols to sulfonyl chlorides and sulphonamides." J Org Chem 74(24): 9287-9291.

Banwell, M. G., M. T. Jones et al. (2010). "A Pd[0]-catalyzed Ullmann cross-coupling/reductive cyclization approach to C-3 mono-alkylated oxindoles and related compounds." *Tetrahedron* 66(47): 9252-9262.

Black, M., A. Trent, et al. (2010). "Advances in the design and delivery of peptide subunit vaccines with a focus on toll-like receptor agonists." *Expert Rev Vaccines* 9(2): 157-173

Burkhard, J. A., G. Wuitschik et al. (2010) "Oxetanes as versatile elements in drug discovery and synthesis." *Angew Chem Int Ed* 49(48): 9052-9067.

Chen, X., P. Xu et al. (2012). "Synthesis and antibacterial activity of novel modified 5-O-desosamine ketolides." *Bioorg Med Chem Lett* 22(24): 7402-7405.

Chen, X., L. Li et al. (2006). "Synthesis and biological evaluation of technetium-99m-labeled deoxyglucose derivatives as imaging agents for tumor." *Bioorg Med Chem Lett* 16(21): 5503-5506.

Dietz, H.-J., G. Rieck, et al. (1989). "Synthese neuer pyrrolidin-2,5-dione." *Zeitschrift fuer Chemie* (Stuttgart, Germany) 29(8): 284-285.

Divakar, K. J., A. Mottoh, et al. (1990) "Approaches to the synthesis of 2'-thio analogues of pyrimidine ribosides." *J Chem Soc, Perkin Transactions 1: Org Bio-Org Chem* (1972-1999) (4): 969-974.

Fascione, M. A., N. J. Webb, et al. (2012). "Stereoselective glycosylations using oxathiane spiroketal glycosyl donors." *Carbohyd Res* 348: 6-13.

Froehlich, R. F. G., E. Schrank, et al. (2012) "2,2,2-Trifluoroethyl 6-thio-β-d-glucopyranoside as a selective tag for cysteines in proteins." *Carbohyd Res* 361(x): 100-104.

Fujiwara, Y. and G. C. Fu (2011) "Application of a new chiral phosphepine to the catalytic asymmetric synthesis of highly functionalized cyclopentenes that bear an array of heteroatom-substituted quaternary stereocenters." *J Am Chem Soc* 133(31): 12293-12297.

Gal, J. L., L. Latapie et al. (2004). "Design and synthesis of a novel family of semi-rigid ligands: versatile compounds for the preparation of 99mTc radiopharmaceuticals" *Org Biomol Chem* 2(6): 876-883.

Girouard, S., M.-H. Houle et al. (2005) "Synthesis and characterization of dimaleimide fluorogens designed for specific labeling of proteins." *J Am Chem Soc* 127(2): 559-566.

Gonzalez-Temprano, I., I. Osante et al. (2004). "Enantiodivergent synthesis of pyrrolo[2,1-a]isoquinolines based on diastereoselective Parham cyclization and α-amidoalkylation reactions" *J Org Chem* 69(11): 3875-3885.

Greene, T. W. and P. G. M. Wutz (1991) "Protective groups in organic synthesis." New York, N.Y., John Wily and Sons, Inc.

Groutas, W. C., M. J. Brubaker et al. (1989) "Inhibition of human leukocyte elastase by derivatives of N-hydroxysuccinimide: a structure-activity-relationship study." J Med Chem 32(7): 1607-1611.

Howell, A. R., R. C. So, et al. (2004). "Approaches to the preparation of sphinganines." *Tetrahedron* 60(50): 11327-11347.

Isobe, H., K. Cho et al. (2007). "Synthesis of fullerene glycoconjugates via a copper-catalyzed Huisgen cycloaddition reaction." *Org Lett* 9(22): 4611-4614.

Jones, M. W., R. A. Strickland et al. (2012). "Polymeric dibromomaleimides as extremely efficient bisulfide bridging bioconjugation and pegylation agents." *J Am Chem Soc* 134(3): 1847-1852.

Joyce, R. P., J. A. Gainor et al. (1987). "Synthesis of the aromatic and monosaccharide moieties of staurosporine." *J Org Chem* 52(7): 1177-1185.

Knothe, S., V. Mutschler, et al. (2011). "The NKT cell ligand alphagalactosylceramide suppresses allergic airway inflammation by induction of a Th1 response." *Vaccine* 29(25): 4249-4255.

Kværnø, L., M. Werder et al (2005). "Synthesis and in vitro evaluation of inhibitors of intestinal cholesterol absorption." *J Med Chem* 48(19): 6035-6053.

Li, X., M. Fujio, et al. (2010). "Design of a potent CD1d-binding NKT cell ligand as a vaccine adjuvant." *Proc Natl Acad Sci USA* 107(29): 13010-13015.

Liptak, A., E. Balla, et al. (2004). "The first synthesis of secondary sugar sulfonic acids by nucleophilic displacement reactions." *Tetrahedron Lett* 45(4): 839-842

Manzo, E., A. Tramice et al. (2012). "Chemo-enzymatic preparation of a-6-sulfoquinovosyl-1,2-O-diacylglycerols." *Tetrahedron* 68(49): 10169-10175.

Moree, W. J., G. A. van der Marel et al. (1996). "Synthesis of peptidosulfinamides and peptidosulfonamides: peptidomimetics containing the sulfinamide or sulphonamide transition-state isostere." *J Org Chem* 60(16): 5157-5169.

Muus, U., D. Farnsworth, et al. (2010). "Development of antiproliferative phenylmaleimides that activate the unfolded protein response." *Bioorg Med Chem* 18(12): 4535-4541.

Muus, U., C. Hose et al. (2010). "Development of antiproliferative phenylmaleimides that activate the unfolded protein response." *Bioorg Med Chem* 18(12): 4535-4541.

O'Reilly, C. and P. V. Murphy (2011). "Synthesis of alpha-S-glycosphingolipids based on uronic acids." *Org Lett* 13(19): 5168-5171.

Obreza, A. and S. Gobec (2004). "Recent advances in design, synthesis and biological activity of aminoalkylsulfonates and sulfonamidopeptides." *Curr Med Chem* 11: 3263-3278.

Park, E.-J., Y. Kong, et al (2011). "Exploration of SAR regarding glucose moiety in novel C-aryl glucoside inhibitors of SGLT2". *Bioorg Med Chem Lett* 21(2): 742-746.

Raju, R., B. F. Castillo, et al. (2009). "Synthesis and evaluation of 3"- and 4"-deoxy and -fluoro analogs of the immunostimulatory glycolipid, KRN7000." Bioorg Med Chem Lett 19(15): 4122-4125.

Ren, X.-F., E. Turos et al. (1995). "Regiochemical and stereochemical studies on halocyclization reactions of unsaturated sulphides." *J Org Chem* 60(20): 6468-6483.

Rim, C., L. J. Lahey et al. (2009). "Thiol-ene reactions of 1,3,5-triacryloylhexahydro-1,3,5-triazine (TAT): facile access to functional tripodal thioethers." *Tetrahedron Lett* 50(7): 745-747.

Schumacher, F. F., M. Nobles et al. (2011). "In situ maleimide bridging of disulfides and a new approach to protein PEGylation" *Bioconj Chem* 22(2): 132-136.

Sherry, B. D., R. Loy, et al. (2004) "Rhenium(V)-catalyzed synthesis of 2-deoxy-α-glycosides." *J Am Chem Soc* 126(14): 4510-4511.

Smeenk L. E. J., N. Dailly et al. (2012). "Synthesis of water-soluble scaffolds for peptide cyclization, labeling, and ligation." *Org Lett* 14(5): 1194-1197.

Specha, M. (1993) "Introduction of a new class of ligands for the metal-catalyzed enantioselective synthesis." *Helvetica Chimica Acta* 76(5): 1832-1846.

Smith, M. E. B, F. F. Schumacher et al. (2010). "Protein modification, bioconjugation and disulphide bridging using bromomaleimides." *J Am Chem Soc* 132(6): 1960-1965.

Stewart, S. G., M. E. Polomska, et al. (2007). "A concise synthesis of maleic anhydride and maleimide natural products found in Antrodia camphorate." *Tetrahedron Lett* 48(13): 2241-44.

Tedaldi, L. M., A. E. Aliev et al. (2012). "[2+2] Photocycloadditions of thiomaleimides." *Chem Commun* 48(39): 4725-4727.

Trappeniers, M., S. Goormans, et al. (2008). "Synthesis and in vitro evaluation of alpha-GalCer epimers." *Chem Med Chem* 3(7): 1061-1070.

Verschueren, W. G., I. Dierynck, et al. (2005). "Design and optimization of tricyclic phtalimide analogues as novel inhibitors of HIV-1 integrase." *J Med Chem* 48(6): 1930-1940.

Weiss, S., B. Koenig et al. (2010). "NG-acyl-argininamides as NPY Y1 receptor antagonists: influence of structurally diverse acyl substituents on stability and affinity." *Bioorg Med Chem* 18(17): 6292-6304.

Wilson, R. M., R. K. Thalji et al. (2006). "Enantioselective synthesis of a PKC inhibitor via catalytic C—H bond activation." *Org Lett* 8(8): 1745-1747.

Yoshikiyo, K., H. Ohta, et al. (2008) "Complexation of a disulfide-linked α-cyclodextrin dimer with 1-alkanols." *J Mol Str* 891(1-3): 420-422.

Zhu, X. (2006) "MMTr as an efficient anomeric S-protecting group for the synthesis of glycosyl thiols." *Tetrahedron Lett* 47(45): 7935-7938.

The invention claimed is:

1. A compound of formula (I):

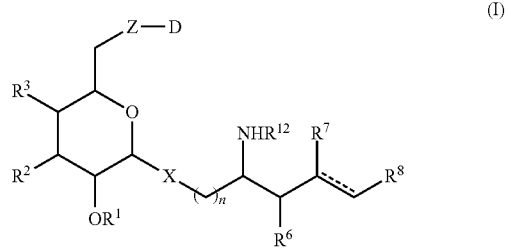

wherein

Z is S, S—S, SO or SO$_2$;

D is selected from the group consisting of:

hydrogen, halogen, hydroxyl, cyano, an optionally substituted alkyl group, an optionally substituted alkenyl group, an optionally substituted alkynyl group, an optionally substituted aralkyl group, an optionally substituted aryl group, a radical of formula D1, a radical of formula D2 and a radical of formula D3;

D1
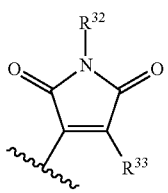

D2
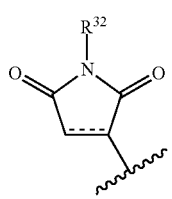

D3
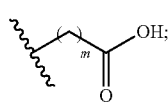

wherein $R^{32}$ is selected from the group consisting of: an optionally substituted alkyl group, an optionally substituted alkenyl group, an optionally substituted alkynyl group and an optionally substituted aryl group; $R^{33}$ is halogen; m is an integer from 2 to 10, and wherein ------- in D2 denotes an optional double bond;

provided that if D is halogen then Z is not S or S—S and provided that if D is cyano then Z is not S—S, SO or $SO_2$ and provided that if D is hydroxyl then Z is not S, S—S or SO;

$R^1$ is H or glycosyl, provided that if $R^1$ is glycosyl then $R^2$ and $R^3$ are both OH;

$R^2$ is selected from the group consisting of H, OH, F and $OR^{10}$; provided that if $R^2$ is H, F or $OR^{10}$, then $R^1$ is H, $R^3$ is OH;

$R^3$ is selected from the group consisting of H, OH, F and $OR^{10}$; provided that if $R^3$ is H, F or $OR^{10}$, then $R^1$ is H, $R^2$ is OH;

$R^6$ is OH or H;

$R^7$ is OH or H; wherein when $R^7$ is H, $R^8$ is $C_1$-$C_{15}$ alkyl and X is O, ------- denotes an optional double bond linking the carbon adjacent to $R^7$ with the carbon adjacent to $R^8$;

$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

X is O, $CH_2$ or S; wherein, when X is $CH_2$ then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is OH and $R^7$ is H, and $R^8$ is $C_{13}H_{27}$ and the stereochemistry at carbon atoms 2 and 3 is (2S, 3S); or when X is S then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R); or $R^6$ is OH and $R^7$ is H and the stereochemistry at the carbon atoms 2 and 3 is (2S, 3S);

n is 1 when X is O or S; or n is 0 or 1 when X is $CH_2$;

or a pharmaceutically acceptable salt thereof.

2. The compound of claim 1 which is a compound of formula (Ia)

(Ia)
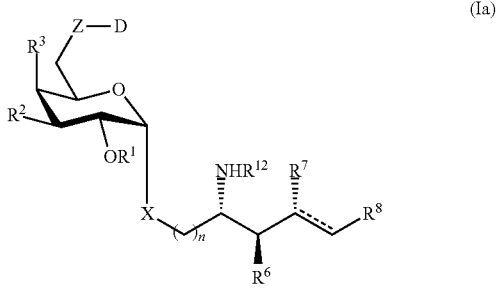

wherein X, Z, D, $R^1$, $R^2$, $R^3$, $R^6$, $R^7$, $R^8$, $R^{10}$, $R^{12}$, $R^{32}$ and n are all as defined in claim 1.

3. The compound of claim 1 wherein X is O.

4. The compound of claim 1 wherein n in formula (I) is 1, the stereochemistry of the 6-membered sugar ring of formula (I) is α-D-galacto, $R^6$ is OH, $R^7$ is OH and the stereochemistry at carbon atoms 2, 3 and 4 is (2S, 3S, 4R).

5. The compound of claim 1 wherein n in formula (I) is 0, the stereochemistry of the 6-membered sugar ring of formula (I) is α-D-galacto, $R^6$ is OH, $R^7$ is OH and the stereochemistry at carbon atoms 2, 3 and 4 is (2S, 3S, 4R).

6. The compound of claim 1 wherein X is O, $R^6$ is OH, $R^7$ is H, $R^8$ is $C_1$-$C_{15}$ alkyl and ------- is a double bond linking the carbon adjacent to $R^7$ with the carbon adjacent to $R^8$ and the stereochemistry at the carbon atoms 2, 3 is (2S, 3S).

7. The compound of claim 1 wherein D is an alkyl group.

8. The compound of claim 1 wherein D is hydrogen.

9. The compound of claim 1 which is a compound of formula (I.2), (I.3) or (I.4)

(I.2)

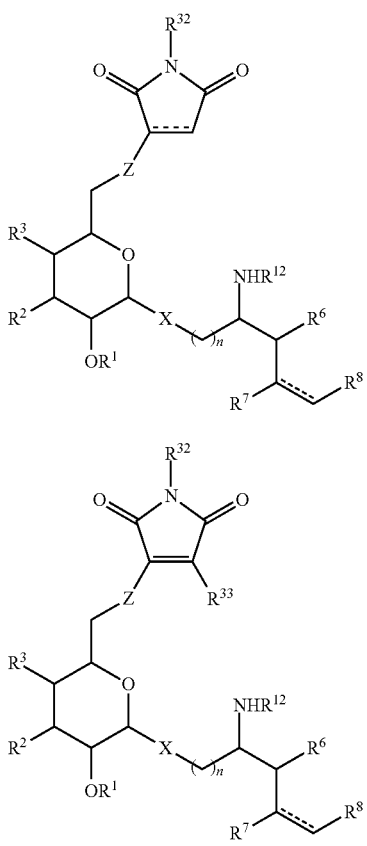

(I.3)

(I.4)

wherein X, Z, $R^1$, $R^2$, $R^3$, $R^6$, $R^7$, $R^8$, $R^{10}$, $R^{12}$, $R^{32}$, $R^{33}$ and n are all as defined in claim 1.

10. The compound of claim 1 wherein $R^{12}$ is a $C_{26}$-acyl group.

11. A compound of formula (IV)

(IV)

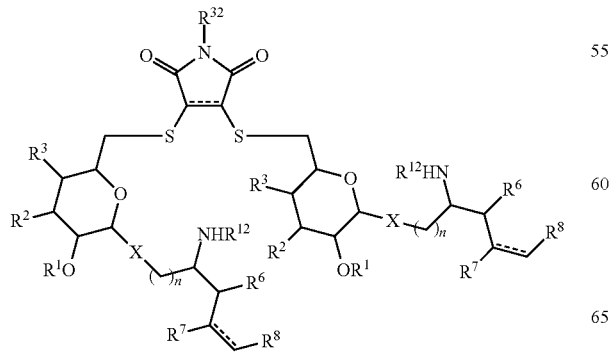

wherein X, Z, $R^1$, $R^2$, $R^3$, $R^6$, $R^7$, $R^8$, $R^{10}$, $R^{12}$, $R^{32}$, $R^{33}$ and n are all as defined in claim 1; and wherein ------- denotes an optional double bond;

or a pharmaceutically acceptable salt thereof.

12. A compound of formula (V)

(V)

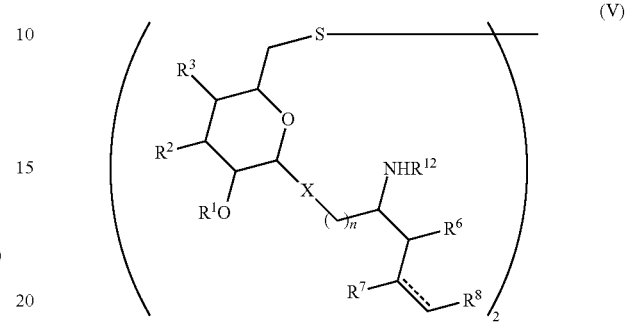

wherein X, Z, $R^1$, $R^2$, $R^3$, $R^6$, $R^7$, $R^8$, $R^{10}$, $R^{12}$ and n are all as defined in claim 1;

or a pharmaceutically acceptable salt thereof.

13. The compound of claim 11 wherein $R^{12}$ is a $C_{26}$ acyl group.

14. The compound of claim 12 wherein $R^{12}$ is a $C_{26}$-acyl group.

15. The compound of claim 1, selected from the group consisting of:

(a)

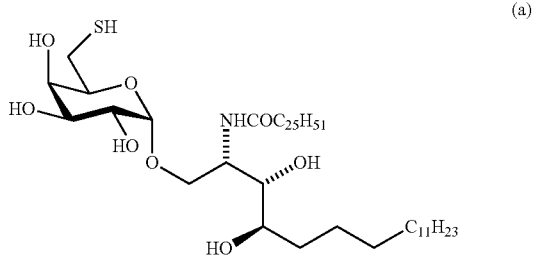

(b)

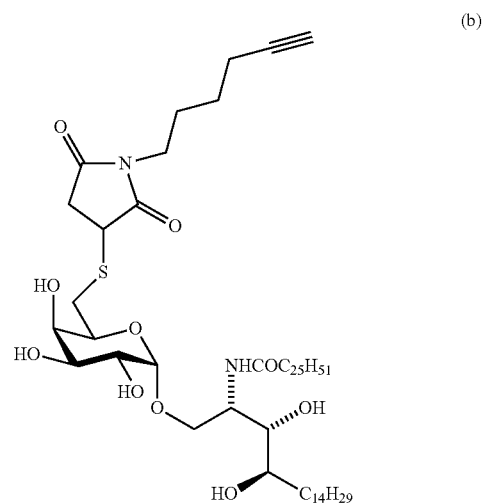

(c) 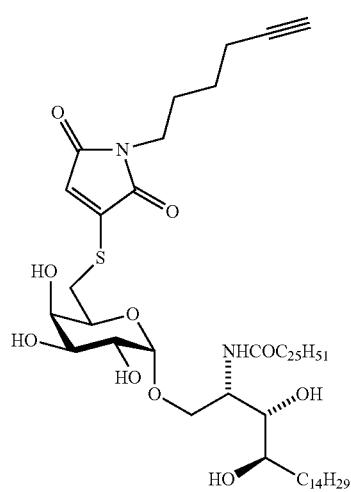
(d) 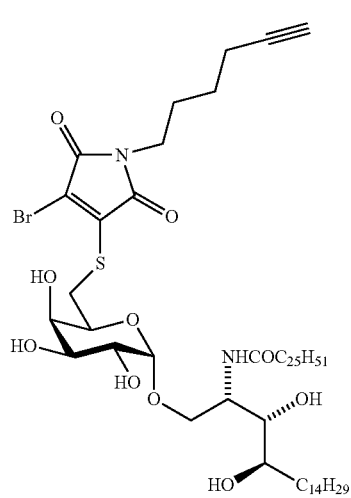
(e) 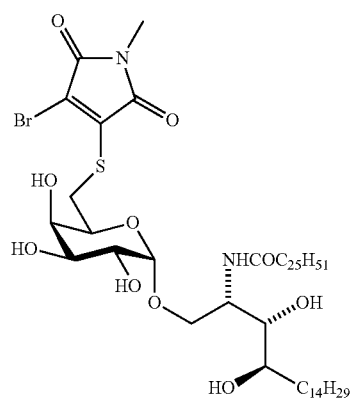
(f) 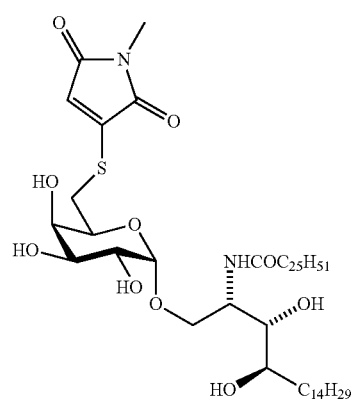
(g) 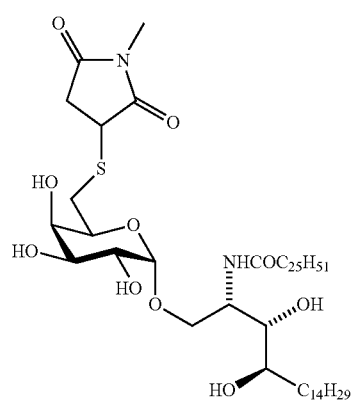
(h) 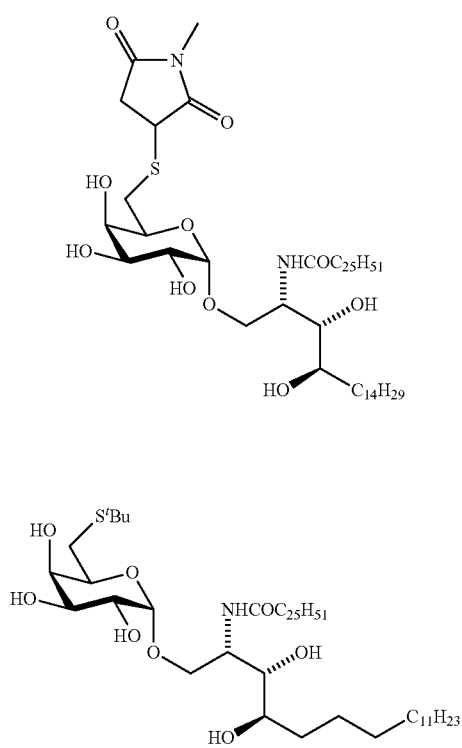
(j) 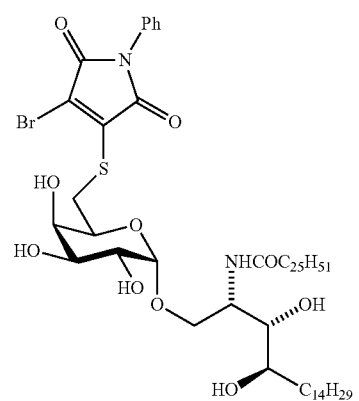

(k)
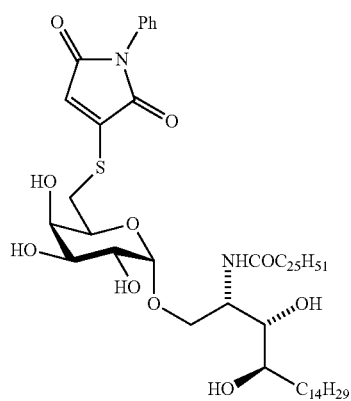
(m)
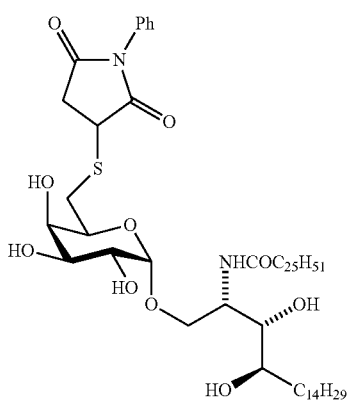
(n)
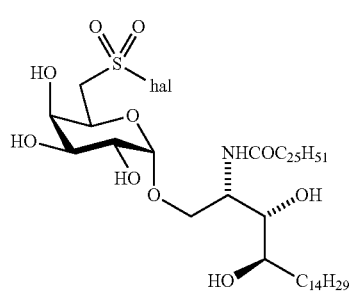
wherein hal is a halogen
(o)
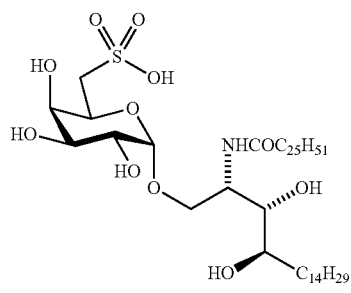
(p)
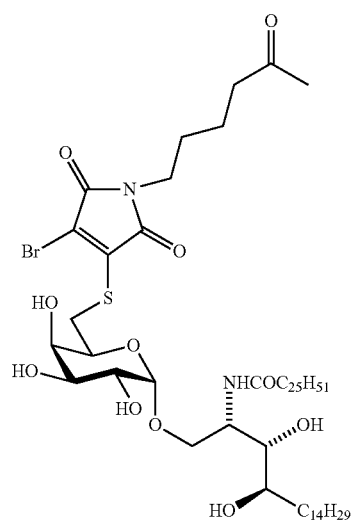
(q)
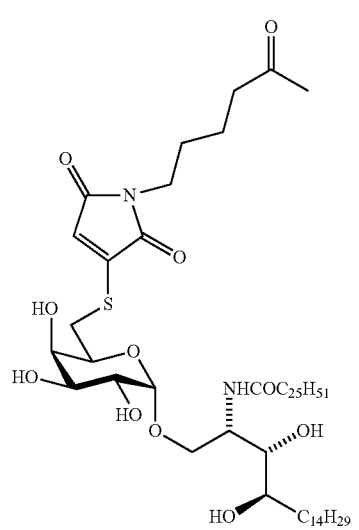
(r)
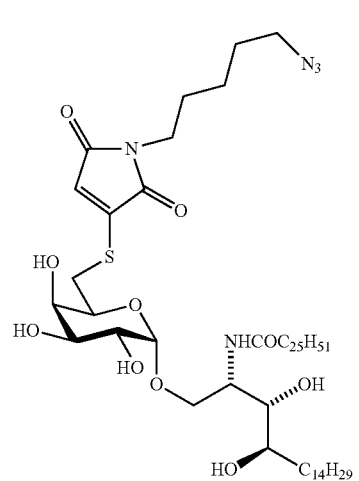

95
-continued
(s)
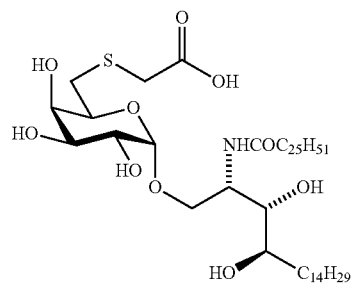
(t)
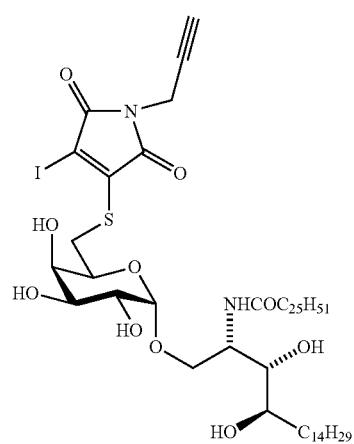
(u)
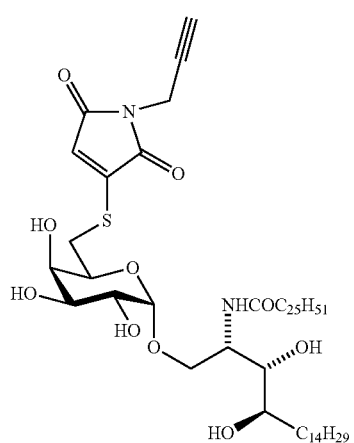
(v)
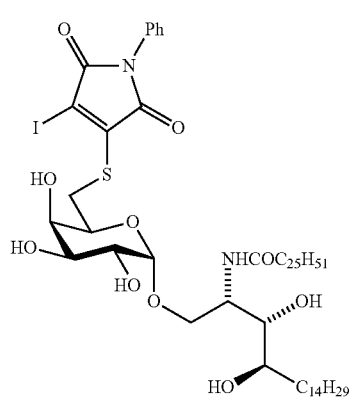
96
-continued
(w)
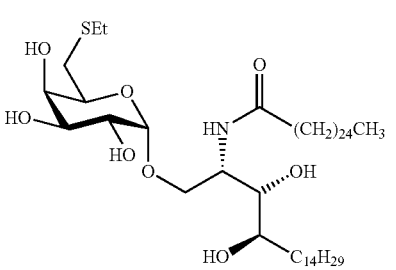
(x)
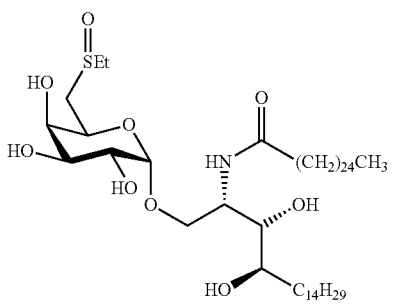
(y)
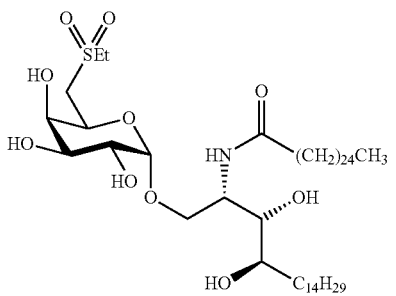
(z)
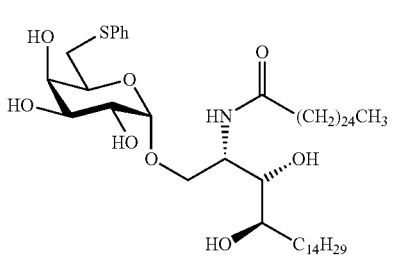
(aa)
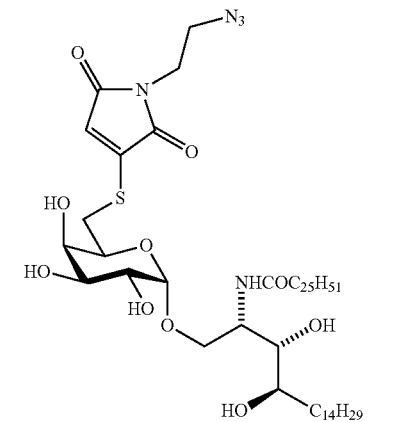

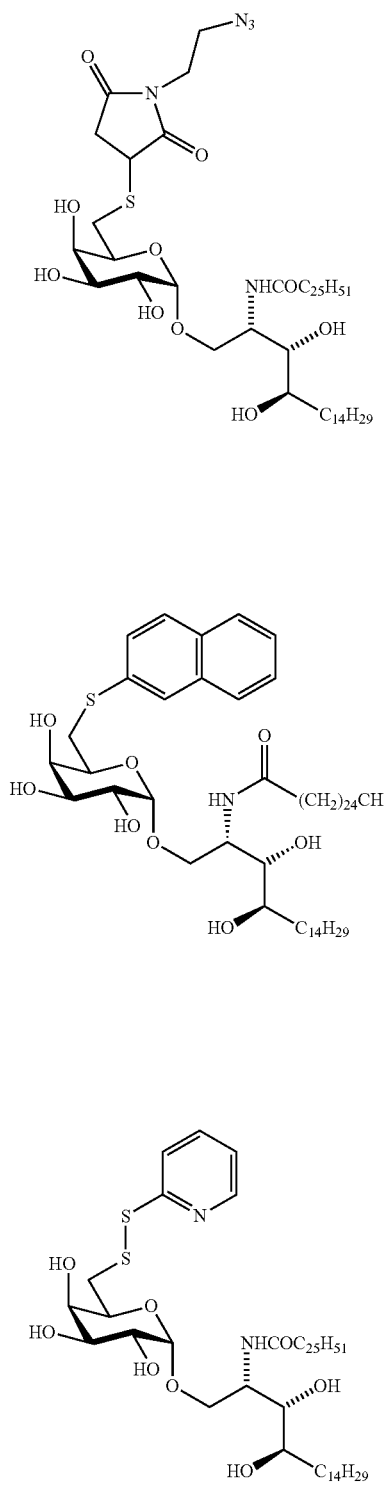

16. The compound of claim 1 wherein $R^8$ is $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group.

17. A pharmaceutical composition comprising a pharmaceutically effective amount of the compound of claim 1, and a pharmaceutically acceptable carrier.

18. The pharmaceutical composition of claim 17 which is a vaccine optionally comprising an antigen.

19. A method of modifying an immune response in a patient, comprising administering to the patient either (i) the compound of claim 1, or (ii) the compound of claim 1 and an antigen.

* * * * *

UNITED STATES PATENT AND TRADEMARK OFFICE
CERTIFICATE OF CORRECTION

PATENT NO.       : 9,717,790 B2                                    Page 1 of 1
APPLICATION NO.  : 14/897601
DATED            : August 1, 2017
INVENTOR(S)      : Regan James Anderson et al.

It is certified that error appears in the above-identified patent and that said Letters Patent is hereby corrected as shown below:

Column 98, Lines 20-35:

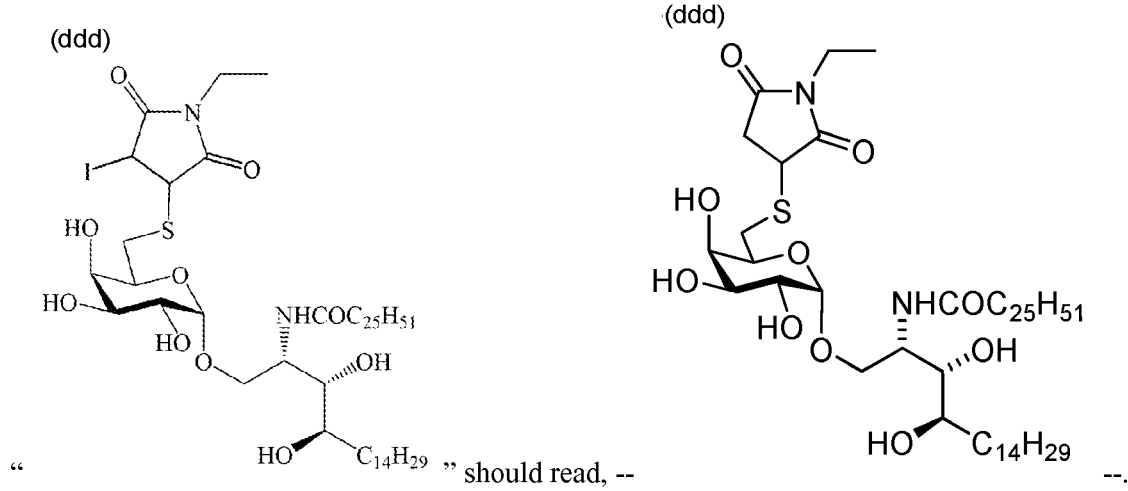

Signed and Sealed this
Fifth Day of December, 2017

Joseph Matal
*Performing the Functions and Duties of the
Under Secretary of Commerce for Intellectual Property and
Director of the United States Patent and Trademark Office*